(12) United States Patent
Gordon et al.

(10) Patent No.: US 7,741,434 B2
(45) Date of Patent: Jun. 22, 2010

(54) HIGH-AFFINITY ANTAGONISTS OF ELR-CXC CHEMOKINES

(76) Inventors: John R. Gordon, 342 Coldspring Crescent, Saskatoon Saskatchewan (CA) S7J 3N1; Fang Li, 342 Coldspring Crescent, Saskatoon Saskatchewan (CA) S7J 3N1

( * ) Notice: Subject to any disclaimer, the term of this patent is extended or adjusted under 35 U.S.C. 154(b) by 0 days.

(21) Appl. No.: 12/172,333

(22) Filed: Jul. 14, 2008

(65) Prior Publication Data

US 2009/0118469 A1 May 7, 2009

Related U.S. Application Data

(60) Division of application No. 11/434,155, filed on May 16, 2006, now abandoned, which is a continuation of application No. 10/087,273, filed on Mar. 1, 2002, now Pat. No. 7,201,895.

(60) Provisional application No. 60/273,181, filed on Mar. 1, 2001.

(51) Int. Cl.
*C07K 14/52* (2006.01)
(52) U.S. Cl. ...................................... 530/324
(58) Field of Classification Search .................. None
See application file for complete search history.

(56) References Cited

U.S. PATENT DOCUMENTS 5,665,346 A 9/1997 Clark-Lewis et al.

OTHER PUBLICATIONS

Clark-Lewis I et al: "Structural Requirements for Interleukin-8 Function Identified by Design of Analogs and CXC Chemokine Hybrids" Journal of Biological Chemistry, American Society of Biological Chemists, Baltimore, MD, US, vol. 269, No. 23.

Clark-Lewis I et al: "Structure-Activity Relationships of Chemokines" Journal of Leukocyte Biology, Federation of American Socieities for Experimental, US, vol. 57, No. 5, May 1, 1995, pp. 703-711, XP000569546 ISSN: 0741-5400 cited in the application the whole document.

Hayashi S et al: "Synthetic Hexa-and Heptapeptides That Inhibit IL-8 From Binding to and Activating Human Blood Neutrophils" Journal of Immunology, The Williams and Wilkins Co. Baltimore, US, vol. 154, 1995, pp. 814-824, XP002913718 ISSN: 0022-1767.

*Primary Examiner*—Prema Mertz
(74) *Attorney, Agent, or Firm*—Michael R. Williams; Ade & Company Inc.

(57) ABSTRACT

The present invention provides novel polypeptide sequences, methods for production thereof and uses thereof for novel ELR-CXC chemokine receptor agonists and antagonists.

1 Claim, 15 Drawing Sheets

FIGURE 7
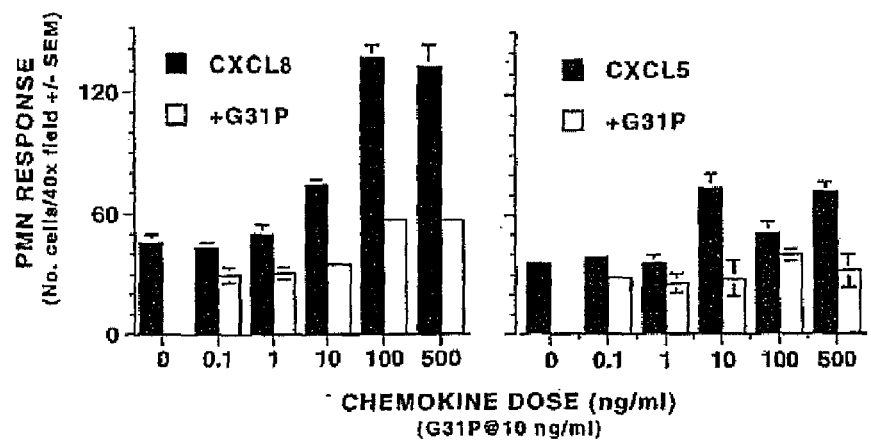
Fig.8 - physical characterization of hbG31P isoforms
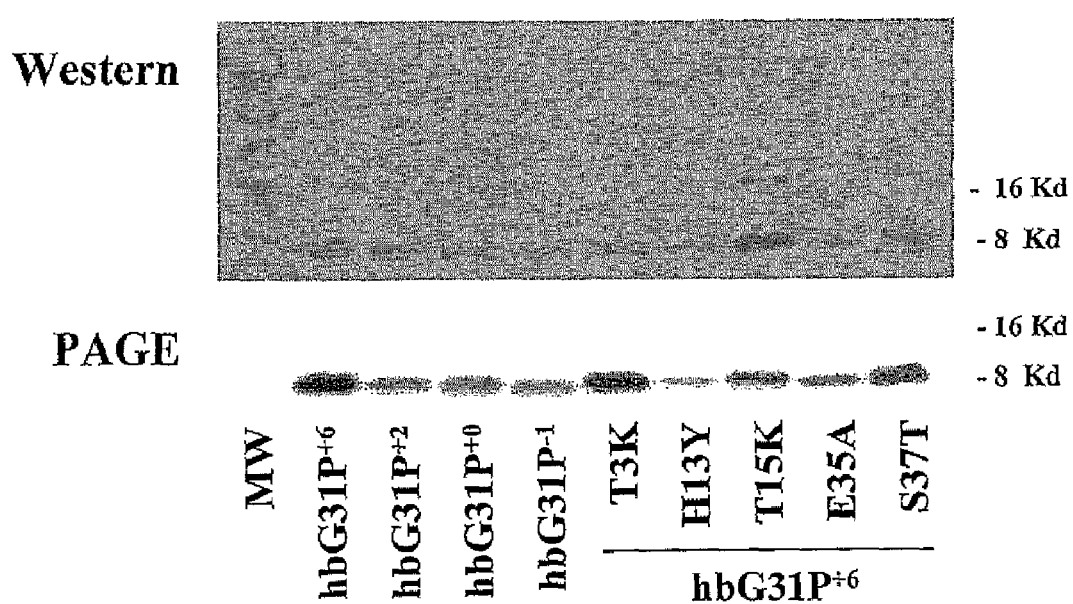

Fig 9 - comparison of bG31P & hbG31P (CXCL8 antagonism)
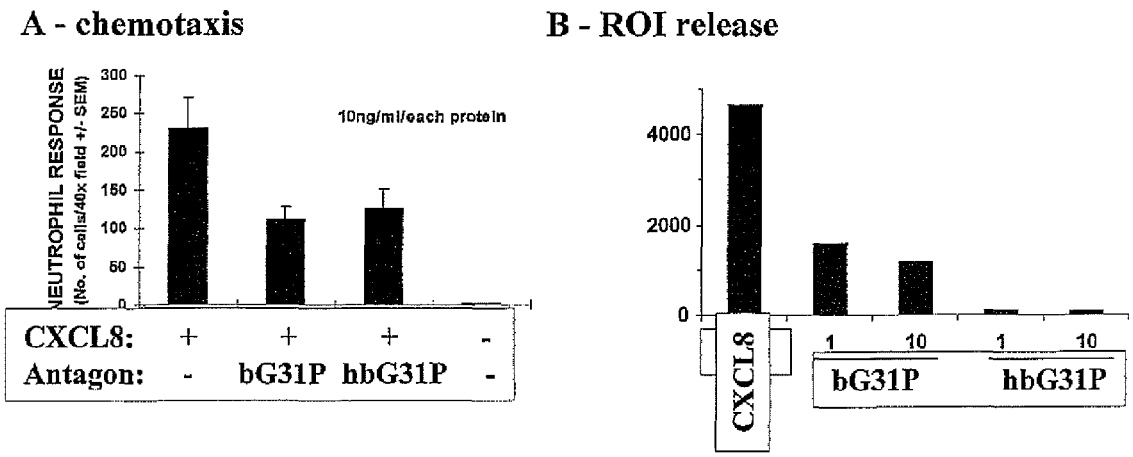
Fig. 10A - hbG31P analogues are not neutrophil chemotactic agonists
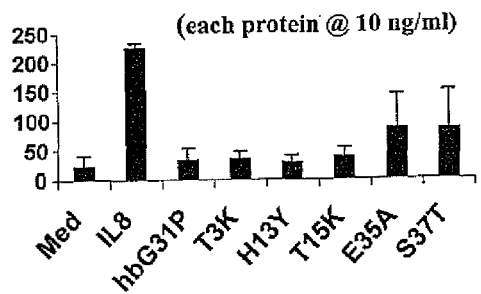
Fig. 10B - hbG31P antagonist activity (CXCL8 & hbG31P @ 10 ng/ml)
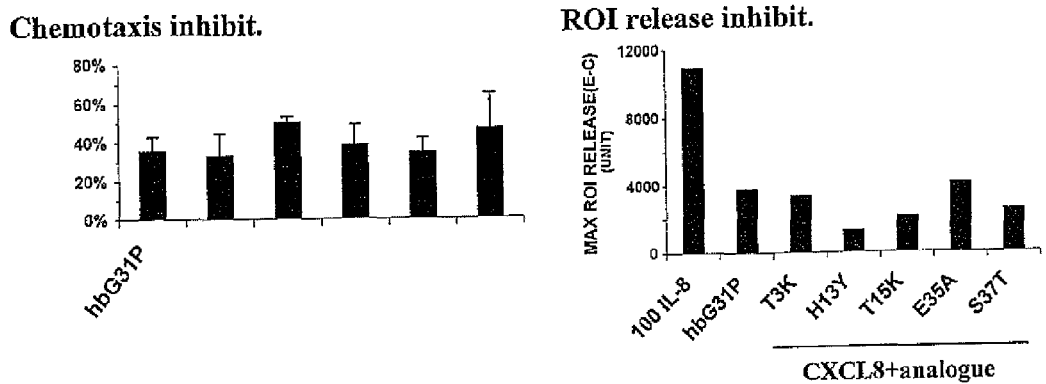

FIG. 11  Effect of the carboxy terminal sequence of hbG31P on its antagonist activities
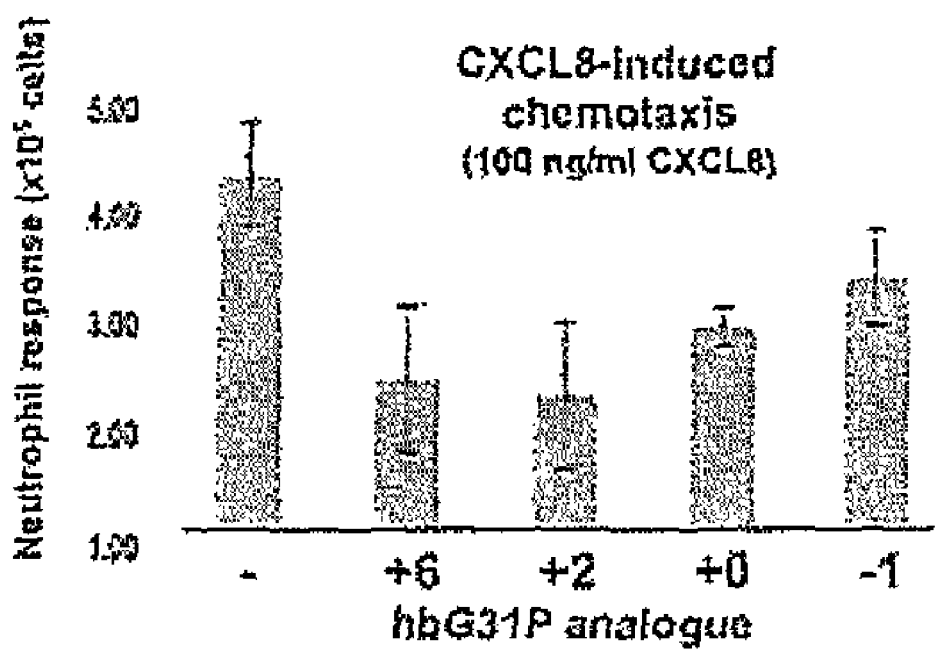
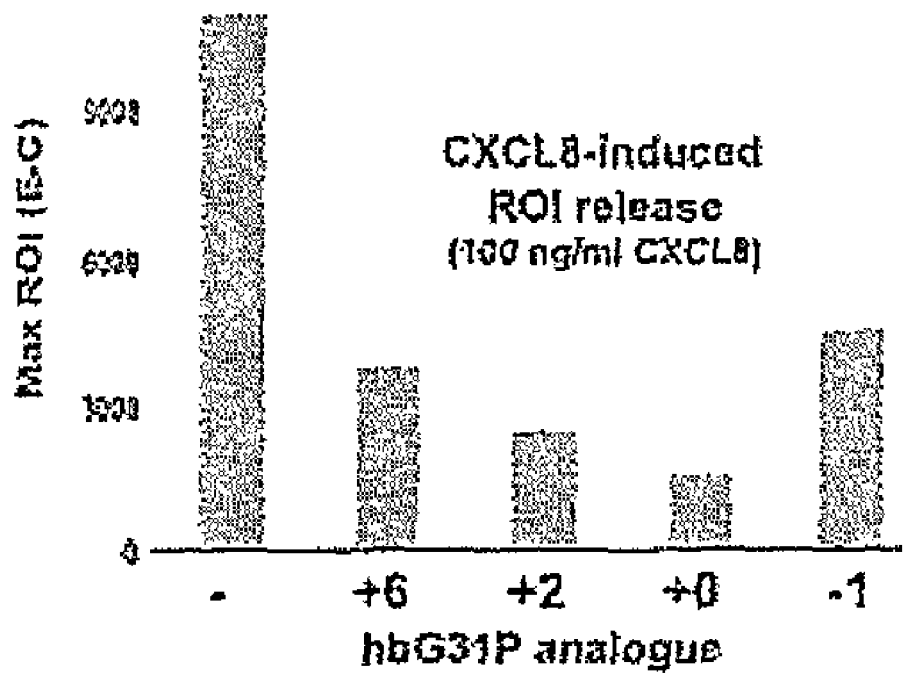

Fig 12A.
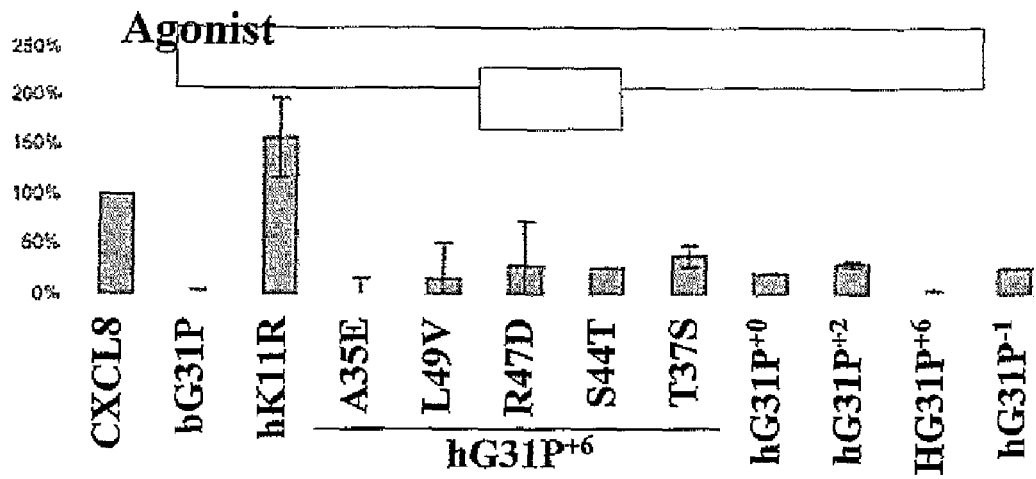
Fig 12B.
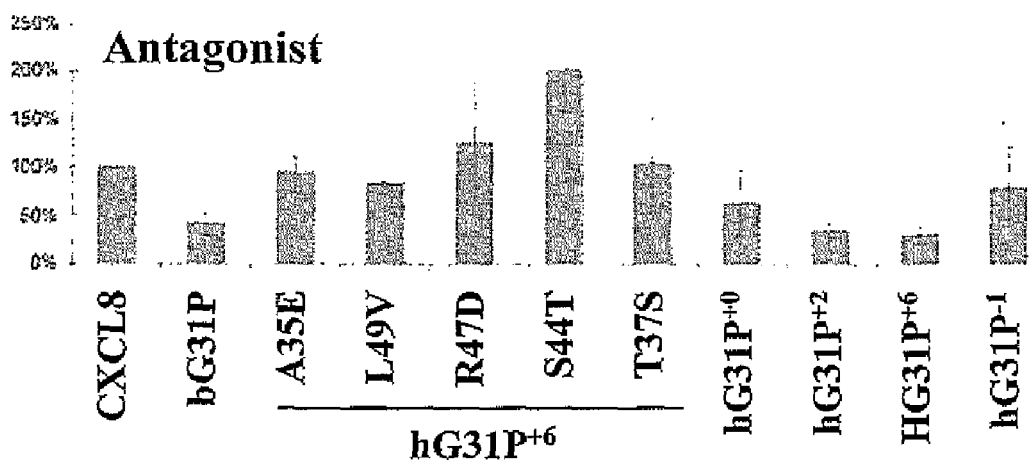
Fig 12C. Confirmation of hG31P antagonist activity
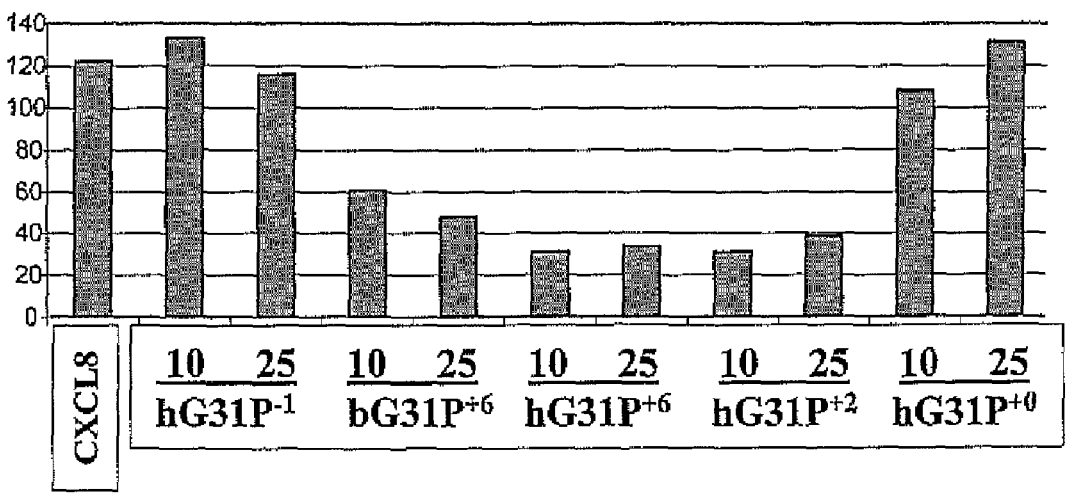

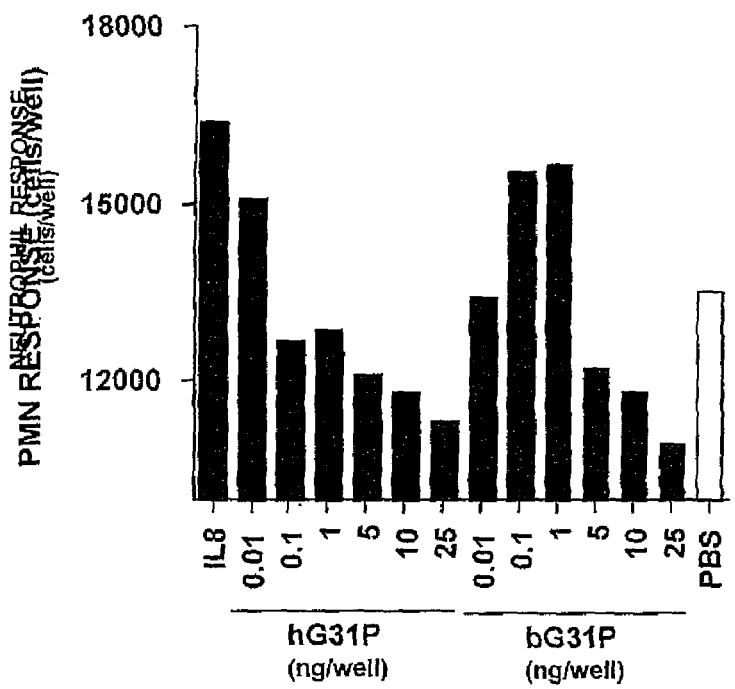
Fig 13. Comparison of the antagonist activities of bG31P and hG31P+6
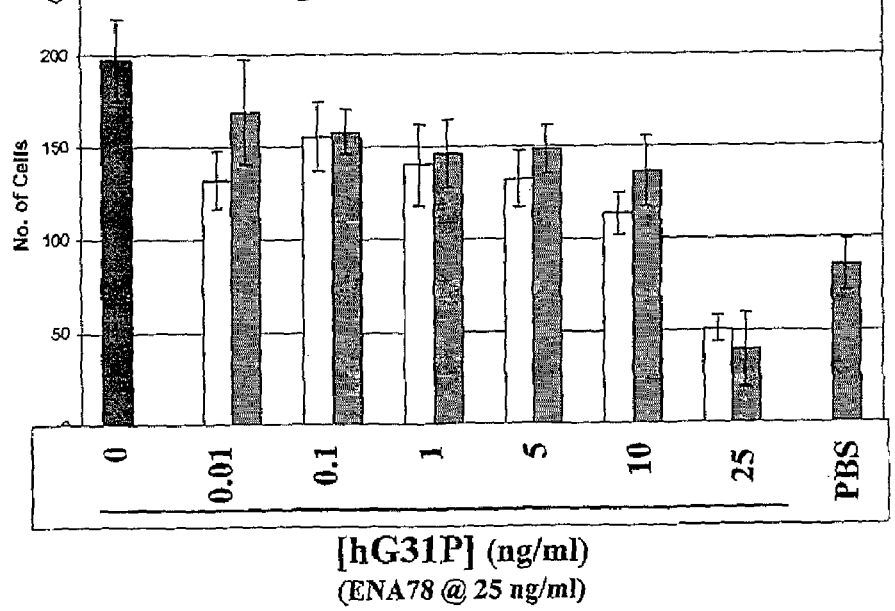
Fig 14. hG31P antagonizes ENA78, a CXCR2-specific ligand

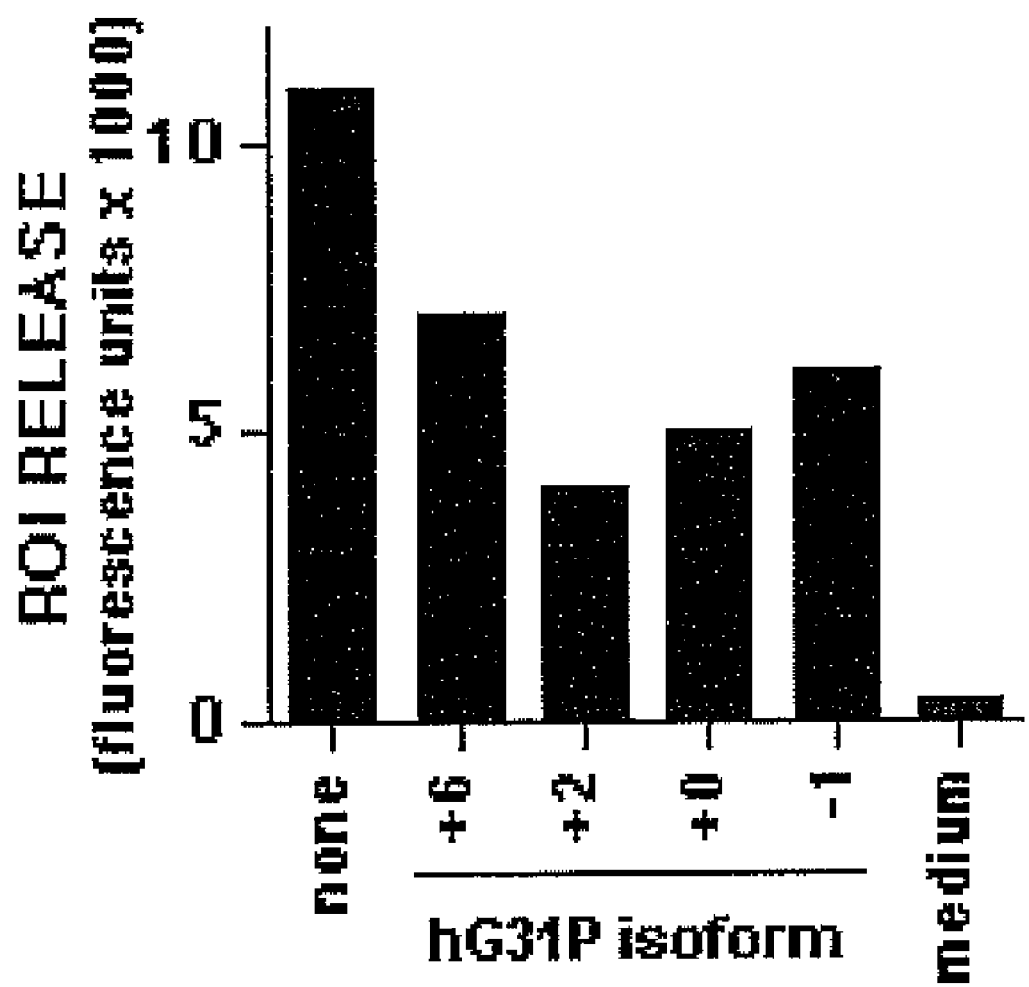
FIG. 15 hG31P antagonizes CXCL8-induced ROI release

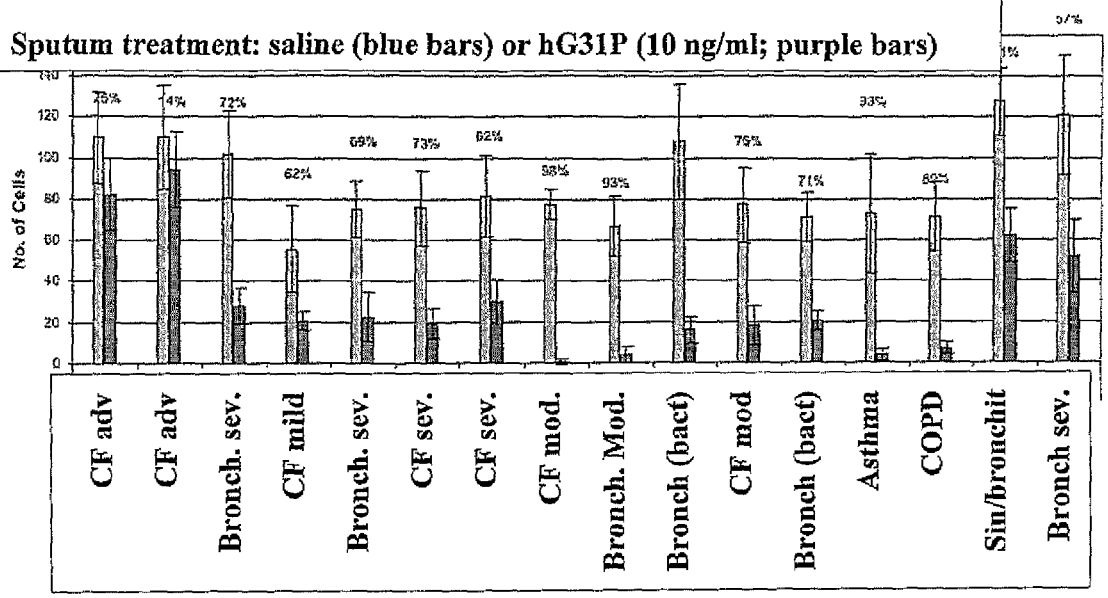

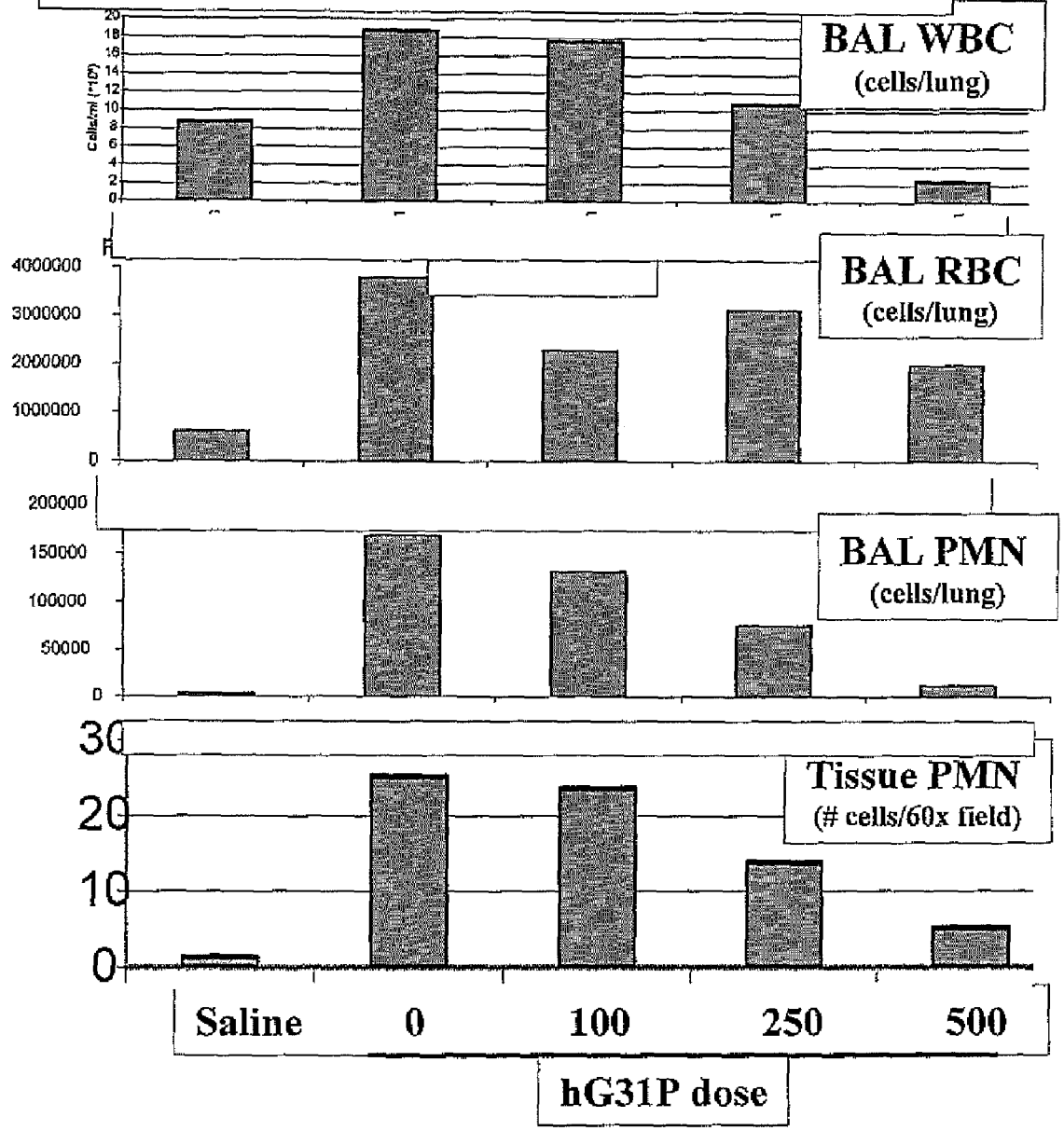

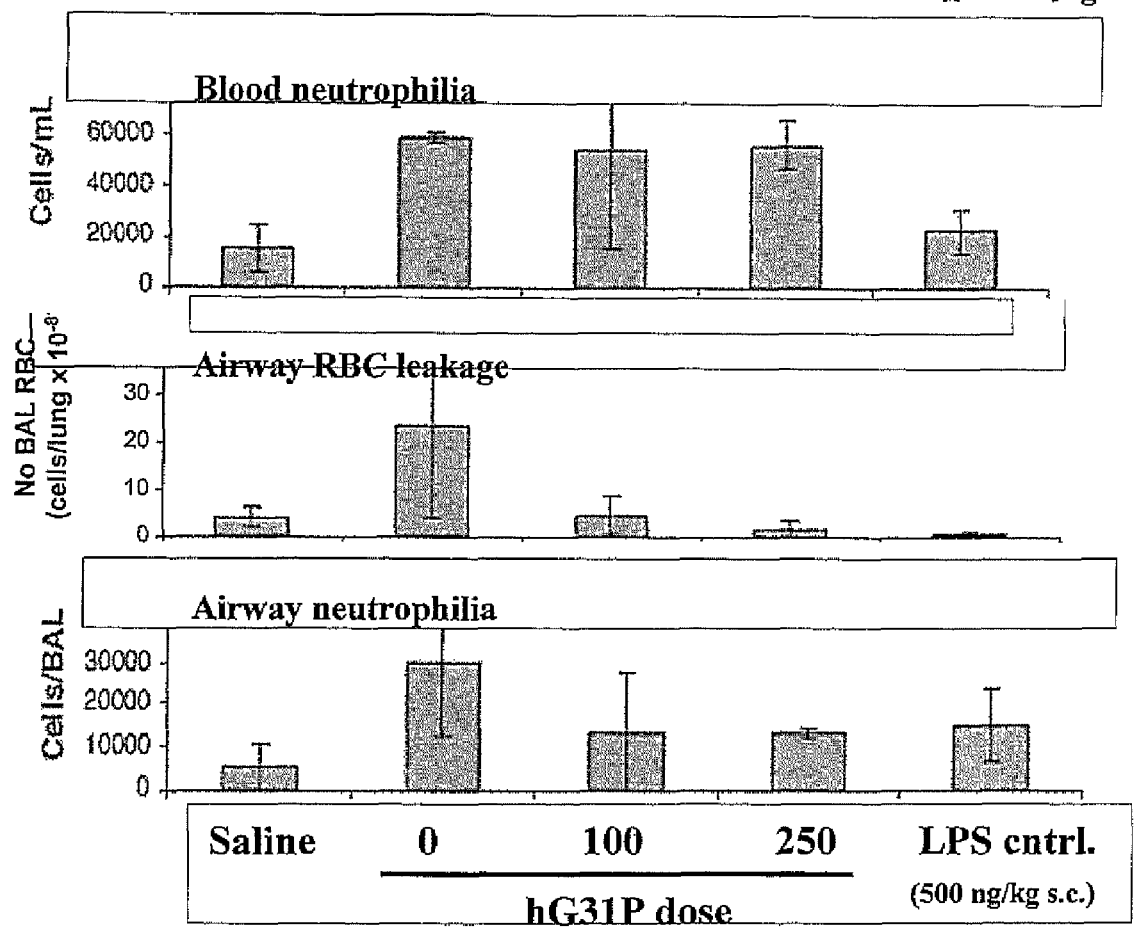
Fig. 18. Effect of hG31P in morbid airway endotoxemia in guinea pigs

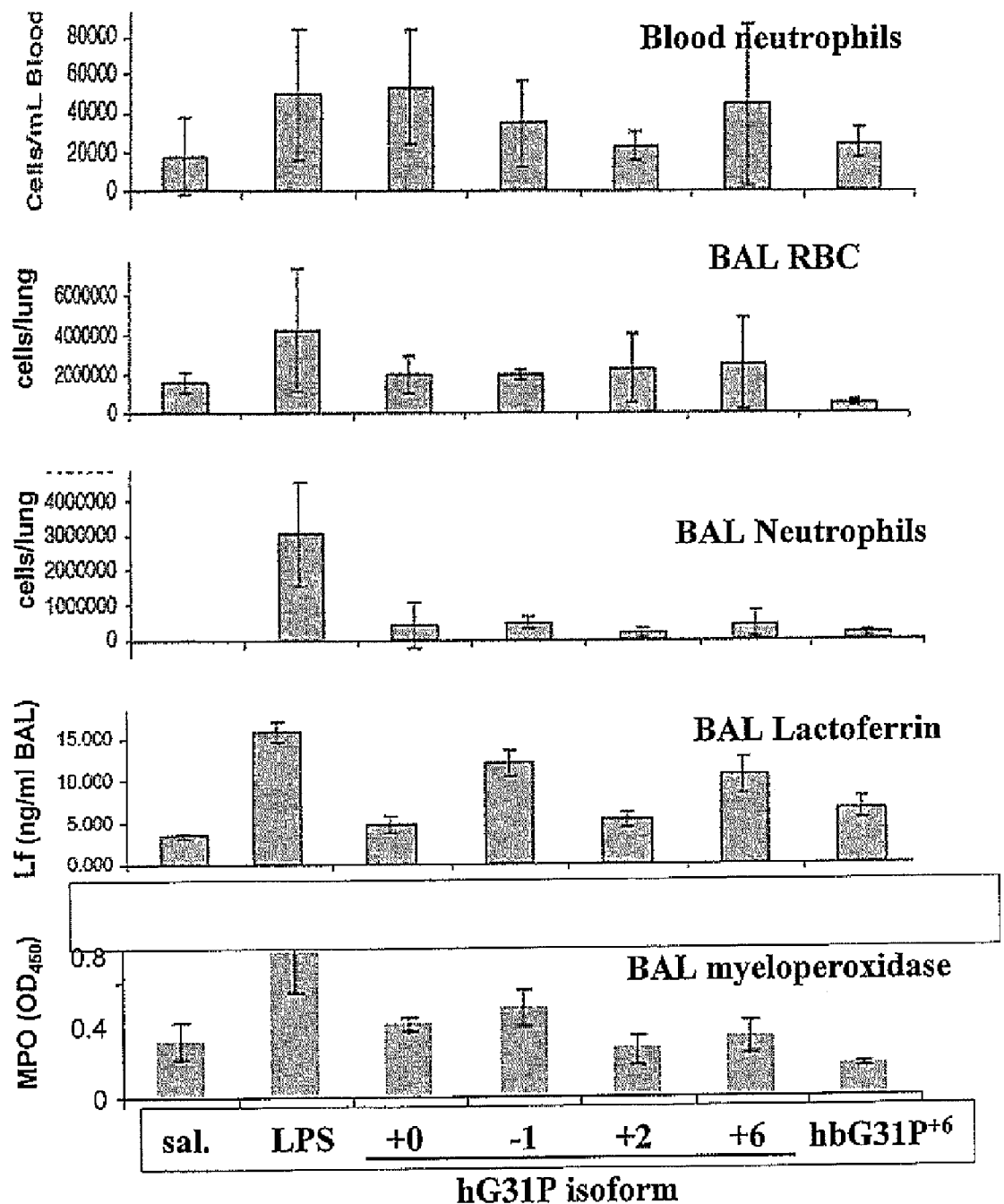
Fig. 19. Effect of various hG31P isoforms (& hbG31P) on airway endotoxemia pathology in guinea pigs

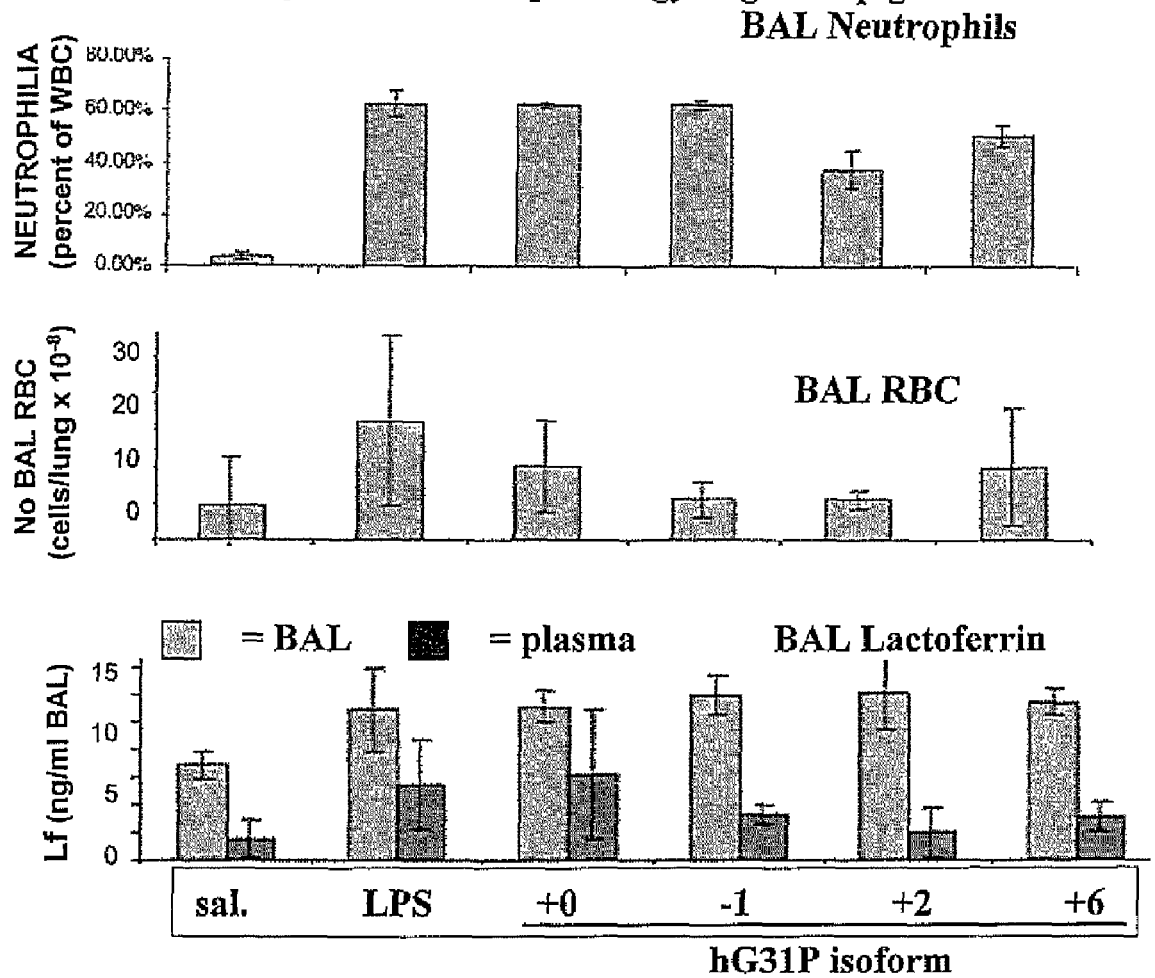
Fig. 20. Effect of various hG31P isoforms (& hbG31P) on airway endotoxemia pathology in guinea pigs

HIGH-AFFINITY ANTAGONISTS OF ELR-CXC CHEMOKINES

CROSS REFERENCE TO RELATED APPLICATION

This application is divisional application of U.S. patent application Ser. No. 11/434,155, filed May 16, 2006 which is a continuation-in-part of U.S. patent application Ser. No. 10/087,273, filed Mar. 1, 2002 which claims the benefit of U.S. Provisional Patent Application No. 60/273,181, filed on Mar. 1, 2001, now abandoned.

FIELD OF THE INVENTION

The present invention relates to the field of CXC chemokine receptor antagonists.

BACKGROUND OF THE INVENTION

The CXC chemokines that possess the receptor-signaling glutamic acid-leucine-arginine (ELR) motif (e.g., CXCL1/GRO□, CXCL8/IL-8; Baggiolini, M. 1998. Nature. 392:565-568) are important to the influx of inflammatory cells that mediates much of the pathology in multiple settings, including ischemia-reperfusion injury (Sekido, N. et al. 1993. Nature. 365:654-657; Villard, J. et al. 1995. Am. J. Respir. Crit. Care Med. 152:1549-1554), endotoxemia-induced acute respiratory distress syndrome (ARDS; Mukaida, N. et al. 1998. Inflamm. Res. 47 suppl. 3):S151-157), arthritis, and immune complex-type glomerulonephritis (Harada, A. et al. 1996. Inflamm. Res. 2:482-489). For instance, inappropriately released hydrolytic enzymes and reactive oxygen species from activated neutrophils initiate and/or perpetuate the pathologic processes. On the other hand, during most bacterial infections this chemokine response represents a critical first line of defense. But even here, ELR$^+$ CXC chemokine responses can, via their abilities to activate inflammatory cells displaying the CXCR1 and CXCR2 receptors, exacerbate the pathology. For example, during experimental 'cecal puncture and ligation' sepsis, neutralization of MIP-2 reduces mouse mortality from 85 to 38% (Walley, K. R. et al. 1997. Infect. Immun. 65:3847-3851). And experimental treatments that eliminate circulating neutrophils ameliorate the pathology of pneumonic mannheimiosis (Slocombe, R. et al. 1985. Am. J. Vet. Res. 46:2253), wherein CXCL8 expression in the airways variably affects the neutrophil chemoattraction. Caswell, J. L. et al. 1997. Vet. Pathol. 35:124-131; Caswell, J. L. et al. 2001. Canad. J. Vet. Res. 65:229-232). Despite the critical importance of these chemokine responses in many settings, wayward inflammatory cell responses are sufficiently damaging that the development of therapeutic tools with which we can block ELR$^+$ chemokines has become a research priority (Baggiolini, M., and B. Moser. 1997. J. Exp. Med. 186:1189-1191).

The 'ELR' chemokines chemoattract and activate inflammatory cells via their CXCR1 and CXCR2 receptors (Baggiolini, 1998; Ahuja, S. K., and P. M. Murphy. 1996. J. Biol. Chem. 271:20545-20550). Most mammals express orthologs (genes in different species that evolved from a common ancestral gene by speciation) of the CXCR1 and CXCR2 receptors and the 'ELR' chemokines. Sequence similarity between these homologous (genetically or functionally related) genes is high; higher still when conserved amino acid substitutions are considered. Mouse and rat are exceptions where these species do not have CXCR1 genes and their CXCL8 equivalent is highly divergent from that of other mammals. Interleukin 8 (CXCL8) is not species specific, in that the CXCL8 protein from one species can be functional in another species (Rot, 1991, Cytokine 3: 21-27).

The CXCR1 is specific for CXCL8 and CXCL6/granulocyte chemotactic protein-2 (GCP-2), while the CXCR2 binds CXCL8 with high affinity, but also macrophage inflammatory protein-2 (MIP-2), CXCL1, CXCL5/ENA-78, and CXCL6 with somewhat lower affinities (see, for example, Baggiolini and Moser, 1997). CXCL8 signaling in cell lines transfected with the human CXCR1 or CXCR2 induces equipotent chemotactic responses (Wuyts, A. et al. 1998. Eur. J. Biochem. 255:67-73; Richardson, R. et al. 1998. J. Biol. Chem. 273:23830-23836), and while neutrophil cytosolic free Ca$^{++}$ changes and cellular degranulation in response to CXCL8 are also mediated by both receptors, the respiratory burst and activation of phospholipase D reportedly depend exclusively on the CXCR1 (Jones, S. A. et al. 1996. Proc. Natl. Acad. Sci. U.S.A. 93:6682-6686.). On the other hand, it has been reported that a non-peptide antagonist of the CXCR2, but not the CXCR1, antagonizes CXCL8-mediated neutrophil chemotaxis, but not cellular activation (White, J. R. et al. 1998. J. Biol. Chem. 273:10095-10098.). Finally, there is abundant evidence that chemokines are most often redundantly expressed during inflammatory responses (see, for example, Caswell et al., 1997). But, despite active research in the field, no CXC chemokine antagonists are known in the prior art that are effective in suppressing adverse inflammatory cell activity induced by either ELR-CXC chemokine receptor.

SUMMARY OF THE INVENTION

Compositions of the present invention include novel ELR-CXC chemokine agonist and antagonist proteins that are capable of binding to CXCR1 or CXCR2 receptors in mammalian cells. These include agonists and antagonists that are capable of high-affinity binding, wherein "high-affinity" refers to the agonist's or antagonist's affinity for the receptor being sufficient such that it can block the wild-type chemokine agonist under physiologically relevant concentrations. The novel antagonist proteins also include those that are substantially equivalent (that is, those that contain amino acid substitutions, additions and deletions that do not delete the CXCR1 and CXCR2 binding functions) to a wild-type bovine and/or human CXCL8 protein (illustrated herein as the amino acid sequences of SEQ ID NO: 1 and SEQ ID NO:2) and also bear modified amino-terminal amino acid residues along with substitutions of Lys11 with Arg and Gly31 with Pro (SEQ ID No. 6). Analogues of this bovine CXCL8$_{(3-74)}$K11R/G31P are also included, namely CXCL8$_{(3-74)}$K11R/G31P/P32G (SEQ ID No. 7) and CXCL8$_{(3-74)}$K11R/T12S/H13F/G31P (SEQ ID No. 8).

Other compositions of the invention are novel polynucleotides and polypeptides relating to these proteins. In other embodiments, there are provided nucleotide sequences derived from the amino acid sequences. Further, the invention includes vectors comprising the novel polynucleotides, and expression vectors comprising the novel polynucleotides operatively associated with regulatory sequences controlling expression of the polynucleotides. Similarly, gene fusions comprising affinity handles and the novel polynucleotides are included in the invention, as are the resultant vectors and expression vectors containing such gene fusions.

The invention also includes hosts genetically engineered to contain the novel polynucleotides as well as hosts genetically engineered to contain the novel polynucleotides operatively associated with regulatory sequences, that is, associated with regulatory sequences in such a fashion that the regulatory sequences control expression of the novel polynucleotides. Also included are hosts containing gene fusions, either associated with regulatory sequences in such a fashion that the regulatory sequences control the expression of the gene fusions, or in the absence of such regulatory sequences. These hosts may be viruses or cells, wherein the latter include without limitation bacteria, yeast, protozoa, fungi, algae, plant cells, and animal cells and higher organisms derived therefrom.

The invention additionally comprises uses of the novel polypeptides in treating CXC chemokine-mediated pathologies involving the CXCR1 or CXCR2 receptors in mammals. Likewise, the invention includes methods of treating ELR-CXC chemokine-mediated pathologies involving the CXCR1 or CXCR2 receptors, comprising administering to the afflicted mammal an effective amount of one of the novel polypeptides. Pharmaceutical compositions comprising a biologically-active amount of one of the novel polypeptides are also included in the invention.

Methods of producing and purifying the novel polypeptides are also included in the invention.

In one aspect of the invention, there is provided a purified or isolated peptide having or comprising an amino acid sequence of:

XELRCXCIRX XSXPFXPKXI XEXXXIXSPP HCXNX-EIIVK LXXGXEXCLX PXXXWVQXXV XXFXKXX-EXX XX (SEQ ID No. 3), wherein X is any amino acid.

In another embodiment of the invention, there is provided an isolated or purified peptide comprising an amino acid sequence of:

```
X₁ELRCXCIRX XSXPFXPKXI XEXXXIXSPP HCXNXEIIVK

LXXGXEXCLX PXXXWVQXXV XXFXKXXEXX₂X₃X₄
``` wherein $X_1, X_2, X_3$ and $X_4$ are independently 0-10 amino acid residues.

In another embodiment of the invention, there is provided an isolated or purified peptide comprising an amino acid sequence of:
$X_1$ELRC$X_6$CIR$X_{10}$ $X_{11}$S$X_{13}$PF$X_{16}$PK$X_{19}$I $X_{21}$E$X_{23}$$X_{24}$$X_{25}$I$X_{27}$SPP HC$X_{33}$N$X_{35}$EIIVK L$X_{42}$$X_{43}$G$X_{45}$E$X_{47}$CL$X_{50}$ P$X_{52}$$X_{53}$$X_{54}$WVQ$X_{58}$$X_{59}$V $X_{61}$$X_{62}$F$X_{64}$K$X_{66}$$X_{67}$E$X_{69}$$X_{70}$$X_{71}$$X_{72}$ (defined consensus SEQ ID No. 4)

wherein
$X_1$ is 0-10 amino acids;
$X_6$ is Q, E or L;
$X_{10}$ is T or I;
$X_{11}$ is H or Y;
$X_{13}$ is T or K;
$X_{16}$ is H or N;
$X_{19}$ is F or Y or L;
$X_{21}$ is K or R;
$X_{23}$ is L or M;
$X_{24}$ is R or T;
$X_{25}$ is V or A;
$X_{27}$ is D or E;
$X_{33}$ is V or A or E;
$X_{35}$ is T or S;
$X_{42}$ is S or V or T or F;
$X_{43}$ is D or N;
$X_{45}$ is R or A or N or K or D;
$X_{47}$ is L or V;
$X_{50}$ is D or N;
$X_{52}$ is K or H;
$X_{53}$ is E or Q or T;
$X_{54}$ is P or N or K;
$X_{58}$ is R or K or I;
$X_{59}$ is V or I;
$X_{61}$ is E or Q;
$X_{62}$ is K or I or V or A;
$X_{64}$ is L or V;
$X_{66}$ is R or K;
$X_{67}$ is A or T;
$X_{69}$ is S or N or K or G;
$X_{70}$ is Q or S or K or deleted;
$X_{71}$ is N or D or deleted; and
$X_{72}$ is P or A or S or deleted.

According to another aspect of the invention, there is provided an isolated peptide consisting essentially of an amino acid sequence as set forth in any one of the following:

```
(bhG31P-SEQ ID No. 10)
GSTELRCQCIRTHSTPFHPKFIKELRVIESPPHCENSEIIVKLTDGRELC

LDPKENWVQRVVEKFLKRAENS;

(hG31P (0)-SEQ ID No. 11)
KELRCQCIRTYSKPFHPKFIKELRVIESPPHCANTEIIVKLSDGRELCLD

PKENWVQRVVEKFLKRAENS;

(hG31P (-1)-SEQ ID No. 12)
ELRCQCIRTYSKPFHPKFIKELRVIESPPHCANTEIIVKLSDGRELCLDP

KENWVQRVVEKFLKRAENS;

(hG31P (+2)-SEQ ID No. 13)
GSKELRCQCIRTYSKPFHPKFIKELRVIESPPHCANTEIIVKLSDGRELC

LDPKENWVQRVVEKFLKRAENS;

(hG31P (+6)-SEQ ID No. 14)
GSMGGSKELRCQCIRTYSKPFHPKFIKELRVIESPPHCANTEIIVKLSDG

RELCLDPKENWVQRVVEKFLKRAENS;

(hG31P K3T-SEQ ID No. 15)
GSTELRCQCIRTYSKPFHPKFIKELRVIESPPHCANTEIIVKLSDGRELC

LDPKENWVQRVVEKFLKRAENS;

(hG31P Y13H-SEQ ID No. 16)
GSKELRCQCIRTHSKPFHPKFIKELRVIESPPHCANTEIIVKLSDGRELC

LDPKENWVQRVVEKFLKRAENS;

(hG31P K15T (0)-SEQ ID No. 17)
GSKELRCQCIRTYSTPFHPKFIKELRVIESPPHCANTEIIVKLSDGRELC

LDPKENWVQRVVEKFLKRAENS;

(hG31P A35E (0) SEQ ID No. 18)
GSKELRCQCIRTYSKPFHPKFIKELRVIESPPHCENTEIIVKLSDGRELC

LDPKENWVQRVVEKFLKRAENS;

(hG31P T37S (0)-SEQ ID No. 19)
GSKELRCQCIRTYSKPFHPKFIKELRVIESPPHCANSEIIVKLSDGRELC

LDPKENWVQRVVEKFLKRAENS;

(hG31P S44T (0)-SEQ ID No. 20)
GSKELRCQCIRTYSKPFHPKFIKELRVIESPPHCANTEIIVKLTDGRELC

LDPKENWVQRVVEKFLKRAENS;
```

(hG31P R47D (0)-SEQ ID No. 21)
GSKELRCQCIRTYSKPFHPKFIKELRVIESPPHCANTEIIVKLSDGDELC
LDPKENWVQRVVEKFLKRAENS;

(hG31P N56K (0)-SEQ ID No. 22)
GSKELRCQCIRTYSKPFHPKFIKELRVIESPPHCANTEIIVKLSDGRELC
LDPKEKWVQRVVEKLFLKRAENS;

(hG31P R60K (0)-SEQ ID No. 23)
GSKELRCQCIRTYSKPFHPKFIKELRVIESPPHCANTEIIVKLSDGRELC
LDPKENWVQKVVEKFLKRAENS;

(hG31P K64V (0)-SEQ ID No. 24)
GSKELRCQCIRTYSKPFHPKFIKELRVIESPPHCANTEIIVKLSDGRELC
LDPKENWVQRVVEVFLKRAENS;

(hG31P L49V-SEQ ID No. 25)
GSKELRCQCIRTYSKPFHPKFIKELRVIESPPHCANTEIIVKLSDGREVC
LDPKNWVQRVVEKFLKRAENS;

(bhG31P T3K-SEQ ID No. 26)
GSKELRCQCIRTHSTPFHPKFIKELRVIESPPHCENSEIIVKLTDGRELC
LDPKENWVQRVVEKFLKRAENS;

(bhG31P H13Y-SEQ ID No. 27)
GSTELRCQCIRTYSTPFHPKFIKELRVIESPPHCENSEIIVKLTDGRELC
LDPKENWVQRVVEKFLKRAENS;

(bhG31P T15K-SEQ ID No. 28)
GSTELRCQCIRTHSKPFHPKFIKELRVIESPPHCENSEIIVKLTDGRELC
LDPKENWVQRVVEKFLKRAENS;

(bhG31P E35A-SEQ ID No. 29)
GSTELRCQCIRTHSTPFHPKFIKELRVIESPPHCANSEIIVKLTDGRELC
LDPKENWVQRVVEKFLKRAENS;

(bhG31P S37T-SEQ ID No. 30)
GSTELRCQCIRTHSTPFHPKFIKELRVIESPPHCENTEIIVKLTDGRELC
LDPKENWVQRVVEKFLKRAENS;

(bhG31P (+6)-SEQ ID No. 31)
GSMGGSTELRCQCIRTHSTPFHPKFIKELRVIESPPHCENSEIIVKLTDG
RELCLDPKENWVQRVVEKFLKRAENS;

(bhG31P (+2)-SEQ ID No. 32)
GSTELRCQCIRTHSTPFHPKFIKELRVIESPPHCENSEIIVKLTDGRELC
LDPKENWVQRVVEKYLKRAENS;

(bhG31P (+0)-SEQ ID No. 33)
TELRCQCIRTHSTPFHPKFIKELRVIESPPHCENSEIIVKLTDGRELCLDP
KENWVQRVVEKFLKRAENS;

(bhG31P (-1)-SEQ ID No. 34)
ELRCQCIRTHSTPFHPKFIKELRVIESPPHCENSEIIVKLTDGRELCLDP
KENWVQRVVEKFLKRAENS;

(hK11R (+6)-SEQ ID No. 35)
GSMGGSKELRCQCIRTYSKPFHPKFIKELRVIESGPHCANTEIIVKLSDG
RELCLDPKENWVQRVVEKFLKRAENS;

(hK11RG31P A35E (+6)-SEQ ID No. 36)
GSMGGSKELRCQCIRTYSKPFHPKFIKELRVIESPPHCENTEIIVKLSDG
RELCLDPKENWVQRVVEKFLKRAENS;

(hK11RG31P T37S (+6)-SEQ ID No. 37)
GSMGGSKELRCQCIRTYSKPFHPKIFIKELRVIESPPIICANSEIIVKLS
DGRELCLDPKENWVQRVVEKLFLKRAENS;

(hK11RG31P S44T (+6)-SEQ ID No. 38)
GSMGGSKELRCQCIRTYSKPFHPKFIKELRVIESPPHCANTEIIVKLTDG
RELCLDPKENWVQRVVEKFLKRAENS;

(hK11RG31P R47D (+6)1SEQ ID No. 39)
GSMGGSKELRCQCIRTYSKPFHPKFIKELRVIESPPHCANTEIIVKLSDG
DELCLDPKENWVQRVVEKFLKRAENS;

(hK11RG31P L49V-SEQ ID No. 40)
GSMGGSKELRCQCIRTYSKPFHPKFIKYLRVIESPPHCANTEIIVKLSDG
REVCLDPKENWVQRVVEKFLKRAENS;

(Bovine 3-74 K11RG31P (+2)-SEQ ID No. 41)
GSTELRCQCIRTHSTPFHPKFIKELRVIESPPHCENSEIIVKLTNGNEVC
LNPEKWVQKVVQVFVKRAEKQDP.

BRIEF DESCRIPTION OF THE DRAWINGS

FIG. 7 Neutrophils from the peripheral blood of a healthy donor were tested for their responses to recombinant human CXCL8 or CXCL5 in the presence or absence of bovine $CXCL8_{(3-74)}K11R/G31P$ (G31P; 10 ng/ml). G31P blocked the neutrophil's responses to both ligands.

FIG. 8 Physical characterization of hbG31P isoforms.

FIG. 9 Comparison of bG31P and hbG31P(CXCL8 antagonism)

FIG. 10A hbG31P analogues are not neutrophil agonists. FIG. 10B hbG31P antagonist activity.

FIG. 11 Effect of the carboxy terminal sequence of hbG31P on its antagonist activities.

FIG. 12 Agonist and CXCL8 analogues—activities of constructs

FIG. 13 Comparison of the antagonist activities of bG31P and hG31P+6

FIG. 14 hG31P antagonizes ENA78, a CXCR2-specific ligand

FIG. 15 hG31P antagonizes CXCL8-induced ROI release

FIG. 16 hG31P antagonizes neutrophil chemotactic activities in sputum of bronchiectasis and cystic fibrosis patients.

FIG. 17 hG31P reduces pulmonary inflammation in endotoxemic mice.

FIG. 18 Effect of hG31P in morbid airway endotoxemia in guinea pigs.

FIG. 19 Effect of various hG31P isoforms (and hbG31P) on airway endotoxemia pathology in guinea pigs.

FIG. 20 Effect of various hG31P isoforms (and hbG31P) on airway endotoxemia pathology in guinea pigs.

Figure 1:
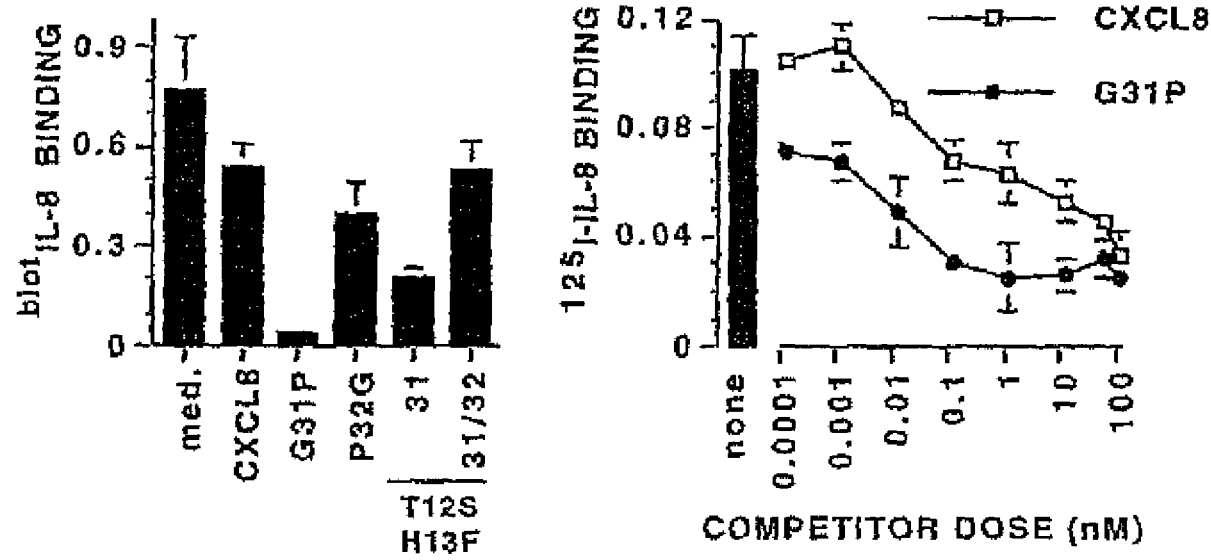
FIG. 1. The G31 P analogue of $CXCL8_{(3-74)}K11R$ is a potent inhibitor of CXCL8-binding to peripheral blood neutrophils. Bovine peripheral blood neutrophils (87-93% purity) were (upper panel) exposed at 4° C. for 2 h to $CXCL8_{(3-74)}K11R$ analogues (10 ng/ml) or medium (med) alone, then washed and similarly incubated with biotinylated CXCL8 ($^{biot}$CXCL8; 1000 ng/ml or 129 nM). These levels of CXCL8 approximate those found in the lung tissues of animals with pneumonic pasteurellosis (ref. 8, 9). The levels of $^{biot}$CXCL8 binding to the cells were determined using ELISA technology. The depicted amino acid substitutions within $CXCL8_{(3-74)}K11R$ included: G31P; P32G; T12S/H13P/G31P; and T12S/H13P/G31P/P32G. The G31P, but not the P32G, analogue was a highly effective antagonist of CXCL8 binding to the cells. With both the G31P and P32G analogues, additional substitutions of T12S and H13F reduced their CXCL8 antagonist activities (lower panel). Neutrophils were exposed simultaneously for 45 min at 4.degree. C. to varying concentrations of $CXCL8_{(3-74)}K11R/G31P$ or unlabeled CXCL8 and 20 pM $^{125}$ICXCL8. This level of $^{125}$I-CXCL8 was chosen as nearly saturating for the cell's high affinity CXCL8 receptors (data not shown). The levels of cell-associated $^{125}$I-CXCL8 were assessed using a counter. The data clearly indicate that $CXCL8_{(3-74)}K11R/G31P$ had a substantially higher affinity for the neutrophils than CXCL8.

DETAILED DESCRIPTION OF THE INVENTION (The following abbreviations are used throughout this disclosure: ARDS, acute respiratory distress syndrome; BALF, bronchoalveolar lavage fluid(s); BHR, Bolton-Hunter Reagent; CXCR1, CXCR2, CXCL8 receptors A, B, respectively; ELR, glutamic acid-lysine-arginine motif; CXCL1, growth-related oncogenealpha; CXCL4, platelet factor-4; CXCL5, epithelial-derived neutrophil activator-78; CXCL6, granulocyte chemotactic protein-2; CXCL8, interleukin-8; fMLP, formyl methionyl-leucylproline bacterial tripeptide; IPTG, isopropyl-thio-D-galactopyranoside; MIP-2, macrophage inflammatory protein-2; PMSF, phenylmethylsulfonyl fluoride; TMB, tetramethylbenzidine.)

As used herein, 'an agonist' refers to an agent that causes a cell to become activated.

As used herein, 'an antagonist' refers to an agent that prevents the cell from being activated in the presence or absence of the agonist, As used herein, "purified" does not require absolute purity but is instead intended as a relative definition. For example, purification of starting material or natural material to at least one order of magnitude, preferably two or three orders of magnitude is expressly contemplated as falling within the definition of "purified".

As used herein, the term "isolated" requires that the material be removed from its original environment.

As used herein, the term "treating" in its various grammatical forms refers to preventing, curing, reversing, attenuating, alleviating, minimizing, suppressing or halting the deleterious effects of a disease state, disease progression, disease causitive agent other abnormal condition.

When amino terminal truncation of bovine CXCL8 is combined with a lysine to arginine substitution at amino acid 11 (i.e., $CXCL8_{(3-74)}K11R$), dramatic increases in CXCR1 and CXCR2 receptor affinity are evident, such that $CXCL8_{(3-74)}$ K11R competitively inhibits the binding of multiple ligands to both receptors (Li, F., and J. R. Gordon. 2001. Biochem. Biophys. Res. Comm. 286:595-600., hereby incorporated by reference). Further truncation into the receptor-signaling ELR motif (e.g., amino acids 4-6 of human CXCL8) of some CXC chemokines can transform them into mild ($CXCL8_{(6-72)}$) to moderate ($CXCL1_{(8-73)}$) receptor antagonists (McColl and Clark Lewis 1999; Moser, B. et al. 1993. J. Biol. Chem. 268:7125-7128). As disclosed herein, the introduction into bovine $CXCL8_{(3-74)}K11R$ of a second amino acid substitution, glycine 31 to a proline residue (i.e., $CXCL8_{(3-74)}K11R/G31P$), renders this CXCL8 analogue a very high affinity antagonist of bovine and human ELR-CXC chemokine responses. It fully antagonizes the entire array of ELR-CXC chemokines expressed within bacterial or endotoxin-induced inflammatory foci and blocks endotoxin-induced inflammation in vivo.

Although the following discussion deals primarily with bovine neutrophils, other mammalian (including human) inflammatory cells also display CXCR1 and CXCR2 receptors (see, for example, Benson, M. et al. 1999. Pediatr. Allergy Immunol. 10:178-185) and so are vulnerable to inhibition by $CXCL8_{(3-74)}$K11R/G31P. Accordingly, the present invention has broad applicability to mammalian ELR-CXC chemokine-mediated pathologies.

As will be understood by one of skill in the art, in the nomenclature used herein, '3-74' refers to the fact that the native CXCL8 peptide is 74 amino acids long ('74') and the first two amino acids have been cleaved, meaning that the peptide sequence 'starts' at amino acid #3 of the native sequence. For consistency of nomenclature, the amino acids are referred to by number based on the wild type sequence and as such 'G31P' refers to the substitution of glycine at amino acid #31 of the wild type sequence with proline. As will be appreciated by one of skill in the art, with reference to SEQ ID No. 1, proline is in fact the $29^{th}$ amino acid in view of the deletion of the first two amino acids.

In other embodiments of the invention, there are provided ELR-CXC chemokine antagonist proteins that are capable of binding to CXCR1 or CXCR2 receptors in mammalian inflammatory cells. In a preferred embodiment, these peptides are substantially equivalent to a peptide having a sequence of SEQ ID No. 1, wherein, as will be appreciated by one of skill in the art, substantially equivalent means that these peptides have an amino acid sequence that is at least 60% identical, or at least 65% identical, or at least 70% identical, or at least 71%, or at least 72% identical, or at least 73% identical, or at least 74% identical, or at least 75% identical, or at least 76% identical, or at least 77% identical, or at least 78% identical, or at least 79% identical, or at least 80% identical, or at least 81% identical, or at least 82% identical, or at least 83% identical, or at least 84% identical or at least 85% identical, or at least 86% identical, or at least 87% identical or at least 88% identical or at least 89% identical or at least 90% identical or at least 91% identical or at least 92% identical or at least 93% identical or at least 94% identical or at least 95% identical to a wild-type CXCL8 protein (illustrated herein as the amino acid sequence of SEQ ID NO:2) and also have a truncation of the first two amino acid residues along with substitutions of Lys11 with Arg and Gly31 with Pro. As will be appreciated by one of skill in the art, in many embodiments, these peptides will be approximately 69, 70 or 72 amino acids long, as discussed below. However, in other embodiments, the peptides as described above may include deletions and/or insertions of 1, 2, 3, 4, 5, 6 or more amino acids. As will be appreciated by one of skill in the art, regions of a peptide which may tolerate an insertion or deletion can be predicted from the three dimensional structure of a peptide or by comparison of sequences from related organisms.

For example, with reference to Table 1 which shows the peptide alignment of wild type CXCL8 sequences from a number of species, including bovine, human, rhesus monkey, sheep, dog and pigs, one of the pig sequences includes an additional amino acid inserted between what corresponds to amino acids 60 and 61 of the wild type bovine sequence, indicating that this is a site that is likely to tolerate insertions of one or more amino acids in other species. Similarly, in the human and pig sequences, 2 and 3 amino acids respectively are deleted at the C-terminus relative the bovine sequence, suggesting that deletion of at least 2-3 amino acids from the C-terminus is likely to be tolerated in other species as well. As will be appreciated by one of skill in the art, this also indicates that addition or substitution of amino acids at the C-terminal end of these peptides is likely to be tolerated, that is, would not have a significantly negative effect on the desired biological activity of the peptide.

It is of note that it is well known in the art that some modifications and changes can be made in the structure of a polypeptide without substantially altering the biological function of that peptide, to obtain a biologically equivalent polypeptide. In one aspect of the invention, the above-described peptides may include peptides that differ by conservative amino acid substitutions. The peptides of the present invention also extend to biologically equivalent peptides that differ by conservative amino acid substitutions. As used herein, the term "conserved amino acid substitutions" refers to the substitution of one amino acid for another at a given location in the peptide, where the substitution can be made without substantial loss of the relevant function, in this case, the folding of the epitope. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide by routine testing. In these embodiments, function refers to CXCL8 chemokine antagonist activity.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (0); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In alternative embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Len (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In alternative embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, H is; neutral: Gly, Ser, Thr, Cys, Asn, Gln, Tyr.

In yet other embodiments, substitutions may be made wherein any known amino acid is substituted at a given position. In some embodiments, evolutionarily non-conserved or weakly conserved amino acids may be substituted with any for example, an amino acids of similar size but different hydrophobicity, similar charge but different size or other similar types of substitutions which will be understood by one of skill in the art.

Thus, analogues of $CXCL8_{(3-74)}$K11RG31P can be constructed wherein the desired biological function is retained by insertion, deletion and substitution of the sequence shown in SEQ ID No. 6, as discussed herein. It is further noted that exemplary analogues are shown in SEQ ID Nos. 7-41.

In a preferred embodiment, substantially equivalent analogues of $CXCL8_{(3-74)}$G31P are prepared using comparisons of related sequences from several species, for example, as shown in Table 1. As will be appreciated by one of skill in the art, substitution at highly variable amino acid locations is more likely to be tolerated than substitution at highly conserved amino acids.

For example, comparison of the sequences shown in Table 1, followed by deletion of the two N-terminal amino acids and substitution of glycine31 with proline and lysine 11 with arginine provides a sequence of:

XELRCXCIRX XSXPFXPKXI XEXXXIXSPP HCX-NXEIIVK LXXGXEXCLX PXXXWVQXXV XXFXKXXEXX XX (SEQ ID No. 3) wherein X is any amino acid.

In another embodiment of the invention, there is provided an isolated or purified peptide comprising an amino acid sequence of:

```
                                    (SEQ ID No. 42)
X₁ELRCXCIRX XSXPFXPKXI XEXXXIXSPP HCXNXEIIVK

LXXGXEXCLX PXXXWVQXXV XXFXKXXEXX₂X₃X₄
``` wherein $X_1$, $X_2$, $X_3$ and $X_4$ are independently 0-10 amino acid residues. That is, $X_1$ may be for example 6 random amino acids long whereas $X_2$, $X_3$ and $X_4$ may all be 0 amino acids long, that is, may be deleted. In other embodiments, $X_1$ may be 2 non-native amino acids, that is, not MS (bovine) or SA (human) but any other 2 amino acids, $X_2$ may be S or Q and $X_3$ and $X_4$ may be deleted.

Alternatively, $X_1$ may be 0-9 amino acids, 0-8 amino acids, 0-7 amino acids or 0-6 amino acids or 0-5 amino acids, or 0-4 amino acids, or 0-3 amino acids, or 0-2 amino acids, or $X_1$ may be selected from the group consisting of GSK, GST, S, A, T, K, GSMGGSK, and GSMGGST or $X_1$ may be deleted.

It is of note that in some embodiments there is provided the proviso that the peptide does not have the amino acid sequence of SEQ ID No. 6, 7, 8 or 9.

In another embodiment of the invention, there is provided an isolated or purified peptide comprising an amino acid sequence of:

$X_1$ELRC$X_6$CIR$X_{10}$ $X_{11}$S$X_{13}$PF$X_{16}$PK$X_{19}$I $X_{21}$E$X_{23}$$X_{24}$$X_{25}$I$X_{27}$SPP HC$X_{33}$N$X_{35}$EIIVK L$X_{42}$$X_{43}$G$X_{45}$E$X_{47}$CL$X_{50}$ P$X_{52}$$X_{53}$$X_{54}$WVQ$X_{58}$$X_{59}$V $X_{61}$$X_{62}$F$X_{64}$K$X_{66}$$X_{67}$E$X_{69}$$X_{70}$$X_{71}$$X_{72}$ (defined consensus SEQ ID No. 4)

wherein
$X_1$ is 0-10 amino acids;
$X_6$ is Q, E or L;
$X_{10}$ is T or I;
$X_{11}$ is H or Y;
$X_{13}$ is T or K;
$X_{16}$ is H or N;
$X_{19}$ is F or Y or L;
$X_{21}$ is K or R;
$X_{23}$ is L or M;
$X_{24}$ is R or T;
$X_{25}$ is V or A;
$X_{27}$ is D or E;
$X_{33}$ is V or A or E;
$X_{35}$ is T or S;
$X_{42}$ is S or V or T or F;
$X_{43}$ is D or N;
$X_{45}$ is R or A or N or K or D;
$X_{47}$ is L or V;
$X_{50}$ is D or N;
$X_{52}$ is K or H;
$X_{53}$ is E or Q or T;
$X_{54}$ is P or N or K;
$X_{58}$ is R or K or I;
$X_{59}$ is V or I;
$X_{61}$ is E or Q;
$X_{62}$ is K or I or V or A;
$X_{64}$ is L or V;
$X_{66}$ is R or K;
$X_{67}$ is A or T;
$X_{69}$ is S or N or K or G;
$X_{70}$ is Q or S or K or deleted;
$X_{71}$ is N or D or deleted; and
$X_{72}$ is P or A or S or deleted.

Alternatively, $X_1$ may be 0-9 amino acids, 0-8 amino acids, 0-7 amino acids or 0-6 amino acids or 0-5 amino acids, or 0-4 amino acids, or 0-3 amino acids, or 0-2 amino acids, or $X_1$ may be selected from the group consisting of GSK, GST, S, A, T, K, GSMGGSK, and GSMGGST or $X_1$ may be deleted.

In other embodiments, there is provided an isolated or purified peptide having or comprising or consisting essentially of an amino acid sequence as set forth in any one of SEQ ID No. 6-41 or SEQ ID No. 10-41. For reference, these amino acid sequences are as follows:

(Bovine 3-74 K11RG31P-SEQ ID No.6)
TELRCQCIRTHSTPFHPKFIKELRVIESPPHCENSEIIVKLTNGNEVCLN

PKEKWVQKVVQVFVKRAEKQDP (bovine 3-74 K11R P32G SEQ ID No. 7)
TELRCQCIRTHSTPFHPKFIKELRVIESGGHCENSEIIVKLTNGNEVCLN

PKEKWVQKVVQVFVKRAEKQDP (bovine-3-74 T12SH13PG3IP-SEQ ID No. 8)
TELRCQCIRSPSTPFHPKFIKELRVIESPPHCENSEIIVKLTNGNEVCLN

PKEKWVQKVVQVFVKRAEKQDP (bovine-3-74 T12SH13PG31PP32G-SEQ ID No. 9)
TELRCQCIRSPSTPFHPKFIKELRVIESPGHCENSEIIVKLTNGNEVCLN

PKEKWVQKVVQVFVKRAEKQDP (bhG31P-SEQ ID No. 10)
GSTELRCQCIRTHSTPFHPKFIKELRVIESPPHCENSEIIVKLTDGRELC

LDPKENWVQRVVEKFLKRAENS;

(hG31P (0)-SEQ ID No. 11)
KELRCQCIRTYSKPFHPKFIKELRVIESPPHCANTEIIVKLSDGRELCLD

PKENWVQRVVEKFLKRAENS;

(hG31P (-1)-SEQ ED No. 12)
ELRCQCIRTYSKPFHPKFIKELRVIESPPHCANTEIIVKLSDGRELCLDP

KENWVQRVVEKFLKRAENS;

(hG31P (+2)-SEQ ID No. 13)
GSKELRCQCIRTYSKPFHPKFIKELRVIESPPHCANTEIIVKLSDGRELC

LDPKENWVQRVVEKFLKRAENS;

(hG31P (+6)-SEQ ID No. 14)
GSMGGSKELRCQCIRTYSKPFHPKFIKELRVIESPPHCANTEIIVKLSDG

RELCLDPKLENWVQRVVEKFLKRAENS;

(hG31P K3T-SEQ ID No. 15)
GSTELRCQCIRTYSKPFHPKFIKELRVIESPPHCANTEIIVKLSDGRELC

LDPKENWVQRVVEKFLKRAENS;

(hG31P Y13H-SEQ ID No. 16)
GSKELRCQCIRTHSKPFHPKFIKELRVIESPPHCANTEIIVKLSDGRELC

LDPKENWVQRVVEKELKRAENS;

(hG31P K15T (0)-SEQ ID No. 17)
GSKELRCQCIRTYSTPFHPKIFKELRVIESPPHCANTEIIVKLSDGRELC

LDPKENWVQRVVEKFLKRAENS;

(hG31P A35E (0)-SEQ ID No. 18)
GSKELRCQCIRTYSKPFHPKFIKELRVIESPPHCENTEIIVKLSDGRELC

LDPKENWVQRVVEKFLKRAENS;

(hG31P T37S (0)-SEQ ID No. 19)
GSKELRCQCIRTYSKPFHPKFIKELRVIESPPHCANSEIIVKLSDGRELC

LDPKENWVQRVVEKFLKRAENS;

(hG31P S44T (0)-SEQ ID No. 20)
GSKELRCQCIRTYSKPFHPKFIKELRVIESPPHCANTEIIVKLTDGRELC

LDPKENWVQRVVEKFLKRAENS;

(hG31P R47D (0)-SEQ ID No. 21)
GSKELRCQCIRTYSKPFHPKFIKELRVIESPPHCANTEIIVKLSDGDELC

LDPKENWVQRVVEKFLKRAENS;

-continued (hG31P N56K (0)-SEQ ID No. 22)
GSKELRCQCIRTYSKPFHPKFIKELRVIESPPHCANTEIIVKLSDGRELC

LDPKEKWVQRVVEKFLKRAENS;

(hG31P R60K (0)-SEQ ID No. 23)
GSKELRCQCIRTYSKPFHPKFIKELRVIESPPHCANTEIIVKLSDGRELC

LDPKENWVQKVVEKFLKRAENS;

(hG31P K64V (0)-SEQ ID No. 24)
GSKELRCQCIRTYSKPFHPKFIKELRVIESPPHCANTEIIVKLSDGRELC

LDPKENWVQRVVEVFLKRAENS;

(hG31P L49V-SEQ ID No. 25)
GSKELRCQCIRTYSKPFHPKFIKELRVIESPPHCANTEIIVKLSDGREVC

LDPKENWVQRVVEKFLKRAENS;

(bhG31P T3K-SEQ ID No. 26)
GSKELRCQCIRTHSTPFHPKYIKELRVIESPPHCENSEIIVKLTDGRELC

LDPRENWVQRVVEKPLKRAENS;

(bhG31P H13Y-SEQ ID No. 27)
GSTELRCQCIRTYSTPFHPKFIKELRVIESPPHCENSEIIVKLTDGRELC

LDPKENWVQRVVEKFLKRAENS;

(bhG31P T15K-SEQ ID No. 28)
GSTELRCQCIRTHSKPFHPKFIKELRVIESPPHCENSEIIVKLTDGRELC

LDPKENWVQRVVEKFLKRAENS;

(bhG31P E35A-SEQ ID No. 29)
GSTELRCQCIRTHSTPFHPKFIKELRVIESPPHCANSEIIVKLTDGRELC

LDPKENWVQRVVEKFLKRAENS;

(bhG31P 537T-SEQ ID No. 30)
GSTELRCQCIRTHSTPFHPKFIKELRVIESPPHCENTEIIVKLTDGRELC

LDPKENWVQRVVEKFLKRAENS;

(bhG31P (+6)-SEQ ID No. 31)
GSMGGSTELRCQCIRTHSTPFHPKFIKELRVIESPPHCENSEIIVKLTDG

RELCLDPKENWVQRVVEKFLKRAENS;

(bhG31P (+2)-SEQ ID No. 32)
GSTELRCQCIRTHSTPFHPKFIKELRVIESPPHCENSEIIVKLTDGRELC

LDPKENWVQRVVEKFLKRAENS;

(bhG31P (+0)-SEQ ID No. 33)
TELRCQCIRTHSTPFHPKFIKLELRVIESPPHCENSEIIVKLTDGRELCL

DPKENWVQRVVEKFLKRAENS;

(bhG31P (-1)-SEQ ID No. 34)
ELRCQCIRTHSTPFHPKFIKELRVIESPPHCENSEIIVKLTDGRELCLDP

KENWVQRVVEKFLKRAENS;

(hK11R (+6)-SEQ ID No. 35)
GSMGGSKELRCQCIRTYSKPFHPKFIKELRVIESGPHCANTEIIVKLSDG

RELCLDPKENWVQRVVEKFLKRAENS;

(hK11RG31P A35E(+6)-SEQ ID No. 36)
GSMGGSKELRCQCIRTYSKPFHPKFIKELRVIESPPHCENTEIIVKLSDG

RELCLDPKENWVQRVVEKFLKRAENS;

(hK11RG31P T37S (+6)-SEQ ID No. 37)
GSMGGSKELRCQCIRTYSKPFHPKFIKELRVIESPPHCANSEIIVKLSDG

RELCLDPKENWVQRVVEKFLKRAENS;

-continued (hK11RG31P S44T (+6)-SEQ ID No. 38)
GSMGGSKELRCQCIRTYSKPFHPKFIKELRVIESPPHCANTEIIVKLTDG

RELCLDPKENWVQRVVEKFLKRAENS;

(hK11RG31P R47D (+6) SEQ ID No. 39)
GSMGGSKELRCQCIRTYSKPFHPKFIKLELRVIESPPHCANTEIIVKLSD

GDELCLDPKENWVQRVVEKFLKRAENS;

(hK11RG31P L49V-SEQ ID No. 40)
GSMGGSKELRCQCIRTYSKPFHPKFIKELRVIESPPHCANTEIIVKLSDG

REVCLDPKENWVQRVVEKFLKRAENS;
and (Bovine 3-74 K11RG31P (+2)-SEQ ID No. 41)
GSTELRCQCIRTHSTPFHPKFIKELRVIESPPHCENSEIIVKLTNGNEVC

LNPKEKWVQKVVQVFVKRAEKQDP.

As will be appreciated by one of skill in the art, 'consisting essentially of' as used in regard the above defined peptides refers to the fact that the peptides may include for example N-terminal and/or C-terminal deletions which do not materially affect the activity, that is, the ELR-CXC chemokine agonist or antagonist activity of the peptide in question.

In an alternate embodiment of the invention, it is envisioned that compounds having the same three dimensional structure at the binding site may be used as antagonists. Three dimensional analysis of chemical structure is used to determine the structure of active sites, including binding sites for chemokines. Chemical leads with high throughput screening have been used to generate and chemically optimize a selective antagonist of the CXCR2 (J Biol Chem, 1998, 273: 10095, herein incorporated by reference). A similar approach was also used to generate a CCR3 antagonist (J Biol Chem, 2000, 275:36626, herein incorporated by reference).

Wells et al (J Leuk Biol, 1996, 59:53, herein incorporated by reference), has employed nuclear magnetic resonance spectroscopy (NMR) to detail the three dimensional structure of ligands for CXCR, including both ELR and non-ELR CXC chemokines. With their NMR information, Wells et al generated multiple substitutions within the receptor binding sites of multiple chemokines, such that they could substantially alter the ligands' receptor specificities.

Material and Methods

Reagents & supplies. The following reagents were purchased commercially: glutathione-Sepharose, the expression vector pGEX-2T, Sephadex G-25 (Amersham-Pharmacia-Biotech, Baie d'Urf, PQ), Bolton-Hunter reagent, a protein biotinylation kit (Pierce Scientific, Rockford, Ill.), the sequencing vector pBluescript II KS, Pfu Turbo™ DNA polymerase (Stratagene, La Jolla, Calif.), a site-directed mutagenesis kit (QuickChange™; Boerhinger-Mannheim Canada, Laval, PQ), aprotinin, benzene, calcium ionophore A23187, chloramine T, cytochalasin B, dimethylformamide, endotoxin (*Escherichia coli* lipopolysaccharide, serotype 0127B8), isopropyl-thio-D-galactopyranoside (IPTG), leupeptin, p-nitrophenyl-D-glucuronide, mineral oil, silicon oil, tetramethylbenzidine (TMB), phenylmethylsulfonyl fluoride (PMSF), phorbol-12,13-myristate acetate (PMA), and Triton X-100 (Sigma Chemical Co, Mississauga, ON), a Diff-Quick staining kit (American Scientific Products, McGaw Pk, Ill.), human CXCL1, CXCL5, and CXCL8 (R & D Systems Inc, Minneapolis, Minn.), horse radish peroxidase (HRP)-conjugated anti-rabbit Ig (Zymed, South San Francisco, Calif.), DMEM, HBSS (Gibco, Grand Island, N.Y.), HRP-streptavidin (Vector Labs, Burlingame, Calif.), ABTS enzyme substrate (Kirkegaard & Perry Labs, Gaithersburg, Md.), bovine serum albumin (BSA), and Lymphocyte Separation Medium (ICN Pharmaceuticals, Aurora, Ill.).

Generation of $CXCL8_{(3-74)}K11R$ analogues. The high affinity CXCR1/CXCR2 ligand $CXCL8_{(3-74)}K11R$, and its T12S/H13F analogue were generated in accordance with the methods described in Li and Gordon (2001, supra). The Gly31Pro (G31P), Pro32Gly (P32G), and G31P/P32G analogues of these proteins were similarly generated by site-directed mutagenesis using PCR with the appropriate forward and reverse oligonucleotide primers (Table 1). The products from each reaction were digested with DpnI, ligated into the vector pGEX-2T, transfected into HB101 cells, and their sequences verified commercially (Plant Biotechnology Institute, Saskatoon). Briefly, the recombinant bacteria were lysed in the presence of a protease inhibitor cocktail (2 mM PMSF, 2 μg/ml aprotinin, and 2 μg/ml leupeptin) and the recombinant fusion proteins in the supernatants purified by affinity chromatography, using glutathione-Sepharose beads in accordance with the methods of Caswell et al. (Caswell, J. L., D. M. Middleton, and J. R. Gordon. 1998. Vet. Immunol. Immunopath. 67:327-340.). The $CXCL8_{(3-74)}K11R$ analogues were cleaved from the GST fusion proteins by thrombin digestion, dialysed against phosphate buffered saline (PBS), run through commercial endotoxin-removal columns, and then characterized by polyacrylamide gel electrophoresis (PAGE) and Western blotting with a goat anti-bovine CXCL8 antibody (provided by Dr. M. Morsey). Each purified analogue had a molecular mass of 8 kDa, was specifically recognized by the anti-CXCL8 antibody in the Western blotting, and had a relative purity of 96%, as determined by densitometric analysis of the PAGE gels.

Labeling of the recombinant proteins. We used $^{biot}$CXCL8 for the initial surveys of analogue binding to neutrophils and $^{125}$I-CXCL8 for the later stage assays of relative receptor affinity. CXCL8 was biotinylated and the levels of biotin substitution determined using a commercial kit, as noted in Li and Gordon (2001, supra). The $^{biot}$CXCL8 was substituted with 2.15 moles of biotin per mole of CXCL8. CXCL8 was radiolabeled with $^{125}$ using the Bolton-Hunter Reagent (BHR) method, as noted in detail (Li and Gordon 2001, supra). The labeled protein was separated from the unincorporated $^{125}$I-BHR by chromatography on Sephadex G50, and the labeled CXCL8 characterized for its relative affinity for neutrophils and the time required to achieve binding equilibrium, as noted in Li and Gordon (2001, supra).

$CXCL8_{(3-74)}K11R$ analogue binding assays. Cells (85-93% neutrophils) were purified from the blood of cattle in accordance with the Caswell method (Caswell, J. L. et al. 1998. Vet. Immunol. Immunopath. 67:327-340). In preliminary experiments, we determined that none of our analogues affected the viability of neutrophils, as determined by trypan blue dye exclusion. For the broad analogue surveys, neutrophils in HBSS/0.5% BSA were incubated for 2 h at 4° C. with the analogue, washed in cold DMEM, and then incubated for another 2 h at 4° C. with $^{biot}$CXCL8 (1000 ng/ml). The cell-associated biotin was detected by incubating the washed cells with alkaline phosphatase-conjugated streptavidin (1:700 dilution) and then with ABTS enzyme substrate. The $OD_{405}$ of the samples was determined using an ELISA plate reader. Medium-treated neutrophils routinely bound sufficient sup. biotCXCL8 to generate an $OD_{405}$ of 0.5-0.6.

For the in-depth studies with $CXCL8_{(3-74)}K11R/G31P$, we used $^{125}$I-CXCL8 in binding inhibition assays with unlabeled CXCL8 or $CXCL8_{(3-74)}K11R/G31P$. In preliminary experiments we determined that the binding equilibrium time of neutrophils for $^{125}$I-CXCL8 was 45 min and that 20 pM $^{125}$I-CXCL8 just saturated the cell's high affinity receptors. Thus, in our assays, $10^6$ purified neutrophils were incubated for 45 min on ice with 20 pM $^{125}$I-CXCL8 and varying concentrations of unlabeled competitor ligand. The cells were then sedimented through 6% mineral oil in silicon oil and the levels of cell-associated radio-ligand determined using a counter. The non-specific binding of $^{125}$ICXCL8 to the cells was assessed in each assay by including a 200-fold molar excess of unlabeled ligand in a set of samples. This value was used to calculate the percent specific binding (Coligan, J., A. Kruisbeek, D. Margulies, E. Shevach, and W. Strober. 1994. Current Protocols in Immunology. John Wiley & Sons, New York).

Neutrophil-glucuronidase release assay. The neutrophil-glucuronidase assay has been reported in detail (Li and Gordon 2001, supra). Briefly, cytochalasin B-treated neutrophils were incubated for 30 min with the CXCL8 analogues, then their secretion products assayed calorimetrically for the enzyme. -Glucuronidase release was expressed as the percent of the total cellular content, determined by lysing medium-treated cells with 0.2% (v/v) Triton X-100. Neutrophil challenge with the positive control stimulus PMA (50 ng/ml) and A23187 (1 µg/ml) induced 42+/−6% release of the total cellular-glucuronidase stores.

Samples from inflammatory lesions. We obtained broncho-alveolar lavage fluids (BALF) from the lungs of cattle (n=4) with diagnosed clinical fibrinopurulent pneumonic mannheimiosis (Caswell et al., 1997), as well as teat cistern wash fluids from cattle (n=4) with experimental endotoxin-induced mastitis (Waller, K. P. 1997. Vet. Immunol. Immunopathol. 57:239-251). In preliminary dose-response experiments we determined that 5 µg of endotoxin induced a strong (70-80% maximal) mammary neutrophil response. Thus, in the reported experiments mastitis was induced by infusion of 5 µg of endotoxin or carrier medium alone (saline; 3 ml volumes) into the teat cisterns of non-lactating Holstein dairy cows, and 15 h later the infiltrates were recovered-from the cisterns by lavage with 30 ml HBSS. The cells from the BALF and teat cistern wash fluids were sedimented by centrifugation and differential counts performed. Untreated and CXCL8-depleted (below) wash fluids were assessed for their chemokine content by ELISA (CXCL8 only) and chemotaxis assays.

Neutrophil chemotaxis assays. Microchemotaxis assays were run in duplicate modified Boyden microchemotaxis chambers using polyvinylpyrrolidone-free 5 µm pore-size polycarbonate filters, in accordance with known methods (Caswell et al., 1998; Cairns, C. M. et al. 2001. J. Immunol. 167:57-65). For each sample, the numbers of cells that had migrated into the membranes over 20-30 min were enumerated by direct counting of at least nine 40.times. objective fields, and the results expressed as the mean number of cells/40× field (+/−SEM). The chemoattractants included bovine or human CXCL8, human CXCL5 and CXCL1, pneumonic mannheimiosis BALF and mastitis lavage fluids (diluted 1:10-1:80 in HBSS), while the antagonists comprised mouse anti-ovine CXCL8 antibody 8M6 (generously provided by Dr. P. Wood, CSIRO, Australia) or the CXCL8$_{(3-74)}$K11R analogues. In some assays we preincubated the samples with the antibodies (5 µg/ml) for 60 min on ice (Gordon, J. R. 2000. Cell Immunol. 201:42-49). In others we generated CXCL8-specific immunoaffinity matrices with the 8M6 antibodies and protein-A-Sepharose beads and used these in excess to absorb the samples (Caswell et al., 1997; Gordon, J. R., and S. J. Galli. 1994. J. Exp. Med. 180:2027-2037); the extent of CXCL8 depletion was confirmed by ELISA of the treated samples. For assays with the recombinant antagonists, the inhibitors were mixed directly with the samples immediately prior to testing.

CXCL8 ELISA. For our ELISA, MAb 8M6 was used as the capture antibody, rabbit antiovine CXCL8 antiserum (also from P. Wood, CSIRO) as the secondary antibody, and HRP-conjugated anti-rabbit Ig, and TMB as the detection system, as noted in Caswell et al. (1997). Serial dilutions of each sample were assayed in triplicate, and each assay included a recombinant bovine CXCL8 standard curve.

CXCL8$_{(3-74)}$K11R/G31P blockade of endotoxin responses in vivo. We used a sequential series of 15 h skin tests to test the ability of CXCL8$_{(3-74)}$K11R/G31P to block endotoxin induced inflammatory responses in vivo. For each test, we challenged 2 week-old healthy Holstein cows intradermally with 1 µg endotoxin in 100 µl saline, then 15 h later took 6 mm punch biopsies under local anaesthesia (lidocaine) and processed these for histopathology (Gordon and Galli, 1994). Following the first (internal positive control) test, we injected each animal subcutaneously, intramuscularly, or intravenously with CXCL8$_{(3-74)}$K11R/G31P (75 µg/kg) in saline, then challenged them again with endotoxin, as above. The animals were challenged a total of 4 times with endotoxin, such that 15 h reaction site biopsies were obtained at 0, 16, 48, and 72 h post-treatment. The biopsies were processed by routine methods to 6.mu.m paraffin sections, stained with Giemsa solution, and examined in a blinded fashion at 400-magnification (Gordon and Galli, 1994; Gordon, J. R. 2000. J. Allergy Clin. Immunol. 106:110-116). The mean numbers of neutrophils per 40× objective microscope field were determined at three different depths within the skin, the papillary (superficial), intermediate, and reticular (deep) dermis.

Statistical analyses. Multi-group data were analyzed by ANOVA and post-hoc Fisher protected Least Significant Difference (PLSD) testing, while two-group comparisons were made using the students t-test (two-tailed). The results are expressed as the mean+/−SEM.

Results

1. Bovine G31P

CXCL8$_{(3-74)}$K11R/G31P competitively inhibits CXCL8 binding to neutrophils. We surveyed the ability of each CXCL8$_{(3-74)}$K11R analogue to bind to the CXCL8 receptors on neutrophils, and thereby compete with CXCL8 as a ligand. In our initial surveys, we employed $^{biot}$CXCL8 binding inhibition assays, incubating the cells with the analogues (10 ng/ml) for 2 h at 4° C. prior to exposure to $^{biot}$CXCL8 (1 µg/ml). This level of CXCL8 approximates those found in the lung tissues of sheep with experimental pneumonic mannheimiosis (Caswell, J. L. 1998. The role of interleukin-8 as a neutrophil chemoattractant in bovine bronchopn-eumonia. Ph.D. thesis, Department of Veterinary Pathology, University of Saskatchewan). We found that CXCL8$_{(3-74)}$K11R/G31P was a potent antagonist of CXCL8 binding in this assay (FIG. 1), such that 10 ng/ml of CXCL8$_{(3-74)}$K11R/G31P blocked 95% of subsequent $^{biot}$CXCL8 binding to the cells. When tested at this dose, CXCL8$_{(3-74)}$K11R/P32G blocked only 48% of CXCL8 binding, while unlabeled CXCL8 itself competitively inhibited 30% of $^{biot}$CXCL8 binding. Introduction into CXCL8$_{(3-74)}$K11R/G31P or CXCL8$_{(3-74)}$K11R/P32G of additional amino acid substitutions at Thr12 and His13 substantially reduced the antagonist activities of the analogues (FIG. 1). This data clearly suggests that pre-incubation of neutrophils with CXCL8$_{(3-74)}$K11R/G31P strongly down-regulates subsequent binding of CXCL8.

In order to more finely map the ability of CXCL8$_{(3-74)}$ K11R/G31 to inhibit the binding of CXCL8, in our next set of experiments we simultaneously exposed the cells to $^{125}$I-CXCL8 and varying doses of $CXCL8_{(3-74)}K11R/G31P$ or unlabeled CXCL8. We found that $CXCL8_{(3-74)}K11R/G31P$ was about two orders of magnitude more effective than wild-type CXCL8 in inhibiting the binding of 20 pM $^{125}$I-CXCL8 to the cells (FIG. 1). The concentration for inhibiting 50% of labeled ligand binding ($IC_{50}$) was 120 pM for unlabelled CXCL8, and 4 pM for $CXCL8_{(3-74)}K11R/G31P$. This data suggests that $CXCL8_{(3-74)}K11R/G31P$ is a very potent competitive inhibitor of CXCL8 binding to neutrophils.

Figure 2:
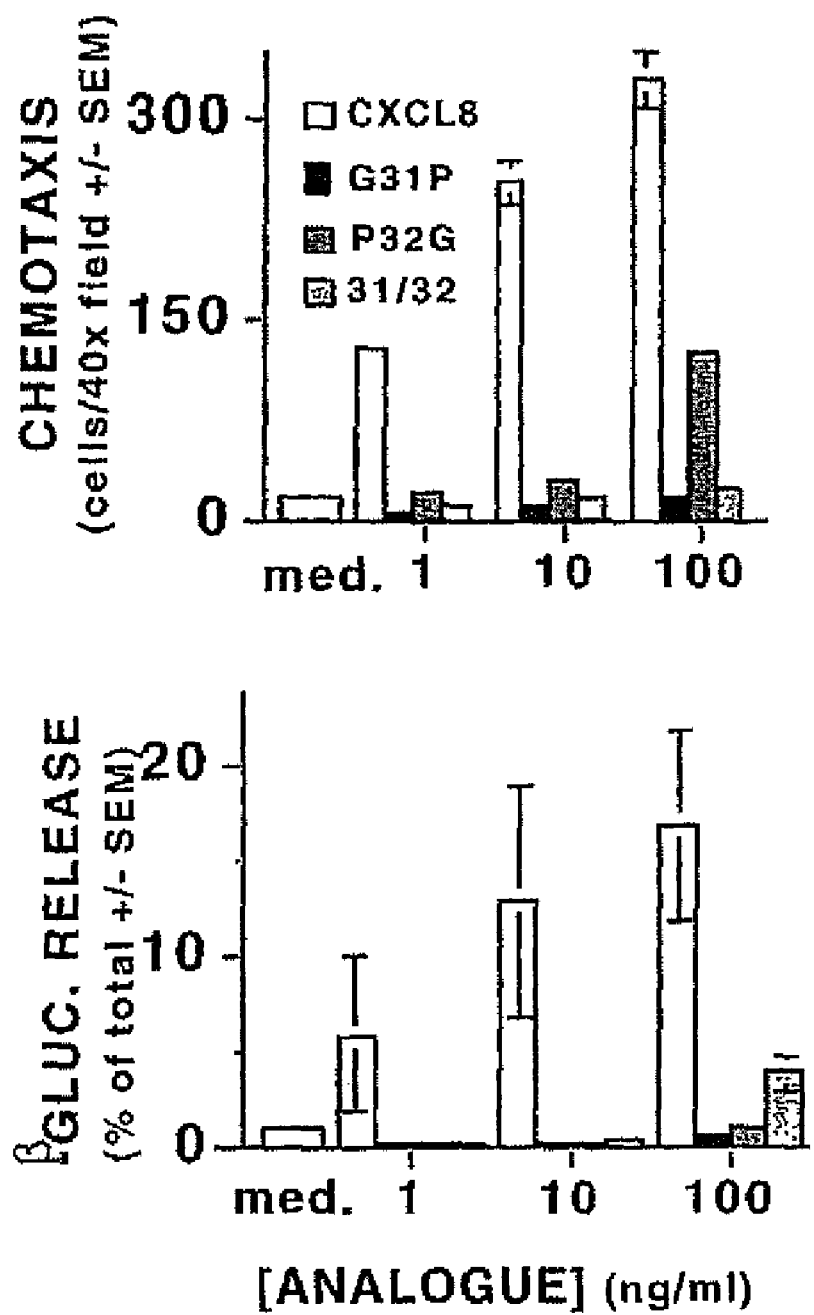
FIG. 2. $CXCL8_{(3-74)}K11R/G31P$ is not an agonist of neutrophil chemoattraction responses or -glucuronidase release. CXCL8 and the G31P, P32G, or combined G31P/P32G analogues of $CXCL8_{(3-74)}K11R$ were tested for their neutrophil agonist activities, using freshly purified bovine peripheral blood neutrophils. (upper panel) The chemotactic responses to each protein were tested in 30 min microchemotaxis assays and the results expressed as the mean (+/−SEM) number of cells/40× objective microscope field, as outlined in the methods section. Both the G31P and G31P/P32G analogues displayed little discernable chemotactic activity, while the P32G analogue stimulated substantial responses at 100 ng/ml. (lower panel) The neutrophils were exposed to varying doses of each analogue for 30 min, then the cellular secretion products were assayed for -glucuronidase using the chromogenic substrate p-nitrophenyl-D-glucuronide, as presented in the methods section. The total cellular stores of -glucuronidase were determined from aliquots of cells lysed with Triton-X-100. The enzyme release with each treatment is expressed as the percent of the total cellular stores. None of the analogues had substantial agonist activity, although CXCL8 itself did induce significant enzyme release. The positive control treatment with phorbol-12,13-myristate acetate and calcium ionophore A23187 induced 42+/−6% enzyme release.

$CXCL8_{(3-74)}K11R/G31P$ does not display neutrophil agonist activities. While $CXCL8_{(3-74)}K11R/G31P$ was certainly a high affinity ligand for the neutrophil CXCL8 receptors, it would equally well do so as an agonist or an antagonist. Thus our next experiments addressed the potential agonist activities of the $CXCL8_{(3-74)}K11R$ analogues we generated, as measured by their abilities to chemo attract these cells or induce release of the neutrophil granule hydrolytic enzyme-glucuronidase in vitro (FIG. 2). We found that even at 100 ng/ml, $CXCL8_{(3-74)}K11R/G31P$ was a poor chemoattractant, inducing 13.9+/−4% or 5.4+/−2% of the responses induced by 1 or 100 ng/ml CXCL8 ($p<0.001$), respectively. At 100 ng/ml, the $CXCL8_{(3-74)}K11R/P32G$ analogue induced a response that was fairly substantial (38.3+/−2% of the CXCL8 response), while the combined $CXCL8_{(3-74)}K11R/G31P/P32G$ analogue also was not an effective chemoattractant. When we assessed their abilities to induce-glucurolnidase release, we found that none of the $CXCL8_{(3-74)}K11R$ analogues was as effective as CXCL8 in inducing mediator release. Indeed, we found only background release with any of them at 10 ng/ml, and at 100 ng/ml only $CXCL8_{(3-74)}K11R/G31P/P32G$ induced significant neutrophil responses (FIG. 2). Given the combined CXCL8 competitive inhibition and neutrophil agonist data, from this point on we focused our attention on $CXCL8_{(3-74)}K11R/G31P$.

Figure 3:
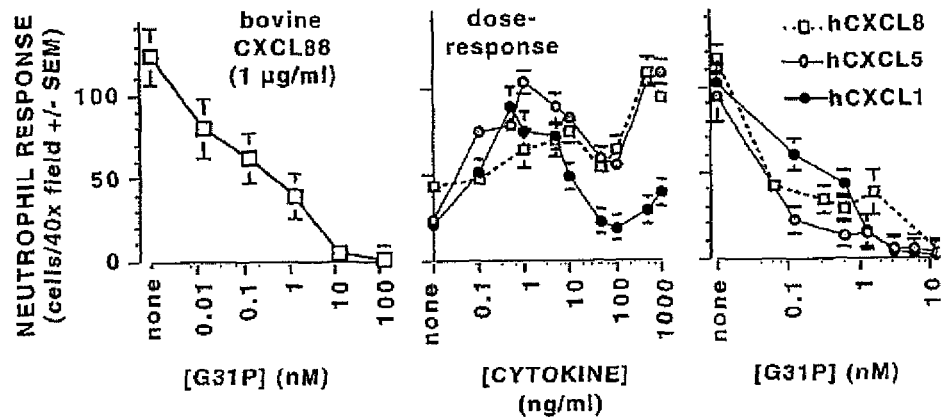
FIG. 3 $CXCL8_{(3-74)}K11R$-G31P is a highly effective antagonist ELR-CXC chemokine-medicated neutrophil chemoattraction. The ability of $CXCL8_{(3-74)}K11R/G31P$ to block chemotactic responses of bovine neutrophils to several ELR-CXC chemokines was measured using 20 min microchemotaxis assays. (left panel) The cells were simultaneously exposed to CXCL8 (1 µg/ml) and varying concentrations of the analogue. The number of cells that responded to the CXCL8 was assessed by direct counting of the chemotaxis assay membranes, as in FIG. 2. $CXCL8_{(3-74)}K11R/G31P$ was a highly effective competitive inhibitor of the cell's responses to CXCL8. (middle panel) Dose-response curves for chemoattraction of bovine neutrophils by human CXCL1, CXCL5, or CXCL8. Each chemokine displayed a biphasic activity pattern, with maxima at 1-10 ng/ml and at 1 µg/ml. (right panel) The ability of $CXCL8_{(3-74)}K11R/G31P$ to block the cell's responses to 1 ng/ml of human CXCL5 or CXCL1 or 10 ng/ml of human CXCL8 was assessed as above. $CXCL8_{(3-74)}K11R/G31P$ effectively antagonized each ELR-CXC chemokine, with complete inhibition being achieved with from 3-20 nM $CXCL8_{(3-74)}K11R/G31P$.

$CXCL8_{(3-74)}K11R/G31P$ blocks neutrophil chemotactic responses to both CXCR1 and CXCR2 ligands. The most pathogenic effect of inappropriate $ELR^+$ chemokine expression is the attraction of inflammatory cells into tissues. Thus, we next assessed the impact of $CXCL8_{(3-74)}K11R/G31P$ on the chemotactic responses of neutrophils to high doses of CXCL8 (FIG. 3). As predicted from our in vivo observations in sheep and cattle (33), 1 µg/ml (129 nM) CXCL8 was very strongly chemoattractive, but even very low doses of $CXCL8_{(3-74)}K11R/G31P$ ameliorated this response. The addition of 12.9 pM $CXCL8_{(3-74)}K11R/G31P$ reduced the chemotactic response of the cells by 33%. The $IC_{50}$ for $CXCL8_{(3-74)}K11R/G31P$ under these conditions was 0.11 nM, while complete blocking of this CXCL8 response was achieved with 10 nM $CXCL8_{(3-74)}K11R/G31P$.

When we tested the efficacy of $CXCL8_{(3-74)}K11R/G31P$ in blocking responses to more subtle bovine CXCL8 challenges, we also extended the study to assess the ability of $CXCLS_{(3-74)}K11R/G31P$ to block neutrophil responses to human CXCL8 as well as to the human CXCR2-specific ligands CXCL1 and CXCL5. Each of these is expressed in the affected tissues of pancreatitis (Hochreiter, W. W. et al. 2000. Urology. 56:1025-1029) or ARDS (Villard et al., 1995) patients at 1-10 ng/ml. We found that bovine neutrophils were responsive to 1 ng/ml hCXCL1 or hCXCL5, and similarly responsive to 10 ng/ml hCXCL8 (FIG. 3), so we employed these doses to test the effects of $CXCL8_{(3-74)}K11R/G31P$ on neutrophil responses of these ligands. The neutrophil responses to hCXCL1 and hCXCL5 were reduced to 50% by 0.26 and 0.06 nM $CXCL8_{(3-74)}K11R/G31P$, respectively, while their responses to hCXCL8 were 50% reduced by 0.04 nM $CXCL8_{(3-74)}K11R/G31P$ (FIG. 3). This data indicates that $CXCL8_{(3-74)}K11R/G31P$ can antagonize the actions of multiple members of the ELR-CXC subfamily of chemokines.

$CXCL8_{(3-74)}K11R/G31P$ is an effective in vitro antagonist of the neutrophil chemokines expressed in bacterial pneumonia or mastitis lesions. We wished to test the extent to which our antagonist could block the array of neutrophil chemoattractants expressed within complex inflammatory environments in vivo. Thus, we chose two diseases in which chemokine-driven neutrophil activation contributes importantly to the progression of the pathology, mastitis and pneumonic mannheimiosis. We utilized an endotoxin model of mastitis (Persson, K. et al., 1993. Vet. Immunol. Immunopathol. 37:99-112), in which we infused 5 µg of endotoxin/teat cistern and 15 h later lavaged each cistern. Neutrophils comprised 82 and 6%, respectively, of the cells from endotoxin and saline-control cisterns, with the bulk of the remaining cells comprising macrophages. The diluted (1:10) wash fluids induced strong in vitro neutrophil chemotactic responses, and the addition of anti-CXCL8 antibodies to the samples maximally reduced these by 73+/−8% (FIG. 4A), relative to the medium control. On the other hand, the addition of 1 ng/ml of $CXCL8_{(3-74)}K11R/G31P$ to the samples reduced their chemotactic activity by 97+/−3%.

Figure 4:
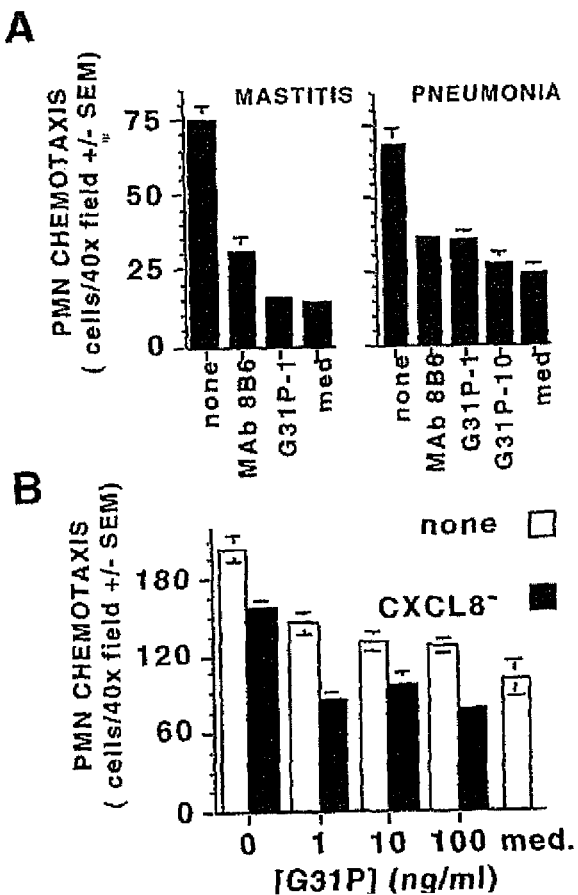
FIG. 4. $CXCL8_{(3-74)}K11R$-G31P blocks the activities of CXCL8 and non-CXCL8 chemoattractants expressed within pneumonic airways or in endotoxin-induced mastitis. The effects of monoclonal anti-IL8 antibody 8B6 or $CXCL8_{(3-74)}K11R$-G31P on neutrophil responses to the chemoattractants expressed within the airways of animals with pneumonic pasteurellosis or in the mammary cisterns of cattle with endotoxin-induced mastitis were assessed as in FIG. 3. (A) Diluted (1:10) bronchoalveolar lavage fluids (BALF) from lesional lung lobes of pneumonic cattle (PNEUMONIA) or teat cistern lavage fluids from cattle with mastitis (MASTITIS) were tested as is (none) or after treatment with either anti-CXCL8 MAb 8B6 (5 µg/ml) or $CXCL8_{(3-74)}K11R/G31P$ (G31P; 1 or 10 ng/ml) for their chemotactic activities compared to medium alone. With both samples, the Mab 8B6 antibodies by themselves neutralized 74% of the chemotactic activities in the samples, while $CXCL8_{(3-74)}K11R/G31P$ reduced the responses by 93-97%. (B) In order to confirm these results using an alternate strategy, we next absorbed lesional BAL fluids with monoclonal antibody 8B6-immunoaffinity matrices, removing >99% of their content of CXCL8, then tested both their residual chemotactic activities and the ability of $CXCL8_{(3-74)}K11R/G31P$ to antagonize these residual non-CXCL8 chemotactic activities. There was a dose-dependent inhibition of the total and residual chemotactic activities in the samples, indicating that both CXCL8 and non-CXCL8 chemoattractants are expressed in these lesions.

Neutrophils also comprised 93+/−12% of the cells recovered from the BALF of cattle with advanced pneumonic mannheimiosis. When tested in vitro, these samples too were strongly chemotactic for neutrophils, and the addition of anti-CXCL8 antibodies maximally reduced their neutrophil chemotactic activities by 73+/−5% (FIG. 4A). Treatment of these BALF samples with 1 or 10 ng/ml of $CXCL8_{(3-74)}K11R/G31P$ reduced the neutrophil responses by 75+/−9 or 93+/−9%, respectively, relative to the medium controls. This data suggests that $CXCL8_{(3-74)}K11R/G31P$ blocks the actions of CXCL8 and non-CXCL8 chemoattractants in these samples.

In order to confirm these observations using an alternate strategy, we next depleted bacterial pneumonia BALF samples of CXCL8 using immunoaffinity matrices, then assessed the efficacy of $CXCL8_{(3-74)}K11R/G31P$ in blocking the residual neutrophil chemotactic activities in the samples (FIG. 4B). The untreated lesional BALF samples contained 3,215+/−275 pg/ml CXCL8, while the immunoaffinity-absorbed BALF contained 24+/−17 pg/ml CXCL8. In this series of experiments the neutrophil response to the CXCL8-depleted BALF samples was 65.4+/−4% of their responses to the unabsorbed samples. It is known that CXCL8 can contribute as little as 15% of the neutrophil chemotactic activities in pneumonic mannheimiosis BALF obtained from an array of clinical cases (Caswell et al., 2001). Whereas the CXCL8 depletion treatments were 99% effective in removing CXCL8, there remained in these samples substantial amounts of neutrophil chemotactic activities, and the addition of 1 ng/ml $CXCL8_{(3-74)}K11R/G31P$ fully abrogated their cumulative effects (FIG. 4B). This data unequivocally confirmed that $CXCL8_{(3-74)}K11R/G31P$ also antagonizes the spectrum of non-IL-8 chemoattractants expressed in these samples.

Figure 5:
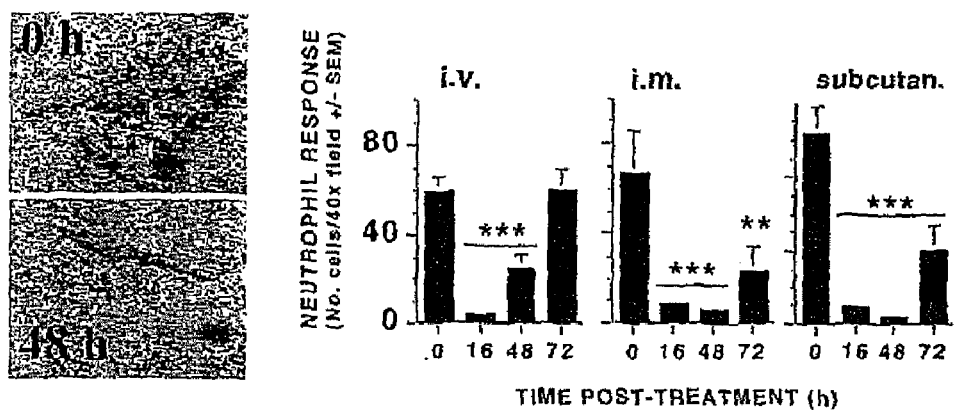
FIG. 5. $CXCL8_{(3-74)}K11R$-G31P can ablate endotoxin-induced inflammatory responses in vivo. Two week-old Holstein calves were tested for their neutrophilic inflammatory responses to intradermal endotoxin (1 µg/site) challenge before and at various time after intravenous (i.v.), subcutaneous (subcutan.), or intramuscular (i.m.) injection of $CXCL8_{(3-74)}K11R$-G31P (75 µg/kg). Fifteen hour endotoxin reaction site biopsies were obtained at 0, 16, 48 and 72 h post-treatment and processed for histopathologic assessment of the neutrophil response, as determined by counting the numbers of neutrophils in nine 40× objective microscope fields per section. (left panel) Photomicrographs of the tissue responses to endotoxin challenge around blood vessels within the reticular dermis prior to (0 h) and 48 h post-treatment. Large numbers of neutrophils accumulated around the vasculature within the reticular dermis in the pre-, but not post-treatment tissues. (B) Graphic presentation of the neutrophil responses to endotoxin challenge either before (0 h) or after (16, 48, 72 h) $CXCL8_{(3-74)}K11R$-G31P delivery by each route.  or *=p 0.01 or 0.001, respectively, relative to the internal control pretreatment responses.

$CXCL8_{(3-74)}K11R/G31P$ is highly efficacious in blocking endotoxin-induced neutrophilic inflammation in vivo. In our last experiments, we assessed the ability of $CXCL8_{(3-74)}K11R/G31P$ to block endotoxin-induced inflammatory responses in the skin of cattle, as well as the time-frames over which it was effective. The animals were challenged intradermally with 1 µg bacterial endotoxin 15 h before (internal positive control response), or at three different times after, intravenous, subcutaneous or intramuscular injection of $CXCLS_{(3-74)}K11R/G31P$ (75 µg/kg). Thus, punch biopsies of 15 h endotoxin reaction sites were taken 15 min before treatment and at 16, 48 and 72 h after injection of the antagonist into each animal, and the numbers of infiltrating neutrophils were determined in a blinded fashion for the papillary (superficial), intermediate and reticular dermis of each biopsy. Prior to the antagonist treatments, strong neutrophilic inflammatory responses were evident at the endotoxin challenge sites in each animal (FIG. 5). Within the biopsies, the responses in the papillary dermis were mild in all animals (data not shown) and became progressively more marked with increasing skin depth, such that maximal inflammation (neutrophil infiltration) was observed around the blood vessels in the reticular dermis (FIG. 5A). Following the $CXCL8_{(3-74)}K11R/G31P$ treatments, the inflammatory responses observed within the 16 h biopsies were 88-93% suppressed, while those in the 48 h biopsies were 57% (intravenous) to 97% (intradermal) suppressed, relative to their respective pretreatment responses. By 72 h post-treatment the effects of the intravenously administered antagonist had worn off, while the endotoxin responses in the intradermally and subcutaneously treated cattle were still 60% suppressed. This data clearly indicates that $CXCL8_{(3-74)}K11R/G31P$ is a highly effective antagonist of endotoxin-induced inflammatory responses in vivo, that these effects can last for 2-3 days, and that the route of delivery markedly affects the pharmacokinetics of this novel antagonist.

Figure 6:
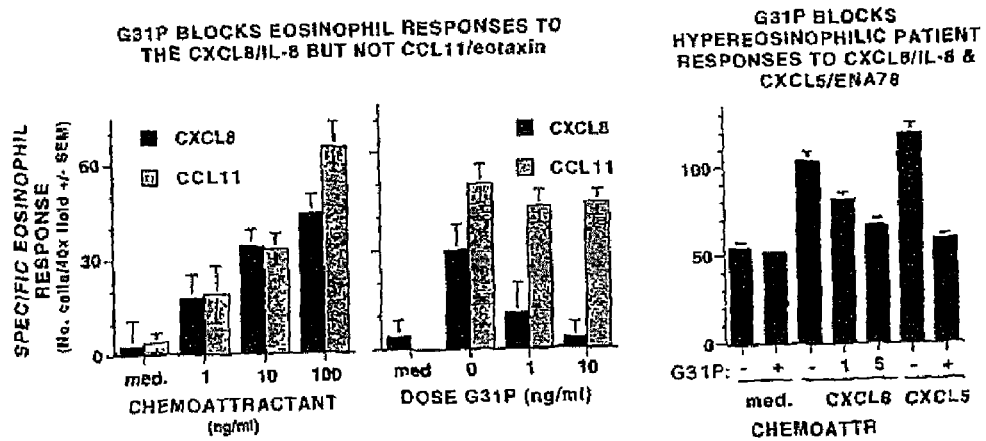
FIG. 6 Eosinophils purified from the blood of atopic asthmatic or atopic non-asthmatic donors (left panels) or a subject with a hypereosinophilia (right panel) were assessed for their responses to recombinant human CXCL8, CXCL5, or CCL11, in the presence or absence of the indicated doses of recombinant bovine $CXCL8_{(3-74)}K11R/G31P$ (G31P). Low doses of G31P were able to block the responses of these cells to each of the CXCR1 and CXCR2 ligands, but had no effect on the eosinophil's responses to the unrelated CCR3 ligand CCL11/eotaxin.

We have found that G31 antagonizes also the chemotactic effects of the human ELR-CXC chemokines CXCL8/IL-8 and CXCL5/ENA-78 on human neutrophils. Thus, the chemotactic activities of 0.1 to 500 ng/ml of either CXCL8 (FIG. 6, left panel) or CXCL5/ENA-78 (FIG. 6, right panel) were essentially completely blocked by the addition of 10 ng/ml of our antagonist to the chemotaxis assays. Similarly, G31P blocked the chemotactic effects of CXCL8 for CXCR1/CXCR2-positive eosinophils. We and others have found that eosinophils from atopic or asthmatic subjects express both ELR-CXC chemokine receptors, and are responsive to CXCL8 (FIG. 7, left panel). The chemotactic effects of 100 ng/ml CXCL8, but not the CCR3 ligand CCL11/eotaxin, on purified peripheral blood eosinophils of an mildly atopic, non-asthmatic donor (99% purity) were completely abrogated by the addition of 10 ng/ml G31P to the chemotaxis assays (FIG. 7, middle panel). When tested against purified eosinophils from a hypereosinophilic patient (FIG. 7, right panel), G31P was neutralized the responses of these cells to either CXCL8/IL-8 or CXCL5/ENA-78.

This data clearly indicates that bovine G31P is an effective antagonist of the bovine ELR-CXC chemokines expressed in vivo in response to endotoxin challenge, but also can fully antagonize neutrophil and eosinophil ELR-CXC chemokine receptor responses to CXCL8 and CXCL5, known ligands for both the CXCR1 and CXCR2.

Humanized bovine G31P.

We generated a bovine-human chaemeric protein, comprising the amino terminal half of bovine G31P and the carboxy terminal half of human CXCL8 (bhG31P) (SEQ ID No. 10), and found that it has strong neutrophil antagonist activity in vitro and in vivo; indeed, bhG31P may have greater activity than bG31P, or the human forms of G31P. We also generated and characterized 5 alternate forms of bhG31P (SEQ ID No. 26-30) in which human amino acids were substituted for the remaining bovine amino acids—none of these augmented the antagonist activity of the analogues, and some evidence suggests that they may reduce the antagonist activity As one approach in generating a human drug, we undertook the humanization of bG31P. Furthermore, since the amino terminal 'half' of CXCL8 is more important for CXCL8's biological activity than the carboxy end, and because the carboxy terminal 'half' of CXCL8 contains 10 of the molecule's 15 bovine-human discrepant amino acids, we first examined whether wholesale ligation of the carboxy end of hCXCL8 (i.e., encoding amino acids 45-72) onto the amino half of bG31P (i.e., encoding amino acids 3-44) would affect its activity. Specifically, the amino half of CXCL8 is known to carry the critical receptor recognition and signalling motifs and their associated scaffolding structures.

We thus generated the chaemeric bovine-human G31P protein, $bCXCL8(3-44)K11R/G31P-hCXCL8_{(45-72)}$ (bhG31P) (SEQ ID No. 10), then used the cDNA for this protein as a template for substitution of the remaining bovine-humandiscrepant amino acid residues one-by-one, as discussed above.

We expressed and purified each construct using SOP for enterokinase ($bhG31P^{+0}$ & $bhG31P^{-1}$ isoforms only) or thrombin (all other analogues) cleavage, and characterized them by SDS-PAGE and Western blotting (FIG. 8). Each isoform was ≈8 kD in size, although the bhG31P/T15K (SEQ ID No. 28) and bhG31P/S37T (SEQ ID No. 30) isoform solutions appeared to contain what could be interpreted as low levels of analogue dimers, formed perhaps as a result of high concentrations of protein in the samples or alternately perhaps related to perturbation of those portions of these G31P analogues associated with dimerization. Several amino acids in this region have been reported previously to significantly affect dimerization of human CXCL8.

We found that bhG31P (i.e., $bCXCL8_{(3-44)}K11R/G31P-hCXCL8_{(45-72)}$) retained the ELR-CXC chemokine antagonist activity of bG31P, such that it blocked the chemotactic or reactive oxygen intermediate (ROI) release responses of human neutrophils to human CXCL8 (FIG. 9).

When we further humanized this bovine-human chaemeric protein by introducing additional human-equivalent amino acids in place of the discrepant residues (i.e., T3K (SEQ ID No. 26), H13Y (SEQ ID No. 27), T15K (SEQ ID No. 28), E35A (SEQ ID No. 29), and S37T (SEQ ID No. 30)), we found that these changes really had no significant effect on the activity of the 50:50 bh chaemera, neither rendering any of the analogues agonistic for neutrophils as assessed in chemotaxis assays (FIG. 10A) or in terms of significantly reducing the antagonistic activity as assessed by chemotaxis inhibition or by inhibition of reactive oxygen intermediate release (FIG. 10B).

As noted, we assessed the impact on the activity of bhG31P of varying the amino terminal sequence (i.e., $bhG31P^{+6}$, $bhG31P^{+2}$, $bhG31P^{+0}$, $bhG31P^{-1}$) (SEQ ID Nos. 14, 13, 11 and 12 respectively), measuring the activity of each in chemotaxis inhibition and reactive oxygen intermediate inhibition assays (FIG. 11). While we found that eliminating Lys3 tended to reduce the activity of bhG31P, the antagonist activities of the other analogues were roughly equivalent (FIG. 11). As will be appreciated by one of skill in the art, this data indicates that N-terminal additions of varying length and varying amino acid composition would be tolerated without significant disruption of G31P activity. Accordingly, N-terminal additions of 0-10 random amino acids or 0-9 random amino acids or 0-8 random amino acids or 0-7 random amino acids or 0-6 random amino acids or 0-5 random amino acids or 0-4 random amino acids or 0-3 random amino acids or 0-2 random amino acids.

Taken together, this data suggests that multiple bovine-humanchaemeric forms of G31P are serviceable neutrophil antagonists. It should be noted however, that at about the time we were completing the characterization of these chaemeras, we determined that human forms of CXCL8(3-72)K11R/G31P were as effective as bG31P in blocking CXCL8-driven neutrophil responses, and that hG31P was also a highly effective antagonist of bacterial endotoxin-driven neutrophil inflammation and pathology in vivo. Thus, at this point in time we moved most of our efforts to more fully characterizing our hG31P constructs.

3. Human G31P.

We contracted with Takara Biotechnology Co., Dalian, PRC to synthesize a fill-length human CXCL8 cDNA, which we cloned into pGEX-2T using compatible 5' (BamH1) and 3' (EcoR1) ends. This pGEX-hCXCL8 cDNA was used as a template for site-directed mutagenesis to generate pGEX-hCXCL8$_{(3-72)}$K11R (hK11R) and pGEX-hCXCL8$_{(3-72)}$ K11R/G31P (hG31P), which were expressed as OST fusion proteins and purified by thrombin cleavage using standard operating procedures. As with bhG31P (above), we generated two families of recombinant G31P-related molecules that were preceded by either six (Gly-Ser-Met-Gly-Gly-Ser) or two (Gly-Ser) extraneous amino acids, referred to as hG31P$^{+6}$ (SEQ ID No. 14) or hG31P$^{+2}$ (SEQ ID No. 13), but also additional families of constructs with no exogenous amino acids (G31P$^{+0}$)) (SEQ ID No. 11) or that were further amino terminal-deleted (i.e., G31P$^{-1}$, G31P$^{-3}$, or G31P$^{-5}$). We also introduced into hG31P$^{+6}$ the bovine equivalent amino acids at amino acid positions 35 (SEQ ID No. 36), 37 (SEQ ID No. 37), 44 (SEQ ID No. 38), 47 (SEQ ID No. 39) and 49 (SEQ ID No. 40). Each protein was expressed, purified and characterized by SDS-PAGE and Western blotting. As predicted, each comprised a single band of ~8 kD that was reactive with anti-CXCL8 antibodies.

Biological characterization of the CXCL8 analogues. We used chemotaxis assays with purified human neutrophils to assess the agonist and CXCL8 antagonist activities of each construct (FIG. 12).

hCXCL8$_{(3-72)}$K11R (hK11R)-hK11R had significantly higher specific activity (neutrophil chemotaxis assays) than human CXCL8, such that it represents a much stronger neutrophil agonist than the native human chemokine. Thus, hK11R could be used in clinical situations calling for augmented neutrophil recruitment/activation.

hCXCL8$_{(3-72)}$K11R/G31P (hG31P)-G31P substitution within hK11R$^{+6}$ essentially eliminated the agonist activity of this molecule, such that hG31P$^{+6}$ was at least as effective an antagonist of CXCL8-driven neutrophil chemotaxis as bG31P$^{+6}$.

The various N-terminal structures of hG31P did affect the biological activity of the analogues, such that hG31P$^{+6}$ and hG31P$^{+2}$ appeared to be superior antagonists of CXCL8 chemotaxis, while hG31P$^{+0}$ and hG31P$^{+2}$ possessed significantly less chemotaxis antagonist activity relative to bG31P$^{+6}$ Interestingly, when compared for their abilities to inhibit CXCL1-induced ROI release from human neutrophils, the various N-terminal sequences had much less effect on the analogue's antagonist activities, with each analogue displaying highly significant ROI release antagonist activity. ROI release is dependent on the activity of NADPH oxidase in neutrophils, and it has been reported that NADPH oxidase is under the control of the CXCR2, but not the CXCR1.

The rationale for the different degrees of effectiveness of these various N-terminal substitution analogues may be that the extra two or six residues on hG31P$^{+2}$ or hG31P$^{+6}$ may further reduce the potential for the ELR motif (i.e. on G31P) interaction with the CXCR1/CXCR2, perhaps by steric hinderance.

In order to further document the abilities of hG31P to antagonize CXCR2 functions, we assessed its abilities to inhibit CXCL5 (ENA-78)-dependent neutrophil chemotaxis; CXCL5 is a CXCR2-, but not CXCR1-, specific ligand. hG31P$^{+6}$ antagonized its chemotactic activity in a dose-dependent fashion (FIG. 14).

We also assessed whether the various N-terminal analogues of hG31P possessed significant agonist activity, relative to PBS alone in a neutrophil chemotaxis assay. We found no significant responses on the part of the neutrophils to any of the alternate N-terminal analogues.

We next assessed whether additional substitutions within hG31P$^{+6}$ of the human-bovine discrepant amino acids would augment this hG31P's antagonist activity. We generated and tested hG31P/A35E, hG31P/M49V, hG31P/R47D, hG31P/S44T and hG331P/T37S and found that all were ineffective agonists. Introduction of bovine-equivalent amino acids into positions 35, 37, 44, 47 or 49 differentially reduced the antagonist activity of these analogues, such that the R47D and S44T analogues seemed to augment the activity of CXCL8, rather than inhibiting it, while the A35E, L49V and T37S analogues displayed no significant chemotaxis inhibition activity.

We previously documented that bG31P could antagonize the neutrophil chemotactic activities present in sputum from cystic fibrosis (CF) patients undergoing bacterial exacerbations of pneumonia. Thus, we tested the ability of hG31P to block the neutrophil chemotactic activities present in sputum from patients with mild (n=1), moderate (n=2), severe (n=2), or advanced (n=2) CF, but also from patients with unclassified (n=2; bact), moderate (n=2), or severe (n=2) bronchiectasis. Sputa from patients diagnosed with asthma, COPD, or general sinusitis/bronchitis were also run with or without hG31P$^{+6}$. With the exception of the one control asthma patient, all others were culture-positive for various bacterial species (e.g., Haemophilus, Pseudonmonas, Staphylococcus). Each sample was titrated in preliminary experiments to determine the optimal dilution for use in the chemotaxis assay. G31P was effective to markedly effective in blocking the neutrophil chemotactic activities present in all samples, except those from the advanced CF patients. This suggests that an alternative etiology may exist for the pathology observed in advanced CF patients.

hG31P Anatgonizes Neutrophil Inflammation In Vivo

We previously documented the ability of bG31P to block endotoxin-induced dermal neutrophilic inflammation and airway endotoxemia pathology. Thus, we next assessed the activity of hG31P in models of airway endotoxemia.

Mouse Model of Airway Endotoxemia

Inasmuch as mice are small animals and this would require substantially less G31P than guinea pigs (our standard model), we first tested the protective effects of hG31P$^{+6}$ on neutrophilic inflammation in mice. In preliminary tests we determined that a LPS dose of 1.5 mg/kg provided an appropriate challenge dose for BALB/c mice; this is in stark contrast to guinea pigs, wherein 5 µg/kg of LPS induces a strong airway neutrophilia, pyrexia, and a pulmonary pleural hemorrhagic response. In a single mouse experiment (n=5/group), mice were given saline or 100, 250, or 500 µg/kg hG31P$^{+6}$ s.c., then one hour later they were challenged intranasally, under light isofluorane gas anesthesia, with LPS (1/5 mg/kg). After 16 hours, the animals were euthanized using $CO_2$, then blood, bronchial alveolar lavage (BAL) fluid, and lung tissues were taken for analysis. While a previous pilot trial had shown that 150 µg/kg of bG31P had little effect in a LPS peritonitis model, hG31P$^{+6}$ was highly effective in reducing airway total white blood cell and neutrophil infiltration, pulmonary parenchyymal neutrophilia and, to a lesser and variable extent, also the appearance of red blood cells in the airways (FIG. 17).

Guinea Pig Model of Airway Endotoxemia

We also employed a guinea pig model of airway endotoxemia in three experiments. In one, the animals were given a supr-optimal dose of endotoxin (50 µg/kg), while in the second and third they were challenged with the standard LPS dose of 5 µg/kg, but with G31P delivered at varying levels. In each experiment, the animals were challenged intranasally with LPS and treated s.c. at the same time with G31P. Fifteen hours later the animals were sacrificed and their peripheral blood (WBC differentials) and pulmonary response (BAL WBC numbers, differentials, and neutrophil degranulation product levels, and tissue neutrophilia) were assessed, as above.

High (Morbid) Dose LPS Challenge Experiment

At doses of $\geq 50$ μg/kg, LPS causes severe pulmonary damage in guinea pigs, including severe bleeding into the airways, although at these doses neutrophil infiltration of the lungs is blunted, relative to that observed with +/−-5 μg/kg LPS. We found that even with 50 μg/kg LPS challenge, hG31P$^{+6}$ was very effective in reducing the appearance of red blood cell (RBC) in the airway (FIG. 18). The G31P treatment also reduced the mean numbers of neutrophils in the BAL.

Efficacy of hG31P and hbG31P in Airway Endotoxemia Pathology

We compared the relative therapeutic efficacy of hG31P$^{+0}$, hG31P$^{-1}$, hG31P$^{+2}$, and hG31P$^{+6}$, as well as the bovine-human chaemera bhG31P$^{+6}$, which had appeared to be highly effective in vitro against human CXCL8 dependent neutrophil recruitment. Again, we delivered 250 μg/kg of each G31P isoform to groups of guinea pigs (s.c.; n=5), and challenged them via airway with 5 μg/kg E. coli LPS, then 15 h later euthanized the animals and assessed their peripheral blood neutrophilia, and airway neutrophil and red blood cell levels, as well as the levels of two nuetrophil granule markers, lactoferrin (a neutrophil 1$^\circ$ granule-specific marker) and myeloperoxidase (a neutrophil 2$^\circ$ granule-specific marker). At this dose of 250 μg/kg, each of the G31P isoforms tested essentially ablated the infiltration of neutrophils into the airways (BAL neutrophils), and significantly decreased the appearance of RBC, lactoferrin and myeloperoxidase in the BAL (FIG. 19). It appeared as if hG31P$^{+2}$ may have given greater protection than the others, but not significantly so when all parameters are taken into account. The bhG31P chaemera was also highly effective in this system in terms of each of the parameters assessed.

Toxicology Tests.

synopsis: Preliminary testing of bG31P toxicity has been performed. Delivery of bG31P (250 μg/kg) to three guinea pigs in a time-frame designed to optimize immune sensitization (i.e., if the molecule were an immunogen) did not cause any observable fluctuations from normal in the serum levels of a panel of liver and kidney enzymes. No changes in animal behavior or overall health were observed. Furthermore, preliminary histologic assessments of heart, kidney, lung, liver, gut, and from these animals revealed no evidence of inflammatory infiltrates, or local cell apoptosis or proliferation, or histopathologic abnormalities. We are making arrangements for an anatomic pathologist to independently assess these tissues. We were not able to detect discernible levels of anti-bG31P antibody reactivity in the serum of these animals, although the assays employed are not particularly sensitive.

Of importance to the generation of hG31P or bG31P using a prokaryotic (i.e., bacterial) expression system, we found that the preparations are significantly contaminated with bacterial endotoxin. When passed over commercial endotoxin-removal columns to reduce the endotoxin load of the drug, we found that the use of the endotoxin-removal columns resulted in unacceptably high loss of G31P. In vivo, treatment of guinea pigs with the levels of endotoxin found in therapeutic doses of G31P did not mimic the therapeutic activity of G31P.

Efficacy Studies.

In one experiment we employed hG31P+6 at 50 μg/kg (i.e., 20% of the optimal dose for bG31P). Guinea pigs were challenged with 5 μg/kg of LPS and treated with this low dose of hG31P. We found that hG31P+2 and hG31P+6 retained only modest efficacy in terms of reducing neutrophil infiltration, but was still effective in reducing red blood cell migration into the airways (the meaning of this finding is not entirely clear, but they suggest the potential for yet another degree of complexity in the mechanisms by which this drug acts).

In another in vivo approach using the airway endotoxemia model, we challenged guinea pigs with a dose of LPS known to induce severe pulmonary hemorrhage, and treated them with 250 μg/kg hG31P. We knew from previous studies that at this elevated dose of LPS neutrophils are only poorly recruited from the vasculature into the airways . . . .

In one experiment we employed hG31P$^{+6}$ at 50 μg/kg (i.e., 20% of the optimal dose for bG31P). Guinea pigs were challenged with 5 μg/kg of LPS and treated with this low dose of hG31P. We found that hG31P$^{+2}$ and hG31P$^{+6}$ retained only modest efficacy in terms of reducing neutrophil infiltration, but was still effective in reducing red blood cell migration into the airways (the meaning of this finding is not entirely clear, but they suggest the potential for yet another degree of complexity in the mechanisms by which this drug acts).

In another in vivo approach using the airway endotoxemia model, we challenged guinea pigs with 50 μg/kg of LPS, a dose known to induce severe pulmonary hemorrhage, and treated them with 250 μg/kg hG31P (see FIG. 18). We knew from previous studies that at this elevated dose of LPS neutrophils are only poorly recruited from the vasculature into the airways. Nevertheless, hG31P did have significant effects on reducing the high level of extravasation of RBC into the airway observed in saline-treated, high dose LPS-challenged animals (FIG. 18), and tended to reduce the airway neutrophil response and peripheral blood neutrophil mobilization associated with this challenge (FIG. 18).

Discussion

We demonstrated herein that CXCL8$_{(3-74)}$K11R/G31P is a high affinity antagonist of multiple ELR-CXC chemokines. In vitro, this antagonist effectively blocked all of the neutrophil chemotactic activities expressed in mild to intense inflammatory lesions within two mucosal compartments (lungs, mammary glands), and up to 97% blocked endotoxin-induced inflammatory responses in vivo. We identified CXCL8 as a major chemoattractant in the pneumonia and mastitis samples, but also demonstrated that 35% of the activity in the bacterial pneumonia samples was due to non-CXCL8 chemoattractants that were also effectively antagonized by CXCL8$_{(3-74)}$K11R/G31P. Based on studies of inflammatory responses in rodents (Tateda et al., 2001; Tsai et al., 2000), cattle (Caswell et al., 1997), and humans (Villard et al., 1995), it is clear that these samples could contain numerous ELR$^+$ CXC chemokines (e.g., CXCL5, and CXCL8) to which CXCL8$_{(3-74)}$K11R/G31P has an antagonistic effect.

REFERENCES

1. Baggiolini, M. 1998. Chemokines and leukocyte traffic. Nature. 392:565-568.
2. Sekido, N., N. Mukaida, A. Harada, I. Nakanishi, Y. Watanabe, and K. Matsushima. 1993. Prevention of lung reperfusion injury in rabbits by a monoclonal antibody against interleukin-8. Nature. 365:654-657.
3. Villard, J., F. Dayer Pastore, J. Hamacher, J. D. Aubert, S. Schlegel Haueter, and L. P. Nicod. 1995. GRO alpha and interleukin-8 in *Pneumocystis carinii* or bacterial pneumonia and adult respiratory distress syndrome. Am. J. Respir. Crit. Care Med. 152:1549-1554.

4. Mukaida, N., T. Matsumoto, K. Yokoi, A. Harada, and K. Matsushima. 1998. Inhibition of neutrophil-mediated acute inflammation injury by an antibody against interleukin-8 (IL-8). Inflamm. Res. 47 (suppl. 3):S151-157.

5. Harada, A., N. Mukaida, and K. Matsushima. 1996. Interleukin 8 as a novel target for intervention therapy in acute inflammatory diseases. Inflamm. Res. 2:482-489.

6. Walley, K. R., N. W. Lukacs, T. J. Standiford, R. M. Strieter, and S. L. Kunkel. 1997. Elevated levels of macrophage inflammatory protein 2 in severe murine peritonitis increase neutrophil recruitment and mortality. Infect. Immun. 65:3847-3851.

7. Slocombe, R., J. Malark, R. Ingersoll, F. Derksen, and N. Robinson. 1985. Importance of neutrophils in the pathogenesis of acute pneumonic pasteurellosis in calves. Am. J. Vet. Res. 46:2253.

8. Caswell, J. L., D. M. Middleton, S. D. Sorden, and J. R. Gordon. 1997. Expression of the neutrophil chemoattractant interleukin-8 in the lesions of bovine pneumonic pasteurellosis. Vet. Pathol. 35:124-131.

9. Caswell, J. L., D. M. Middleton, and J. R. Gordon. 2001. The importance of interleukin-8 as a neutrophil chemoattractant in the lungs of cattle with pneumonic pasteurellosis. Canad. J. Vet. Res. 65:229-232.

10. Baggiolini, M., and B. Moser. 1997. Blocking chemokine receptors. J. Exp. Med. 186:1189-1191.

11. Ahuja, S. K., and P. M. Murphy. 1996. The CXC chemokines growth-regulated oncogene (GPO) alpha, GRObeta, GROgamma, neutrophil-activating peptide-2, and epithelial cell derived neutrophil-activating peptide-78 are potent agonists for the type B, but not the type A, human interleukin-8 receptor. J. Biol. Chem. 271:20545-20550.

12. Loetscher, P., M. Seitz, I. Clark Lewis, M. Baggiolini, and B. Moser. 1994. Both interleukin-8 receptors independently mediate chemotaxis. Jurkat cells transfected with IL-8R1 or IL-8R2 migrate in response to IL-8, GRO alpha and NAP-2. FEBS Lett. 341:187-192.

13. Wuyts, A., P. Proost, J. P. Lenaerts, A. Ben Baruch, J. Van Damme, and J. M. Wang. 1998. Differential usage of the CXC chemokine receptors 1 and 2 by interleukin-8, granulocyte chemotactic protein-2 and epithelial-cell-derived neutrophil attractant-78. Eur. J. Biochem. 255:67-73.

14. Richardson, R., B. Pridgen, B. Haribabu, H. All, and R. Snyderman. 1998. Differential cross-regulation of the human chemokine receptors CXCR1 and CXCR2. Evidence for time-dependent signal generation. J. Biol. Chem. 273:23830-23836.

15. McColl, S. R., and 1. Clark Lewis. 1999. Inhibition of murine neutrophil recruitment in vivo by CXC chemokine receptor antagonists. J. Immunol. 163:2829-2835.

16. Jones, S. A., M. Wolf, S. Qin, C. R. Mackay, and M. Baggiolini. 1996. Different functions for the interleukin 8 receptors (IL-8R) of human neutrophil leukocytes: NADPH oxidase and phospholipase D are activated through IL-8R1 but not IL-8R2. Proc. Natl. Acad. Sci. U.S.A. 93:6682-6686.

17. White, J. R., J. M. Lee, P. R. Young, R. P. Hertzberg, A. J. Jurewicz, M. A. Chaikin, K. Widdowson, J. J. Foley, L. D. Martin, D. E. Griswold, and H. M. Sarau. 1998. Identification of a potent, selective non-peptide CXCR2 antagonist that inhibits interleukin-8-induced neutrophil migration. J. Biol. Chem. 273:10095-10098.

18. Tateda, K., T. A. Moore, M. W. Newstead, W. C. Tsai, X. Zeng, J. C. Deng, G. Chen, R. Reddy, K. Yamaguchi, and T. J. Standiford. 2001. Chemokine-dependent neutrophil recruitment in a murine model of Legionella pneumonia: potential role of neutrophils as immunoregulatory cells. Infect. Immun. 69:2017-2024.

19. Tsai, W. C., R. M. Strieter, B. Mehrad, M. W. Newstead, X. Zeng, and T. J. Standiford. 2000. CXC chemokine receptor CXCR2 is essential for protective innate host response in murine Pseudomonas aeruginosa pneumonia. Infect. Immun. 68:4289-4296.

20. Goodman, R. B., R. M. Strieter, C. W. Frevert, C. J. Cummings, P. Tekamp Olson, S. L. Kunkel, A. Walz, and T. R. Martin. 1998. Quantitative comparison of C-X-C chemokines produced by endotoxin-stimulated human alveolar macrophages. Am. J. Physiol. 275:L87-95.

21. Nufer, O., M. Corbett, and A. Walz. 1999. Amino-terminal processing of chemokine ENA-78 regulates biological activity. Biochem. 38:636-642.

22. Wuyts, A., A. D'Haese, V. Cremers, P. Menten, J. P. Lenaerts, A. De Loof, H. Heremans, P. Proost, and J. Van Damme. 1999. NH2- and COOH- terminal truncations of murine granulocyte chemotactic protein-2 augment the in vitro and in vivo neutrophil chemotactic potency. J. Leukoc. Biol. 163:6155-6163.

23. Clark Lewis, I., B. Dewald, M. Loetscher, B. Moser, and M. Baggiolini. 1994. Structural requirements for interleukin-8 function identified by design of analogs and CXC chemokine hybrids. J. Biol. Chem. 269:16075-16081.

24. Li, F., and J. R. Gordon. 2001. IL-8.sub.(3-74)K11R is a high affinity agonist of the neutrophil CXCR1 and CXCR2. Biochem. Biophys. Res. Comm. 286:595-600.

25. Moser, B., B. Dewald, L. Barella, C. Schumacher, M. Baggiolini, and I. Clark Lewis. 1993. Interleukin-8 antagonists generated by N-terminal modification. J. Biol. Chem. 268:7125-7128.

26. Caswell, J. L., D. M. Middleton, and J. R. Gordon. 1998. Production and functional characterization of recombinant bovine interleukin-8 as a neutrophil-activator and specific chemoattractant in vitro and in vivo. Vet. Immunol. Immunopath. 67:327-340.

27. Coligan, J., A. Kruisbeek, D. Margulies, E. Shevach, and W. Strober. 1994. Current Protocols in Immunology. John Wiley & Sons, New York.

28. Wailer, K. P. 1997. Modulation of endotoxin-induced inflammation in the bovine teat using antagonists/inhibitors to leukotrienes, platelet activating factor and interleukin 1 beta. Vet. Immunol. Immunopathol. 57:239-251.

29. Cairns, C. M., J. R. Gordon, F. Li, M. E. Baca-Estrada, T. N. Moyana, and J. Xiang. 2001. Lymphotactin expression by engineered myeloma tumor cells drives tumor regression. Mediation by CD4+ and CD8+ T cells and neutrophils expressing XCR1 receptors. J. Immunol. 167:57-65.

30. Gordon, J. R. 2000. TGFb and TNFa secretion by mast cells stimulated via the FceRI activates fibroblasts for high level production of monocyte chemoattractant protein-1. Cell Immunol. 201:42-49.

31. Gordon, J. R., and S. J. Galli. 1994. Promotion of mouse fibroblast collagen gene expression by mast cells stimulated via the FceRI. Role for mast cell-derived transforming growth factor-b and tumor necrosis factor-a. J. Exp. Med. 180:2027-2037.

32. Gordon, J. R. 2000. Monocyte chemoattractant protein-1 (MCP-1) expression during cutaneous allergic responses in mice is mast cell-dependent and largely mediates monocyte recruitment. J. Allergy Clin. Immunol. 106:110-116.

33. Caswell, J. L. 1998. The role of interleukin-8 as a neutrophil chemoattractant in bovine bronchopneumonia. Ph.D. thesis, Department of Veterinary Pathology, University of Saskatchewan. 241 pg.
34. Hochreiter, W. W., R. B. Nadler, A. E. Koch, P. L. Campbell, M. Ludwig, W. Weidner, and A. J. Schaeffer. 2000. Evaluation of the cytokines interleukin-8 and epithelial neutrophil activating peptide-78 as indicators of inflammation in prostatic secretions. Urology. 56:1025-1029.
35. Persson, K., I. Larsson, and C. Hallen Sandgren. 1993. Effects of certain inflammatory mediators on bovine neutrophil migration in vivo and in vitro. Vet. Immunol. Immunopathol. 37:99-112.
36. Gray, G. D., K. A. Knight, R. D. Nelson, and M. Herron, J. 1982. Chemotactic requirements of bovine leukocytes. Am. J. Vet. Res. 43:757-759.
37. Fernandez, H. N., P. M. Henson, A. Otani, and T. E. Hugli. 1978. Chemotactic response to human C3a and C5a anaphylatoxins. I. Evaluation of C3a and C5a leukotaxis in vitro and under stimulated in vivo conditions. J. Immunol. 120:109-115.
38. Riollet, C., P. Rainard, and B. Poutrel. 2000. Differential induction of complement fragment C5a and inflammatory cytokines during intramammary infections with *Escherichia coli* and *Staphylococcus aureus*. Clin. Diagn. Lab Immunol. 7:161-167.
39. Shuster, D. E., M. E. Kehrli, Jr., P. Rainard, and M. Paape. 1997. Complement fragment C5a and inflammatory cytokines in neutrophil recruitment during intramammary infection with *Escherichia coli*. Infect. Immun. 65:3286-3292.
40. Bless, N. M., R. L. Warner, V. A. Padgaonkar, A. B. Lentsch, B. J. Czermak, H. Schmal, H. P. Friedl, and P. A. Ward. 1999. Roles for C-X-C chemokines and C5a in lung injury after hindlimb ischemia-reperfusion. Am. J. Physiol. 276:L57-63.
41. Ember, J. A., S. D. Sanderson, T. E. Hugli, and E. L. Morgan. 1994. Induction of interleukin-8 synthesis from monocytes by human C5a anaphylatoxin. Am. J. Pathol. 144:393-403.
42. Fisher, C., G. Slotman, S. Opal, J. Pribble, R. Bone, G. Emmanuel, D. Ng, D. Bloedow, and M. Catalano. 1994. Initial evaluation of human recombinant interleukin-1 receptor antagonist in the treatment of sepsis syndrome: a randomized, open-label, placebocontrolled multicenter trial. The IL-1RA Sepsis Syndrome Study Group. Crit. Care Med. 22:11-21.
43. Verbon, A., P. E. Dekkers, T. ten Hove, C. E. Hack, J. Pribble, T. Turner, S. Souza, T. Axtelle, F. Hoek, -.S. -J. van Deventer, and T, van der Poll. 2001. IC14, an anti-CD 14 antibody, inhibits endotoxin-mediated symptoms and inflammatory responses in humans. J. Immunol. 166:3599-3605.
44. Clark Lewis, I., K. S. Kim, K. Rajarathnam, J. H. Gong, B. Dewald, B. Moser, M. Baggiolini, and B. D. Sykes. 1995. Structure-activity relationships of chemokines. J. Leukoc. Biol. 57:703-711.
45. Jones, S. A., B. Dewald, I. Clark Lewis, and M. Baggiolini. 1997. Chemokine antagonists that discriminate between interleukin-8 receptors. Selective blockers of CXCR2. J. Biol. Chem. 272:16166-16169.
46. Hang, L., B. Frendeus, G. Godaly, and C. Svanborg. 2000. Interleukin-8 receptor knockout mice have subepithelial neutrophil entrapment and renal scarring following acute pyelonephritis. J. Infect. Dis. 182:1738-1748.
47. Saurer, L., P. Reber, T. Schaffner, M. W. Buchler, C. Buri, A. Kappeler, A. Walz, H. Friess, and C. Mueller. 2000. Differential expression of chemokines in normal pancreas and in chronic pancreatitis. Gastroenterol. 118: 356-367.
48. Szekanecz, Z., R. M. Strieter, S. L. Kunkel, and A. E. Koch. 1998. Chemokines in rheumatoid arthritis. Springer Semin. Immunopathol. 20:115-132.
49. MacDermott, R. P. 1999. Chemokines in the inflammatory bowel diseases. J. Clin. Immunol. 19:266-272.
50. Damas, J. K., L. Gullestad, T. Ueland, N, O, Solum, S. Simonsen, S. S. Froland, and P. Aukrust, 2000. CXC-chemokines, a new group of cytokines in congestive heart failure—possible role of platelets and monocytes. Cardiovasc. Res. 45:428-436.
51. Morsey, M., Y. Popowych, J. Kowalski, G. Gerlach, D. Godson, M. Campos, and L. Babiuk. 1996. Molecular cloning and expression of bovine interleukin-8. Microbial Pathogen. 20:203-212.
52. Benson, M., I. L. Strannegard, G. Wennergren, and O, Strannegard. 1999. Interleukin-5 and interleukin-8 in relation to eosinophils and neutrophils in nasal fluids from school children with seasonal allergic rhinitis. Pediatr. Allergy Immunol. 10:178-185.
53. Hauser, U., M. Wagenmann, C. Rudack, and C. Bachert. 1997. Specific immunotherapy suppresses IL-8-levels in nasal secretions: A possible explanation for the inhibition of eosinophil migration. Allergol. 20:184-191.
54. Sehmi, R., O. Cromwell, A. J. Wardlaw, R. Moqbel, and A. B. Kay. 1993. Interleukin-8 is a chemoattractant for eosinophils purified from subjects with a blood eosinophilia but not from normal healthy subjects. Clin. Exp. Allergy 23; 1027-1036.
55. Ulfinan, L. H., D. P. Joosten, J. A. van der Linden, J. W. Lammers, J. J. Zwaginga, and L. Koenderman. 2001. IL-8 induces a transient arrest of rolling eosinophils on human endothelial cells. J. Immunol. 166:588-595.

The invention claimed is:

1. An isolated or purified peptide comprising the amino acid sequence of as set forth in SEQ ID No. 13.

\* \* \* \* \*

SEQUENCE LISTING

<160> NUMBER OF SEQ ID NOS: 43

<210> SEQ ID NO 1
<211> LENGTH: 74
<212> TYPE: PRT
<213> ORGANISM: bovinae

-continued

```
<400> SEQUENCE: 1

Met Ser Thr Glu Leu Arg Cys Gln Cys Ile Lys Thr His Ser Thr Pro
1               5                   10                  15

Phe His Pro Lys Phe Ile Lys Glu Leu Arg Val Ile Glu Ser Gly Pro
            20                  25                  30

His Cys Glu Asn Ser Glu Ile Ile Val Lys Leu Thr Asn Gly Asn Glu
        35                  40                  45

Val Cys Leu Asn Pro Lys Glu Lys Trp Val Gln Lys Val Val Gln Val
    50                  55                  60

Phe Val Lys Arg Ala Glu Lys Gln Asp Pro
65                  70

<210> SEQ ID NO 2
<211> LENGTH: 72
<212> TYPE: PRT
<213> ORGANISM: Homo sapiens

<400> SEQUENCE: 2

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 3
<211> LENGTH: 72
<212> TYPE: PRT
<213> ORGANISM: artificial
<220> FEATURE:
<223> OTHER INFORMATION: synthesized using consensus sequence from
      human, bovine, sheep, pig, dolphin, horse, cat and rhesus monkey
      sequences
<220> FEATURE:
<221> NAME/KEY: MISC_FEATURE
<222> LOCATION: (1)..(1)
<223> OTHER INFORMATION: any
<220> FEATURE:
<221> NAME/KEY: misc_feature
<222> LOCATION: (6)..(6)
<223> OTHER INFORMATION: any
<220> FEATURE:
<221> NAME/KEY: misc_feature
<222> LOCATION: (10)..(10)
<223> OTHER INFORMATION: any
<220> FEATURE:
<221> NAME/KEY: misc_feature
<222> LOCATION: (11)..(11)
<223> OTHER INFORMATION: any
<220> FEATURE:
<221> NAME/KEY: misc_feature
<222> LOCATION: (13)..(13)
<223> OTHER INFORMATION: any
<220> FEATURE:
<221> NAME/KEY: misc_feature
<222> LOCATION: (16)..(16)
<223> OTHER INFORMATION: any
<220> FEATURE:
<221> NAME/KEY: misc_feature
<222> LOCATION: (19)..(19)
<223> OTHER INFORMATION: any
<220> FEATURE:
<221> NAME/KEY: misc_feature
```

```
<222> LOCATION: (21)..(21)
<223> OTHER INFORMATION: any
<220> FEATURE:
<221> NAME/KEY: misc_feature
<222> LOCATION: (23)..(23)
<223> OTHER INFORMATION: any
<220> FEATURE:
<221> NAME/KEY: misc_feature
<222> LOCATION: (24)..(24)
<223> OTHER INFORMATION: any
<220> FEATURE:
<221> NAME/KEY: misc_feature
<222> LOCATION: (25)..(25)
<223> OTHER INFORMATION: any
<220> FEATURE:
<221> NAME/KEY: misc_feature
<222> LOCATION: (27)..(27)
<223> OTHER INFORMATION: any
<220> FEATURE:
<221> NAME/KEY: misc_feature
<222> LOCATION: (33)..(33)
<223> OTHER INFORMATION: any
<220> FEATURE:
<221> NAME/KEY: misc_feature
<222> LOCATION: (35)..(35)
<223> OTHER INFORMATION: any
<220> FEATURE:
<221> NAME/KEY: misc_feature
<222> LOCATION: (42)..(42)
<223> OTHER INFORMATION: any
<220> FEATURE:
<221> NAME/KEY: misc_feature
<222> LOCATION: (43)..(43)
<223> OTHER INFORMATION: any
<220> FEATURE:
<221> NAME/KEY: misc_feature
<222> LOCATION: (45)..(45)
<223> OTHER INFORMATION: any
<220> FEATURE:
<221> NAME/KEY: misc_feature
<222> LOCATION: (47)..(47)
<223> OTHER INFORMATION: any
<220> FEATURE:
<221> NAME/KEY: misc_feature
<222> LOCATION: (50)..(50)
<223> OTHER INFORMATION: any
<220> FEATURE:
<221> NAME/KEY: misc_feature
<222> LOCATION: (52)..(52)
<223> OTHER INFORMATION: any
<220> FEATURE:
<221> NAME/KEY: misc_feature
<222> LOCATION: (53)..(53)
<223> OTHER INFORMATION: any
<220> FEATURE:
<221> NAME/KEY: misc_feature
<222> LOCATION: (54)..(54)
<223> OTHER INFORMATION: any
<220> FEATURE:
<221> NAME/KEY: misc_feature
<222> LOCATION: (58)..(58)
<223> OTHER INFORMATION: any
<220> FEATURE:
<221> NAME/KEY: misc_feature
<222> LOCATION: (59)..(59)
<223> OTHER INFORMATION: any
<220> FEATURE:
<221> NAME/KEY: misc_feature
<222> LOCATION: (61)..(61)
<223> OTHER INFORMATION: any
<220> FEATURE:
<221> NAME/KEY: misc_feature
<222> LOCATION: (62)..(62)
<223> OTHER INFORMATION: any
<220> FEATURE:
<221> NAME/KEY: misc_feature
<222> LOCATION: (64)..(64)
<223> OTHER INFORMATION: any
<220> FEATURE:
```

```
<221> NAME/KEY: misc_feature
<222> LOCATION: (66)..(66)
<223> OTHER INFORMATION: any
<220> FEATURE:
<221> NAME/KEY: misc_feature
<222> LOCATION: (67)..(67)
<223> OTHER INFORMATION: any
<220> FEATURE:
<221> NAME/KEY: misc_feature
<222> LOCATION: (69)..(69)
<223> OTHER INFORMATION: any
<220> FEATURE:
<221> NAME/KEY: misc_feature
<222> LOCATION: (70)..(70)
<223> OTHER INFORMATION: any
<220> FEATURE:
<221> NAME/KEY: misc_feature
<222> LOCATION: (71)..(71)
<223> OTHER INFORMATION: any
<220> FEATURE:
<221> NAME/KEY: misc_feature
<222> LOCATION: (72)..(72)
<223> OTHER INFORMATION: any

<400> SEQUENCE: 3

Xaa Glu Leu Arg Cys Xaa Cys Ile Arg Xaa Xaa Ser Xaa Pro Phe Xaa
 1               5                  10                  15

Pro Lys Xaa Ile Xaa Glu Xaa Xaa Xaa Ile Xaa Ser Pro Pro His Cys
            20                  25                  30

Xaa Asn Xaa Glu Ile Ile Val Lys Leu Xaa Xaa Gly Xaa Glu Xaa Cys
        35                  40                  45

Leu Xaa Pro Xaa Xaa Xaa Trp Val Gln Xaa Xaa Val Xaa Xaa Phe Xaa
    50                  55                  60

Lys Xaa Xaa Glu Xaa Xaa Xaa Xaa
65                  70

<210> SEQ ID NO 4
<211> LENGTH: 72
<212> TYPE: PRT
<213> ORGANISM: artificial
<220> FEATURE:
<223> OTHER INFORMATION: synthesized using consensus sequence from
      human, bovine, sheep, pig, dolphin, horse, cat and rhesus monkey
      sequences
<220> FEATURE:
<221> NAME/KEY: MISC_FEATURE
<222> LOCATION: (1)..(1)
<223> OTHER INFORMATION: 0-10 amino acids
<220> FEATURE:
<221> NAME/KEY: MISC_FEATURE
<222> LOCATION: (6)..(6)
<223> OTHER INFORMATION: q, e or l
<220> FEATURE:
<221> NAME/KEY: MISC_FEATURE
<222> LOCATION: (10)..(10)
<223> OTHER INFORMATION: t or i
<220> FEATURE:
<221> NAME/KEY: MISC_FEATURE
<222> LOCATION: (11)..(11)
<223> OTHER INFORMATION: h or y
<220> FEATURE:
<221> NAME/KEY: MISC_FEATURE
<222> LOCATION: (13)..(13)
<223> OTHER INFORMATION: t or k
<220> FEATURE:
<221> NAME/KEY: MISC_FEATURE
<222> LOCATION: (16)..(16)
<223> OTHER INFORMATION: h or n
<220> FEATURE:
<221> NAME/KEY: MISC_FEATURE
<222> LOCATION: (19)..(19)
<223> OTHER INFORMATION: f, y or l
<220> FEATURE:
```

```
<221> NAME/KEY: misc_feature
<222> LOCATION: (21)..(21)
<223> OTHER INFORMATION: Xaa can be any naturally occurring amino acid
<220> FEATURE:
<221> NAME/KEY: MISC_FEATURE
<222> LOCATION: (23)..(23)
<223> OTHER INFORMATION: l or m
<220> FEATURE:
<221> NAME/KEY: MISC_FEATURE
<222> LOCATION: (24)..(24)
<223> OTHER INFORMATION: r or t
<220> FEATURE:
<221> NAME/KEY: MISC_FEATURE
<222> LOCATION: (25)..(25)
<223> OTHER INFORMATION: v or a
<220> FEATURE:
<221> NAME/KEY: MISC_FEATURE
<222> LOCATION: (27)..(27)
<223> OTHER INFORMATION: d or e
<220> FEATURE:
<221> NAME/KEY: MISC_FEATURE
<222> LOCATION: (33)..(33)
<223> OTHER INFORMATION: v, a or e
<220> FEATURE:
<221> NAME/KEY: MISC_FEATURE
<222> LOCATION: (35)..(35)
<223> OTHER INFORMATION: t or s
<220> FEATURE:
<221> NAME/KEY: MISC_FEATURE
<222> LOCATION: (42)..(42)
<223> OTHER INFORMATION: s, v, t or f
<220> FEATURE:
<221> NAME/KEY: MISC_FEATURE
<222> LOCATION: (43)..(43)
<223> OTHER INFORMATION: d or n
<220> FEATURE:
<221> NAME/KEY: MISC_FEATURE
<222> LOCATION: (45)..(45)
<223> OTHER INFORMATION: r, a, n or k
<220> FEATURE:
<221> NAME/KEY: MISC_FEATURE
<222> LOCATION: (47)..(47)
<223> OTHER INFORMATION: l or v
<220> FEATURE:
<221> NAME/KEY: MISC_FEATURE
<222> LOCATION: (50)..(50)
<223> OTHER INFORMATION: d or n
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: MISC_FEATURE
<222> LOCATION: (53)..(53)
<223> OTHER INFORMATION: e, q or t
<220> FEATURE:
<221> NAME/KEY: MISC_FEATURE
<222> LOCATION: (54)..(54)
<223> OTHER INFORMATION: p, n or k
<220> FEATURE:
<221> NAME/KEY: MISC_FEATURE
<222> LOCATION: (58)..(58)
<223> OTHER INFORMATION: r, k or i
<220> FEATURE:
<221> NAME/KEY: MISC_FEATURE
<222> LOCATION: (59)..(59)
<223> OTHER INFORMATION: v or i
<220> FEATURE:
<221> NAME/KEY: MISC_FEATURE
<222> LOCATION: (61)..(61)
<223> OTHER INFORMATION: e or q
<220> FEATURE:
<221> NAME/KEY: MISC_FEATURE
<222> LOCATION: (62)..(62)
<223> OTHER INFORMATION: k, i, v or a
<220> FEATURE:
<221> NAME/KEY: MISC_FEATURE
<222> LOCATION: (64)..(64)
<223> OTHER INFORMATION: l or v
```

```
<220> FEATURE:
<221> NAME/KEY: MISC_FEATURE
<222> LOCATION: (66)..(66)
<223> OTHER INFORMATION: r or k
<220> FEATURE:
<221> NAME/KEY: MISC_FEATURE
<222> LOCATION: (67)..(67)
<223> OTHER INFORMATION: a or t
<220> FEATURE:
<221> NAME/KEY: MISC_FEATURE
<222> LOCATION: (69)..(69)
<223> OTHER INFORMATION: s, n, k or g
<220> FEATURE:
<221> NAME/KEY: MISC_FEATURE
<222> LOCATION: (70)..(70)
<223> OTHER INFORMATION: q, s, k or deleted
<220> FEATURE:
<221> NAME/KEY: MISC_FEATURE
<222> LOCATION: (71)..(71)
<223> OTHER INFORMATION: n, d or deleted
<220> FEATURE:
<221> NAME/KEY: MISC_FEATURE
<222> LOCATION: (72)..(72)
<223> OTHER INFORMATION: p, a, s or deleted

<400> SEQUENCE: 4

Xaa Glu Leu Arg Cys Xaa Cys Ile Arg Xaa Xaa Ser Xaa Pro Phe Xaa
 1               5                  10                  15

Pro Lys Xaa Ile Xaa Glu Xaa Xaa Xaa Ile Xaa Ser Pro Pro His Cys
            20                  25                  30

Xaa Asn Xaa Glu Ile Ile Val Lys Leu Xaa Xaa Gly Xaa Glu Xaa Cys
        35                  40                  45

Leu Xaa Pro Xaa Xaa Xaa Trp Val Gln Xaa Xaa Val Xaa Xaa Phe Xaa
    50                  55                  60

Lys Xaa Xaa Glu Xaa Xaa Xaa Xaa
 65                  70

<210> SEQ ID NO 5
<211> LENGTH: 72
<212> TYPE: PRT
<213> ORGANISM: artificial
<220> FEATURE:
<223> OTHER INFORMATION: synthesized using consensus sequence from
      human, bovine, sheep, pig, dolphin, horse, cat and rhesus monkey
      sequences
<220> FEATURE:
<221> NAME/KEY: MISC_FEATURE
<222> LOCATION: (1)..(1)
<223> OTHER INFORMATION: s, a, t or k
<220> FEATURE:
<221> NAME/KEY: MISC_FEATURE
<222> LOCATION: (13)..(13)
<223> OTHER INFORMATION: t or k
<220> FEATURE:
<221> NAME/KEY: MISC_FEATURE
<222> LOCATION: (19)..(19)
<223> OTHER INFORMATION: f, y or l
<220> FEATURE:
<221> NAME/KEY: MISC_FEATURE
<222> LOCATION: (27)..(27)
<223> OTHER INFORMATION: d or e
<220> FEATURE:
<221> NAME/KEY: MISC_FEATURE
<222> LOCATION: (33)..(33)
<223> OTHER INFORMATION: v, a or e
<220> FEATURE:
<221> NAME/KEY: MISC_FEATURE
<222> LOCATION: (35)..(35)
<223> OTHER INFORMATION: t or s
<220> FEATURE:
<221> NAME/KEY: MISC_FEATURE
<222> LOCATION: (42)..(42)
<223> OTHER INFORMATION: s, v, t or f
```

```
<220> FEATURE:
<221> NAME/KEY: MISC_FEATURE
<222> LOCATION: (43)..(43)
<223> OTHER INFORMATION: d or n
<220> FEATURE:
<221> NAME/KEY: MISC_FEATURE
<222> LOCATION: (45)..(45)
<223> OTHER INFORMATION: r, a, n or k
<220> FEATURE:
<221> NAME/KEY: MISC_FEATURE
<222> LOCATION: (47)..(47)
<223> OTHER INFORMATION: l or v
<220> FEATURE:
<221> NAME/KEY: MISC_FEATURE
<222> LOCATION: (54)..(54)
<223> OTHER INFORMATION: p, n or k
<220> FEATURE:
<221> NAME/KEY: MISC_FEATURE
<222> LOCATION: (58)..(58)
<223> OTHER INFORMATION: r, k or i
<220> FEATURE:
<221> NAME/KEY: MISC_FEATURE
<222> LOCATION: (61)..(61)
<223> OTHER INFORMATION: e or q
<220> FEATURE:
<221> NAME/KEY: MISC_FEATURE
<222> LOCATION: (62)..(62)
<223> OTHER INFORMATION: k, i, v or a
<220> FEATURE:
<221> NAME/KEY: MISC_FEATURE
<222> LOCATION: (66)..(66)
<223> OTHER INFORMATION: r or k
<220> FEATURE:
<221> NAME/KEY: MISC_FEATURE
<222> LOCATION: (69)..(69)
<223> OTHER INFORMATION: s, n, k or g
<220> FEATURE:
<221> NAME/KEY: MISC_FEATURE
<222> LOCATION: (70)..(70)
<223> OTHER INFORMATION: q, s, k or deleted
<220> FEATURE:
<221> NAME/KEY: MISC_FEATURE
<222> LOCATION: (71)..(71)
<223> OTHER INFORMATION: n, d or deleted
<220> FEATURE:
<221> NAME/KEY: MISC_FEATURE
<222> LOCATION: (72)..(72)
<223> OTHER INFORMATION: p, a, s or deleted

<400> SEQUENCE: 5

Xaa Glu Leu Arg Cys Gln Cys Ile Arg Lys Thr Ser Xaa Pro Phe His
1               5                   10                  15

Pro Lys Xaa Ile Lys Glu Leu Arg Val Ile Xaa Ser Pro Pro His Cys
            20                  25                  30

Xaa Asn Xaa Glu Ile Ile Val Lys Leu Xaa Xaa Gly Xaa Glu Xaa Cys
        35                  40                  45

Leu Asp Pro Lys Glu Xaa Trp Val Gln Xaa Val Val Xaa Xaa Phe Leu
    50                  55                  60

Lys Xaa Ala Glu Xaa Xaa Xaa Xaa
65                  70

<210> SEQ ID NO 6
<211> LENGTH: 72
<212> TYPE: PRT
<213> ORGANISM: artificial
<220> FEATURE:
<223> OTHER INFORMATION: synthesized from bovine sequence

<400> SEQUENCE: 6

Thr Glu Leu Arg Cys Gln Cys Ile Arg Thr His Ser Thr Pro Phe His
1               5                   10                  15
```

```
Pro Lys Phe Ile Lys Glu Leu Arg Val Ile Glu Ser Pro Pro His Cys
            20                  25                  30

Glu Asn Ser Glu Ile Ile Val Lys Leu Thr Asn Gly Asn Glu Val Cys
            35                  40                  45

Leu Asn Pro Lys Glu Lys Trp Val Gln Lys Val Gln Val Phe Val
        50                  55                  60

Lys Arg Ala Glu Lys Gln Asp Pro
65                  70

<210> SEQ ID NO 7
<211> LENGTH: 72
<212> TYPE: PRT
<213> ORGANISM: artificial
<220> FEATURE:
<223> OTHER INFORMATION: synthesized from bovine sequence

<400> SEQUENCE: 7

Thr Glu Leu Arg Cys Gln Cys Ile Arg Thr His Ser Thr Pro Phe His
1               5                   10                  15

Pro Lys Phe Ile Lys Glu Leu Arg Val Ile Glu Ser Gly Gly His Cys
            20                  25                  30

Glu Asn Ser Glu Ile Ile Val Lys Leu Thr Asn Gly Asn Glu Val Cys
            35                  40                  45

Leu Asn Pro Lys Glu Lys Trp Val Gln Lys Val Gln Val Phe Val
        50                  55                  60

Lys Arg Ala Glu Lys Gln Asp Pro
65                  70

<210> SEQ ID NO 8
<211> LENGTH: 72
<212> TYPE: PRT
<213> ORGANISM: artificial
<220> FEATURE:
<223> OTHER INFORMATION: synthesized from bovine sequence

<400> SEQUENCE: 8

Thr Glu Leu Arg Cys Gln Cys Ile Arg Ser Pro Ser Thr Pro Phe His
1               5                   10                  15

Pro Lys Phe Ile Lys Glu Leu Arg Val Ile Glu Ser Pro Pro His Cys
            20                  25                  30

Glu Asn Ser Glu Ile Ile Val Lys Leu Thr Asn Gly Asn Glu Val Cys
            35                  40                  45

Leu Asn Pro Lys Glu Lys Trp Val Gln Lys Val Gln Val Phe Val
        50                  55                  60

Lys Arg Ala Glu Lys Gln Asp Pro
65                  70

<210> SEQ ID NO 9
<211> LENGTH: 72
<212> TYPE: PRT
<213> ORGANISM: artificial
<220> FEATURE:
<223> OTHER INFORMATION: synthesized from bovine sequence

<400> SEQUENCE: 9

Thr Glu Leu Arg Cys Gln Cys Ile Arg Ser Pro Ser Thr Pro Phe His
1               5                   10                  15

Pro Lys Phe Ile Lys Glu Leu Arg Val Ile Glu Ser Pro Gly His Cys
            20                  25                  30

Glu Asn Ser Glu Ile Ile Val Lys Leu Thr Asn Gly Asn Glu Val Cys
```

```
                35                  40                  45
Leu Asn Pro Lys Glu Lys Trp Val Gln Lys Val Gln Val Phe Val
        50                  55                  60

Lys Arg Ala Glu Lys Gln Asp Pro
65                  70

<210> SEQ ID NO 10
<211> LENGTH: 72
<212> TYPE: PRT
<213> ORGANISM: artificial
<220> FEATURE:
<223> OTHER INFORMATION: synthesized from human and bovine sequences

<400> SEQUENCE: 10

Gly Ser Thr Glu Leu Arg Cys Gln Cys Ile Arg Thr His Ser Thr Pro
1               5                  10                  15

Phe His Pro Lys Phe Ile Lys Glu Leu Arg Val Ile Glu Ser Pro Pro
                20                  25                  30

His Cys Glu Asn Ser Glu Ile Ile Val Lys Leu Thr Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70

<210> SEQ ID NO 11
<211> LENGTH: 70
<212> TYPE: PRT
<213> ORGANISM: artificial
<220> FEATURE:
<223> OTHER INFORMATION: synthesized from human sequence

<400> SEQUENCE: 11

Lys Glu Leu Arg Cys Gln Cys Ile Arg Thr Tyr Ser Lys Pro Phe His
1               5                  10                  15

Pro Lys Phe Ile Lys Glu Leu Arg Val Ile Glu Ser Pro Pro His Cys
                20                  25                  30

Ala Asn Thr Glu Ile Ile Val Lys Leu Ser Asp Gly Arg Glu Leu Cys
            35                  40                  45

Leu Asp Pro Lys Glu Asn Trp Val Gln Arg Val Val Glu Lys Phe Leu
        50                  55                  60

Lys Arg Ala Glu Asn Ser
65                  70

<210> SEQ ID NO 12
<211> LENGTH: 69
<212> TYPE: PRT
<213> ORGANISM: artificial
<220> FEATURE:
<223> OTHER INFORMATION: synthesized from human sequence

<400> SEQUENCE: 12

Glu Leu Arg Cys Gln Cys Ile Arg Thr Tyr Ser Lys Pro Phe His Pro
1               5                  10                  15

Lys Phe Ile Lys Glu Leu Arg Val Ile Glu Ser Pro Pro His Cys Ala
                20                  25                  30

Asn Thr Glu Ile Ile Val Lys Leu Ser Asp Gly Arg Glu Leu Cys Leu
            35                  40                  45

Asp Pro Lys Glu Asn Trp Val Gln Arg Val Val Glu Lys Phe Leu Lys
        50                  55                  60
```

```
Arg Ala Glu Asn Ser
 65

<210> SEQ ID NO 13
<211> LENGTH: 72
<212> TYPE: PRT
<213> ORGANISM: artificial
<220> FEATURE:
<223> OTHER INFORMATION: synthesized from human sequence

<400> SEQUENCE: 13

Gly Ser Lys Glu Leu Arg Cys Gln Cys Ile Arg Thr Tyr Ser Lys Pro
 1               5                  10                  15

Phe His Pro Lys Phe Ile Lys Glu Leu Arg Val Ile Glu Ser Pro Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
 65                  70

<210> SEQ ID NO 14
<211> LENGTH: 76
<212> TYPE: PRT
<213> ORGANISM: artificial
<220> FEATURE:
<223> OTHER INFORMATION: synthesized from human sequence

<400> SEQUENCE: 14

Gly Ser Met Gly Gly Ser Lys Glu Leu Arg Cys Gln Cys Ile Arg Thr
 1               5                  10                  15

Tyr Ser Lys Pro Phe His Pro Lys Phe Ile Lys Glu Leu Arg Val Ile
            20                  25                  30

Glu Ser Pro Pro His Cys Ala Asn Thr Glu Ile Ile Val Lys Leu Ser
        35                  40                  45

Asp Gly Arg Glu Leu Cys Leu Asp Pro Lys Glu Asn Trp Val Gln Arg
    50                  55                  60

Val Val Glu Lys Phe Leu Lys Arg Ala Glu Asn Ser
 65                  70                  75

<210> SEQ ID NO 15
<211> LENGTH: 72
<212> TYPE: PRT
<213> ORGANISM: artificial
<220> FEATURE:
<223> OTHER INFORMATION: synthesized from human sequence

<400> SEQUENCE: 15

Gly Ser Thr Glu Leu Arg Cys Gln Cys Ile Arg Thr Tyr Ser Lys Pro
 1               5                  10                  15

Phe His Pro Lys Phe Ile Lys Glu Leu Arg Val Ile Glu Ser Pro Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
 65                  70
```

<210> SEQ ID NO 16
<211> LENGTH: 72
<212> TYPE: PRT
<213> ORGANISM: artificial
<220> FEATURE:
<223> OTHER INFORMATION: synthesized from human sequence

<400> SEQUENCE: 16

Gly Ser Lys Glu Leu Arg Cys Gln Cys Ile Arg Thr His Ser Lys Pro
1               5                   10                  15

Phe His Pro Lys Phe Ile Lys Glu Leu Arg Val Ile Glu Ser Pro Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 17
<211> LENGTH: 72
<212> TYPE: PRT
<213> ORGANISM: artificial
<220> FEATURE:
<223> OTHER INFORMATION: synthesized from human sequence

<400> SEQUENCE: 17

Gly Ser Lys Glu Leu Arg Cys Gln Cys Ile Arg Thr Tyr Ser Thr Pro
1               5                   10                  15

Phe His Pro Lys Phe Ile Lys Glu Leu Arg Val Ile Glu Ser Pro Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 18
<211> LENGTH: 72
<212> TYPE: PRT
<213> ORGANISM: artificial
<220> FEATURE:
<223> OTHER INFORMATION: synthesized from human sequence

<400> SEQUENCE: 18

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Glu Ser Pro Pro
            20                  25                  30

His Cys Glu Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 19
<211> LENGTH: 72
<212> TYPE: PRT

```
<213> ORGANISM: artificial
<220> FEATURE:
<223> OTHER INFORMATION: synthesized from human sequence

<400> SEQUENCE: 19

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Glu Ser Pro Pro
                20                  25                  30

His Cys Ala Asn Ser Glu Ile Ile Val Lys Leu Ser Asp Gly Arg Glu
            35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 20
<211> LENGTH: 72
<212> TYPE: PRT
<213> ORGANISM: artificial
<220> FEATURE:
<223> OTHER INFORMATION: synthesized from human sequence

<400> SEQUENCE: 20

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Glu Ser Pro Pro
                20                  25                  30

His Cys Ala Asn Thr Glu Ile Ile Val Lys Leu Thr Asp Gly Arg Glu
            35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 21
<211> LENGTH: 72
<212> TYPE: PRT
<213> ORGANISM: artificial
<220> FEATURE:
<223> OTHER INFORMATION: synthesized from human sequence

<400> SEQUENCE: 21

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Glu Ser Pro Pro
                20                  25                  30

His Cys Ala Asn Thr Glu Ile Ile Val Lys Leu Ser Asp Gly Asp Glu
            35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 22
<211> LENGTH: 72
<212> TYPE: PRT
<213> ORGANISM: artificial
<220> FEATURE:
<223> OTHER INFORMATION: synthesized from human sequence
```

```
<400> SEQUENCE: 22

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Glu Ser Pro Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Lys Trp Val Gln Arg Val Val Glu Lys
    50                  55                  60

Phe Leu Lys Arg Ala Glu Asn Ser
65                  70

<210> SEQ ID NO 23
<211> LENGTH: 72
<212> TYPE: PRT
<213> ORGANISM: artificial
<220> FEATURE:
<223> OTHER INFORMATION: synthesized from human sequence

<400> SEQUENCE: 23

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Glu Ser Pro Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Lys Val Val Glu Lys
    50                  55                  60

Phe Leu Lys Arg Ala Glu Asn Ser
65                  70

<210> SEQ ID NO 24
<211> LENGTH: 72
<212> TYPE: PRT
<213> ORGANISM: artificial
<220> FEATURE:
<223> OTHER INFORMATION: synthesized from human sequence

<400> SEQUENCE: 24

Gly Ser Lys Glu Leu Arg Cys Gln Cys Ile Arg Thr Tyr Ser Lys Pro
1               5                   10                  15

Phe His Pro Lys Phe Ile Lys Glu Leu Arg Val Ile Glu Ser Pro Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Val
    50                  55                  60

Phe Leu Lys Arg Ala Glu Asn Ser
65                  70

<210> SEQ ID NO 25
<211> LENGTH: 72
<212> TYPE: PRT
<213> ORGANISM: artificial
<220> FEATURE:
<223> OTHER INFORMATION: synthesized from human sequence

<400> SEQUENCE: 25

Gly Ser Lys Glu Leu Arg Cys Gln Cys Ile Arg Thr Tyr Ser Lys Pro
1               5                   10                  15
```

```
Phe His Pro Lys Phe Ile Lys Glu Leu Arg Val Ile Glu Ser Pro Pro
            20                  25                  30

His Cys Ala Asn Thr Glu Ile Ile Val Lys Leu Ser Asp Gly Arg Glu
        35                  40                  45

Val Cys Leu Asp Pro Lys Glu Asn Trp Val Gln Arg Val Val Glu Lys
    50                  55                  60

Phe Leu Lys Arg Ala Glu Asn Ser
65                  70
```

<210> SEQ ID NO 26
<211> LENGTH: 72
<212> TYPE: PRT
<213> ORGANISM: artificial
<220> FEATURE:
<223> OTHER INFORMATION: synthesized from human and bovine sequences

<400> SEQUENCE: 26

```
Gly Ser Lys Glu Leu Arg Cys Gln Cys Ile Arg Thr His Ser Thr Pro
1               5                   10                  15

Phe His Pro Lys Phe Ile Lys Glu Leu Arg Val Ile Glu Ser Pro Pro
            20                  25                  30

His Cys Glu Asn Ser Glu Ile Ile Val Lys Leu Thr Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70
```

<210> SEQ ID NO 27
<211> LENGTH: 72
<212> TYPE: PRT
<213> ORGANISM: artificial
<220> FEATURE:
<223> OTHER INFORMATION: synthesized from human and bovine sequences

<400> SEQUENCE: 27

```
Gly Ser Thr Glu Leu Arg Cys Gln Cys Ile Arg Thr Tyr Ser Thr Pro
1               5                   10                  15

Phe His Pro Lys Phe Ile Lys Glu Leu Arg Val Ile Glu Ser Pro Pro
            20                  25                  30

His Cys Glu Asn Ser Glu Ile Ile Val Lys Leu Thr Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70
```

<210> SEQ ID NO 28
<211> LENGTH: 72
<212> TYPE: PRT
<213> ORGANISM: artificial
<220> FEATURE:
<223> OTHER INFORMATION: synthesized from human and bovine sequences

<400> SEQUENCE: 28

```
Gly Ser Thr Glu Leu Arg Cys Gln Cys Ile Arg Thr His Ser Lys Pro
1               5                   10                  15

Phe His Pro Lys Phe Ile Lys Glu Leu Arg Val Ile Glu Ser Pro Pro
            20                  25                  30
```

His Cys Glu Asn Ser Glu Ile Ile Val Lys Leu Thr Asp Gly Arg Glu
            35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 29
<211> LENGTH: 72
<212> TYPE: PRT
<213> ORGANISM: artificial
<220> FEATURE:
<223> OTHER INFORMATION: synthesized from human and bovine sequences

<400> SEQUENCE: 29

Gly Ser Thr Glu Leu Arg Cys Gln Cys Ile Arg Thr His Ser Thr Pro
1               5                   10                  15

Phe His Pro Lys Phe Ile Lys Glu Leu Arg Val Ile Glu Ser Pro Pro
            20                  25                  30

His Cys Ala Asn Ser Glu Ile Ile Val Lys Leu Thr Asp Gly Arg Glu
            35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 30
<211> LENGTH: 72
<212> TYPE: PRT
<213> ORGANISM: artificial
<220> FEATURE:
<223> OTHER INFORMATION: synthesized from human and bovine sequences

<400> SEQUENCE: 30

Gly Ser Thr Glu Leu Arg Cys Gln Cys Ile Arg Thr His Ser Thr Pro
1               5                   10                  15

Phe His Pro Lys Phe Ile Lys Glu Leu Arg Val Ile Glu Ser Pro Pro
            20                  25                  30

His Cys Glu Asn Thr Glu Ile Ile Val Lys Leu Thr Asp Gly Arg Glu
            35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 31
<211> LENGTH: 76
<212> TYPE: PRT
<213> ORGANISM: artificial
<220> FEATURE:
<223> OTHER INFORMATION: synthesized from human and bovine sequences

<400> SEQUENCE: 31

Gly Ser Met Gly Gly Ser Thr Glu Leu Arg Cys Gln Cys Ile Arg Thr
1               5                   10                  15

His Ser Thr Pro Phe His Pro Lys Phe Ile Lys Glu Leu Arg Val Ile
            20                  25                  30

Glu Ser Pro Pro His Cys Glu Asn Ser Glu Ile Ile Val Lys Leu Thr
            35                  40                  45

Asp Gly Arg Glu Leu Cys Leu Asp Pro Lys Glu Asn Trp Val Gln Arg

```
                50                  55                  60
Val Val Glu Lys Phe Leu Lys Arg Ala Glu Asn Ser
65                  70                  75

<210> SEQ ID NO 32
<211> LENGTH: 72
<212> TYPE: PRT
<213> ORGANISM: artificial
<220> FEATURE:
<223> OTHER INFORMATION: synthesized from human and bovine sequences

<400> SEQUENCE: 32

Gly Ser Thr Glu Leu Arg Cys Gln Cys Ile Arg Thr His Ser Thr Pro
1               5                   10                  15

Phe His Pro Lys Phe Ile Lys Glu Leu Arg Val Ile Glu Ser Pro Pro
                20                  25                  30

His Cys Glu Asn Ser Glu Ile Ile Val Lys Leu Thr Asp Gly Arg Glu
            35                  40                  45

Leu Cys Leu Asp Pro Lys Glu Asn Trp Val Gln Arg Val Val Glu Lys
        50                  55                  60

Phe Leu Lys Arg Ala Glu Asn Ser
65                  70

<210> SEQ ID NO 33
<211> LENGTH: 70
<212> TYPE: PRT
<213> ORGANISM: artificial
<220> FEATURE:
<223> OTHER INFORMATION: synthesized from human and bovine sequences

<400> SEQUENCE: 33

Thr Glu Leu Arg Cys Gln Cys Ile Arg Thr His Ser Thr Pro Phe His
1               5                   10                  15

Pro Lys Phe Ile Lys Glu Leu Arg Val Ile Glu Ser Pro Pro His Cys
                20                  25                  30

Glu Asn Ser Glu Ile Ile Val Lys Leu Thr Asp Gly Arg Glu Leu Cys
            35                  40                  45

Leu Asp Pro Lys Glu Asn Trp Val Gln Arg Val Val Glu Lys Phe Leu
        50                  55                  60

Lys Arg Ala Glu Asn Ser
65                  70

<210> SEQ ID NO 34
<211> LENGTH: 69
<212> TYPE: PRT
<213> ORGANISM: artificial
<220> FEATURE:
<223> OTHER INFORMATION: synthesized from human and bovine sequences

<400> SEQUENCE: 34

Glu Leu Arg Cys Gln Cys Ile Arg Thr His Ser Thr Pro Phe His Pro
1               5                   10                  15

Lys Phe Ile Lys Glu Leu Arg Val Ile Glu Ser Pro Pro His Cys Glu
                20                  25                  30

Asn Ser Glu Ile Ile Val Lys Leu Thr Asp Gly Arg Glu Leu Cys Leu
            35                  40                  45

Asp Pro Lys Glu Asn Trp Val Gln Arg Val Val Glu Lys Phe Leu Lys
        50                  55                  60

Arg Ala Glu Asn Ser
65
```

<210> SEQ ID NO 35
<211> LENGTH: 76
<212> TYPE: PRT
<213> ORGANISM: artificial
<220> FEATURE:
<223> OTHER INFORMATION: synthesized from human sequence

<400> SEQUENCE: 35

Gly Ser Met Gly Gly Ser Lys Glu Leu Arg Cys Gln Cys Ile Arg Thr
1               5                   10                  15

Tyr Ser Lys Pro Phe His Pro Lys Phe Ile Lys Glu Leu Arg Val Ile
                20                  25                  30

Glu Ser Gly Pro His Cys Ala Asn Thr Glu Ile Ile Val Lys Leu Ser
            35                  40                  45

Asp Gly Arg Glu Leu Cys Leu Asp Pro Lys Glu Asn Trp Val Gln Arg
        50                  55                  60

Val Val Glu Lys Phe Leu Lys Arg Ala Glu Asn Ser
65                  70                  75

<210> SEQ ID NO 36
<211> LENGTH: 76
<212> TYPE: PRT
<213> ORGANISM: artificial
<220> FEATURE:
<223> OTHER INFORMATION: synthesized from human sequence

<400> SEQUENCE: 36

Gly Ser Met Gly Gly Ser Lys Glu Leu Arg Cys Gln Cys Ile Arg Thr
1               5                   10                  15

Tyr Ser Lys Pro Phe His Pro Lys Phe Ile Lys Glu Leu Arg Val Ile
                20                  25                  30

Glu Ser Pro Pro His Cys Glu Asn Thr Glu Ile Ile Val Lys Leu Ser
            35                  40                  45

Asp Gly Arg Glu Leu Cys Leu Asp Pro Lys Glu Asn Trp Val Gln Arg
        50                  55                  60

Val Val Glu Lys Phe Leu Lys Arg Ala Glu Asn Ser
65                  70                  75

<210> SEQ ID NO 37
<211> LENGTH: 76
<212> TYPE: PRT
<213> ORGANISM: artificial
<220> FEATURE:
<223> OTHER INFORMATION: synthesized from human sequence

<400> SEQUENCE: 37

Gly Ser Met Gly Gly Ser Lys Glu Leu Arg Cys Gln Cys Ile Arg Thr
1               5                   10                  15

Tyr Ser Lys Pro Phe His Pro Lys Phe Ile Lys Glu Leu Arg Val Ile
                20                  25                  30

Glu Ser Pro Pro His Cys Ala Asn Ser Glu Ile Ile Val Lys Leu Ser
            35                  40                  45

Asp Gly Arg Glu Leu Cys Leu Asp Pro Lys Glu Asn Trp Val Gln Arg
        50                  55                  60

Val Val Glu Lys Phe Leu Lys Arg Ala Glu Asn Ser
65                  70                  75

<210> SEQ ID NO 38
<211> LENGTH: 76

```
<212> TYPE: PRT
<213> ORGANISM: artificial
<220> FEATURE:
<223> OTHER INFORMATION: synthesized from human sequence

<400> SEQUENCE: 38

Gly Ser Met Gly Gly Ser Lys Glu Leu Arg Cys Gln Cys Ile Arg Thr
1               5                   10                  15

Tyr Ser Lys Pro Phe His Pro Lys Phe Ile Lys Glu Leu Arg Val Ile
                20                  25                  30

Glu Ser Pro Pro His Cys Ala Asn Thr Glu Ile Ile Val Lys Leu Thr
            35                  40                  45

Asp Gly Arg Glu Leu Cys Leu Asp Pro Lys Glu Asn Trp Val Gln Arg
        50                  55                  60

Val Val Glu Lys Phe Leu Lys Arg Ala Glu Asn Ser
65                  70                  75

<210> SEQ ID NO 39
<211> LENGTH: 76
<212> TYPE: PRT
<213> ORGANISM: artificial
<220> FEATURE:
<223> OTHER INFORMATION: synthesized from human sequence

<400> SEQUENCE: 39

Gly Ser Met Gly Gly Ser Lys Glu Leu Arg Cys Gln Cys Ile Arg Thr
1               5                   10                  15

Tyr Ser Lys Pro Phe His Pro Lys Phe Ile Lys Glu Leu Arg Val Ile
                20                  25                  30

Glu Ser Pro Pro His Cys Ala Asn Thr Glu Ile Ile Val Lys Leu Ser
            35                  40                  45

Asp Gly Asp Glu Leu Cys Leu Asp Pro Lys Glu Asn Trp Val Gln Arg
        50                  55                  60

Val Val Glu Lys Phe Leu Lys Arg Ala Glu Asn Ser
65                  70                  75

<210> SEQ ID NO 40
<211> LENGTH: 76
<212> TYPE: PRT
<213> ORGANISM: artificial
<220> FEATURE:
<223> OTHER INFORMATION: synthesized from human sequence

<400> SEQUENCE: 40

Gly Ser Met Gly Gly Ser Lys Glu Leu Arg Cys Gln Cys Ile Arg Thr
1               5                   10                  15

Tyr Ser Lys Pro Phe His Pro Lys Phe Ile Lys Glu Leu Arg Val Ile
                20                  25                  30

Glu Ser Pro Pro His Cys Ala Asn Thr Glu Ile Ile Val Lys Leu Ser
            35                  40                  45

Asp Gly Arg Glu Val Cys Leu Asp Pro Lys Glu Asn Trp Val Gln Arg
        50                  55                  60

Val Val Glu Lys Phe Leu Lys Arg Ala Glu Asn Ser
65                  70                  75

<210> SEQ ID NO 41
<211> LENGTH: 74
<212> TYPE: PRT
<213> ORGANISM: artificial
<220> FEATURE:
<223> OTHER INFORMATION: synthesized from bovine sequence
```

<400> SEQUENCE: 41

Gly Ser Thr Glu Leu Arg Cys Gln Cys Ile Arg Thr His Ser Thr Pro
1               5                   10                  15

Phe His Pro Lys Phe Ile Lys Glu Leu Arg Val Ile Glu Ser Pro Pro
                20                  25                  30

His Cys Glu Asn Ser Glu Ile Ile Val Lys Leu Thr Asn Gly Asn Glu
            35                  40                  45

Val Cys Leu Asn Pro Lys Glu Lys Trp Val Gln Lys Val Val Gln Val
        50                  55                  60

Phe Val Lys Arg Ala Glu Lys Gln Asp Pro
65                  70

```
<210> SEQ ID NO 42
<211> LENGTH: 72
<212> TYPE: PRT
<213> ORGANISM: artificial
<220> FEATURE:
<223> OTHER INFORMATION: synthesized using consensus sequence from
      human, bovine, sheep, pig, dolphin, horse, cat and rhesus monkey
      sequences
<220> FEATURE:
<221> NAME/KEY: MISC_FEATURE
<222> LOCATION: (1)..(1)
<223> OTHER INFORMATION: 0-10 amino acids
<220> FEATURE:
<221> NAME/KEY: MISC_FEATURE
<222> LOCATION: (6)..(6)
<223> OTHER INFORMATION: any
<220> FEATURE:
<221> NAME/KEY: MISC_FEATURE
<222> LOCATION: (10)..(10)
<223> OTHER INFORMATION: any
<220> FEATURE:
<221> NAME/KEY: MISC_FEATURE
<222> LOCATION: (11)..(11)
<223> OTHER INFORMATION: any
<220> FEATURE:
<221> NAME/KEY: MISC_FEATURE
<222> LOCATION: (13)..(13)
<223> OTHER INFORMATION: any
<220> FEATURE:
<221> NAME/KEY: MISC_FEATURE
<222> LOCATION: (16)..(16)
<223> OTHER INFORMATION: any
<220> FEATURE:
<221> NAME/KEY: MISC_FEATURE
<222> LOCATION: (19)..(19)
<223> OTHER INFORMATION: any
<220> FEATURE:
<221> NAME/KEY: MISC_FEATURE
<222> LOCATION: (21)..(21)
<223> OTHER INFORMATION: any
<220> FEATURE:
<221> NAME/KEY: MISC_FEATURE
<222> LOCATION: (23)..(23)
<223> OTHER INFORMATION: any
<220> FEATURE:
<221> NAME/KEY: MISC_FEATURE
<222> LOCATION: (24)..(24)
<223> OTHER INFORMATION: any
<220> FEATURE:
<221> NAME/KEY: MISC_FEATURE
<222> LOCATION: (25)..(25)
<223> OTHER INFORMATION: any
<220> FEATURE:
<221> NAME/KEY: MISC_FEATURE
<222> LOCATION: (27)..(27)
<223> OTHER INFORMATION: any
<220> FEATURE:
<221> NAME/KEY: MISC_FEATURE
<222> LOCATION: (33)..(33)
<223> OTHER INFORMATION: any
```

```
<220> FEATURE:
<221> NAME/KEY: MISC_FEATURE
<222> LOCATION: (35)..(35)
<223> OTHER INFORMATION: any
<220> FEATURE:
<221> NAME/KEY: MISC_FEATURE
<222> LOCATION: (42)..(42)
<223> OTHER INFORMATION: any
<220> FEATURE:
<221> NAME/KEY: MISC_FEATURE
<222> LOCATION: (43)..(43)
<223> OTHER INFORMATION: any
<220> FEATURE:
<221> NAME/KEY: MISC_FEATURE
<222> LOCATION: (45)..(45)
<223> OTHER INFORMATION: any
<220> FEATURE:
<221> NAME/KEY: MISC_FEATURE
<222> LOCATION: (47)..(47)
<223> OTHER INFORMATION: any
<220> FEATURE:
<221> NAME/KEY: MISC_FEATURE
<222> LOCATION: (50)..(50)
<223> OTHER INFORMATION: any
<220> FEATURE:
<221> NAME/KEY: MISC_FEATURE
<222> LOCATION: (52)..(52)
<223> OTHER INFORMATION: any
<220> FEATURE:
<221> NAME/KEY: MISC_FEATURE
<222> LOCATION: (53)..(53)
<223> OTHER INFORMATION: any
<220> FEATURE:
<221> NAME/KEY: MISC_FEATURE
<222> LOCATION: (54)..(54)
<223> OTHER INFORMATION: any
<220> FEATURE:
<221> NAME/KEY: MISC_FEATURE
<222> LOCATION: (58)..(58)
<223> OTHER INFORMATION: any
<220> FEATURE:
<221> NAME/KEY: MISC_FEATURE
<222> LOCATION: (59)..(59)
<223> OTHER INFORMATION: any
<220> FEATURE:
<221> NAME/KEY: MISC_FEATURE
<222> LOCATION: (61)..(61)
<223> OTHER INFORMATION: any
<220> FEATURE:
<221> NAME/KEY: MISC_FEATURE
<222> LOCATION: (62)..(62)
<223> OTHER INFORMATION: any
<220> FEATURE:
<221> NAME/KEY: MISC_FEATURE
<222> LOCATION: (64)..(64)
<223> OTHER INFORMATION: any
<220> FEATURE:
<221> NAME/KEY: MISC_FEATURE
<222> LOCATION: (66)..(66)
<223> OTHER INFORMATION: any
<220> FEATURE:
<221> NAME/KEY: MISC_FEATURE
<222> LOCATION: (67)..(67)
<223> OTHER INFORMATION: any
<220> FEATURE:
<221> NAME/KEY: MISC_FEATURE
<222> LOCATION: (69)..(69)
<223> OTHER INFORMATION: any
<220> FEATURE:
<221> NAME/KEY: MISC_FEATURE
<222> LOCATION: (70)..(70)
<223> OTHER INFORMATION: 0-10 amino acids
<220> FEATURE:
<221> NAME/KEY: MISC_FEATURE
<222> LOCATION: (71)..(71)
<223> OTHER INFORMATION: 0-10 amino acids
<220> FEATURE:
<221> NAME/KEY: MISC_FEATURE
<222> LOCATION: (72)..(72)
```

<223> OTHER INFORMATION: 0-10 amino acids

<400> SEQUENCE: 42

Xaa Glu Leu Arg Cys Xaa Cys Ile Arg Xaa Xaa Ser Xaa Pro Phe Xaa
1               5                   10                  15

Pro Lys Xaa Ile Xaa Glu Xaa Xaa Xaa Ile Xaa Ser Pro Pro His Cys
            20                  25                  30

Xaa Asn Xaa Glu Ile Ile Val Lys Leu Xaa Xaa Gly Xaa Glu Xaa Cys
        35                  40                  45

Leu Xaa Pro Xaa Xaa Xaa Trp Val Gln Xaa Xaa Val Xaa Xaa Phe Xaa
    50                  55                  60

Lys Xaa Xaa Glu Xaa Xaa Xaa Xaa
65                  70

<210> SEQ ID NO 43
<211> LENGTH: 72
<212> TYPE: PRT
<213> ORGANISM: artificial
<220> FEATURE:
<223> OTHER INFORMATION: synthesized using consensus sequence from
      human, bovine, sheep, pig, dolphin, horse, cat and rhesus monkey
      sequences
<220> FEATURE:
<221> NAME/KEY: MISC_FEATURE
<222> LOCATION: (1)..(1)
<223> OTHER INFORMATION: 0-10 amino acids
<220> FEATURE:
<221> NAME/KEY: MISC_FEATURE
<222> LOCATION: (6)..(6)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (10)..(10)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (11)..(11)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (13)..(13)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (16)..(16)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (19)..(19)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (21)..(21)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (23)..(23)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (24)..(24)
<223> OTHER INFORMATION: A, D, E, F, G, H, I, K, L, M, N, P, Q, R, S, T,
      V or Y
<220> FEATURE:
<221> NAME/KEY: MISC_FEATURE

```
<222> LOCATION: (25)..(25)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (27)..(27)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (33)..(33)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (35)..(35)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (42)..(42)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (43)..(43)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (45)..(45)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (47)..(47)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (50)..(50)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (52)..(52)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (53)..(53)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (54)..(54)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (58)..(58)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (59)..(59)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (61)..(61)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (62)..(62)
<223> OTHER INFORMATION: A, D, E, F, G, H, I, K, L, M, N, P, Q, R, S, T,
      V or Y
<220> FEATURE:
```

```
<221> NAME/KEY: MISC_FEATURE
<222> LOCATION: (64)..(64)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (66)..(66)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (67)..(67)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (69)..(69)
<223> OTHER INFORMATION: A, D, E, F, G, H, I, K, L, M, N, P, Q, R, S, T,
      V or Y
<220> FEATURE:
<221> NAME/KEY: MISC_FEATURE
<222> LOCATION: (70)..(70)
<223> OTHER INFORMATION: 0-10 amino acids
<220> FEATURE:
<221> NAME/KEY: MISC_FEATURE
<222> LOCATION: (71)..(71)
<223> OTHER INFORMATION: 0-10 amino acids
<220> FEATURE:
<221> NAME/KEY: MISC_FEATURE
<222> LOCATION: (72)..(72)
<223> OTHER INFORMATION: 0-10 amino acids

<400> SEQUENCE: 43

Xaa Glu Leu Arg Cys Xaa Cys Ile Arg Xaa Xaa Ser Xaa Pro Phe Xaa
 1               5                  10                  15

Pro Lys Xaa Ile Xaa Glu Xaa Xaa Xaa Ile Xaa Ser Pro Pro His Cys
            20                  25                  30

Xaa Asn Xaa Glu Ile Ile Val Lys Leu Xaa Xaa Gly Xaa Glu Xaa Cys
        35                  40                  45

Leu Xaa Pro Xaa Xaa Xaa Trp Val Gln Xaa Xaa Val Xaa Xaa Phe Xaa
    50                  55                  60

Lys Xaa Xaa Glu Xaa Xaa Xaa Xaa
65                  70
```